(12) United States Patent
Deliencourt-Godefroy et al.

(10) Patent No.: US 9,175,044 B2
(45) Date of Patent: Nov. 3, 2015

(54) DERIVATIVES OF GLYCO-CF$_2$-SERINE AND GLYCO-CF$_2$-THREONINE

(75) Inventors: Geraldine Deliencourt-Godefroy, Bois d'Ennebourg (FR); Hyacinthe Fillon, Saint Etienne du Rouvray (FR); Thibaut Martin, Mont Saint Aignan (FR)

(73) Assignee: TFCHEM, Val-de-Reuil (FR)

( * ) Notice: Subject to any disclaimer, the term of this patent is extended or adjusted under 35 U.S.C. 154(b) by 49 days.

(21) Appl. No.: 13/823,237

(22) PCT Filed: Dec. 22, 2011

(86) PCT No.: PCT/EP2011/073822
§ 371 (c)(1),
(2), (4) Date: Mar. 14, 2013

(87) PCT Pub. No.: WO2012/085221
PCT Pub. Date: Jun. 28, 2012

(65) Prior Publication Data
US 2013/0171180 A1   Jul. 4, 2013

(30) Foreign Application Priority Data
Dec. 22, 2010   (EP) .................................... 10306493

(51) Int. Cl.
| | | |
|---|---|---|
| *C07H 7/02* | (2006.01) | |
| *C07H 7/04* | (2006.01) | |
| *C07D 309/10* | (2006.01) | |
| *C07K 9/00* | (2006.01) | |
| *C07K 5/062* | (2006.01) | |
| *C07K 5/06* | (2006.01) | |
| *C07K 5/083* | (2006.01) | |
| *C07K 5/08* | (2006.01) | |
| *A01N 1/02* | (2006.01) | |
| *A61K 8/64* | (2006.01) | |
| *A61Q 19/08* | (2006.01) | |
| *C07K 1/06* | (2006.01) | |

(52) U.S. Cl.
CPC .............. *C07K 9/001* (2013.01); *A01N 1/0226* (2013.01); *A61K 8/64* (2013.01); *A61Q 19/08* (2013.01); *C07D 309/10* (2013.01); *C07H 7/02* (2013.01); *C07H 7/04* (2013.01); *C07K 1/063* (2013.01); *C07K 5/0606* (2013.01); *C07K 5/06191* (2013.01); *C07K 5/081* (2013.01); *C07K 5/0827* (2013.01); *C07K 9/00* (2013.01)

(58) Field of Classification Search
None
See application file for complete search history.

(56) References Cited

U.S. PATENT DOCUMENTS

| | | |
|---|---|---|
| 2006/0142206 A1 | 6/2006 | Quirion et al. |
| 2009/0311203 A1 | 12/2009 | Castelot Deliencourt-Godefroy et al. |
| 2009/0318675 A1 | 12/2009 | Quirion et al. |

FOREIGN PATENT DOCUMENTS

| | | | |
|---|---|---|---|
| WO | WO 2004/014928 A2 | 2/2004 | |
| WO | WO 2006/059227 A1 | 12/2004 | |
| WO | WO 2007/125194 A1 | 11/2007 | |
| WO | WO2007/125203 | * 11/2007 | |
| WO | WO 2007/125203 A1 | 11/2007 | |

OTHER PUBLICATIONS

Allen, et al., "Properties of Potato Lectin and the Nature of its Glycoprotein Linkages", *Biochem. J.*, 1978, vol. 171, pp. 665-674.
Chorki, et al., "First Synthesis of 10α-(Trifluoromethyl) deoxoartemisinin", *Organic Letters*, 2002, vol. 4, No. 5, pp. 757-759.
Cuenca, Ana et al., "Addition of Ethyl Bromodifluoroacetate to Lactones: Reactivity and Stereoselectivity", *Synlett*, 2005, No. 17, pp. 2627-2630.
Maljaars, et al., "Affinity Determination of *Ricinus communis* Agglutinin Ligands Identified from Combinational O- and S-, N-Glycopeptide Libraries", *J. Comb. Chem.* 2006, vol. 8, pp. 812-819.
Moreno, et al., "Addition of Difluoromethyl Radicals to Glycals: A New Route to α-CF2-D-Glycosides", *Organic Letters*, 2007, vol. 9, No. 13, pp. 2477-2480.
Ramachary, et al., "Development of Pharmaceutical Drugs, Drug Intermediates and Ingredients by Using Direct Organo-Click Reactions", *Eur. J. Org. Chem.*, 2008, pp. 975-993.
Yeh, et al., "Antifreeze Proteins: Structures and Mechanisms of Function", *American Chemical Society*, vol. 96, No. 2, pp. 601-618.

* cited by examiner

*Primary Examiner* — Traviss C McIntosh, III
(74) *Attorney, Agent, or Firm* — Foley & Lardner LLP

(57) ABSTRACT

The present invention relates to compounds of formula (I): or a pharmaceutically acceptable salt thereof, a tautomer, a stereoisomer or a mixture of stereoisomers in any proportion, in particular a mixture of enantiomers, and particularly a racemate mixture, as well as to their process of preparation, their use in the peptide synthesis, said peptide and the use of said peptide.

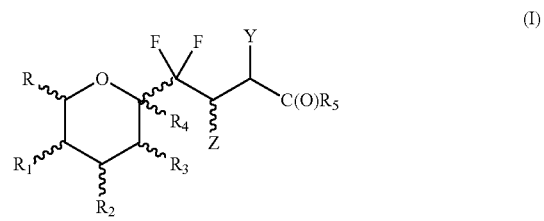

26 Claims, 13 Drawing Sheets

DERIVATIVES OF GLYCO-CF$_2$-SERINE AND GLYCO-CF$_2$-THREONINE

Figure 1A:
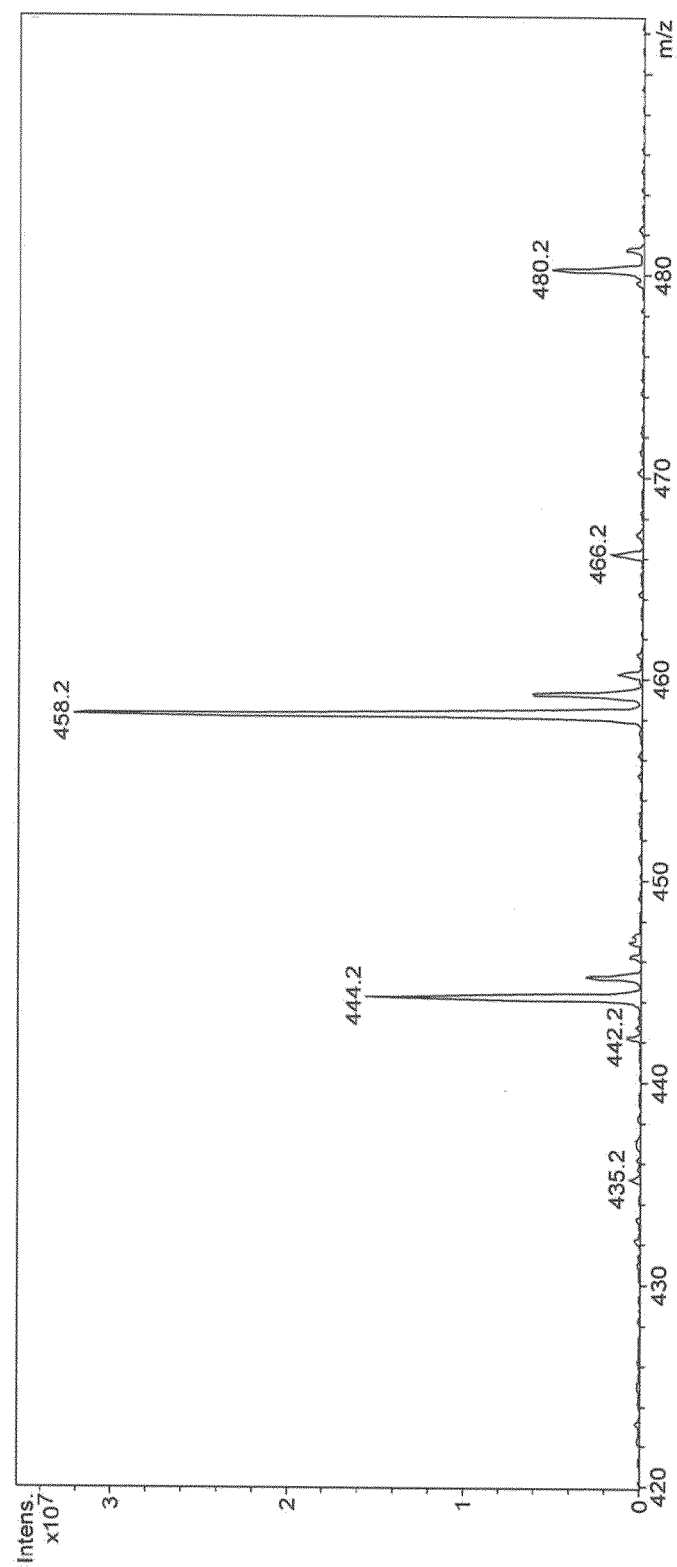
Figure 1B:
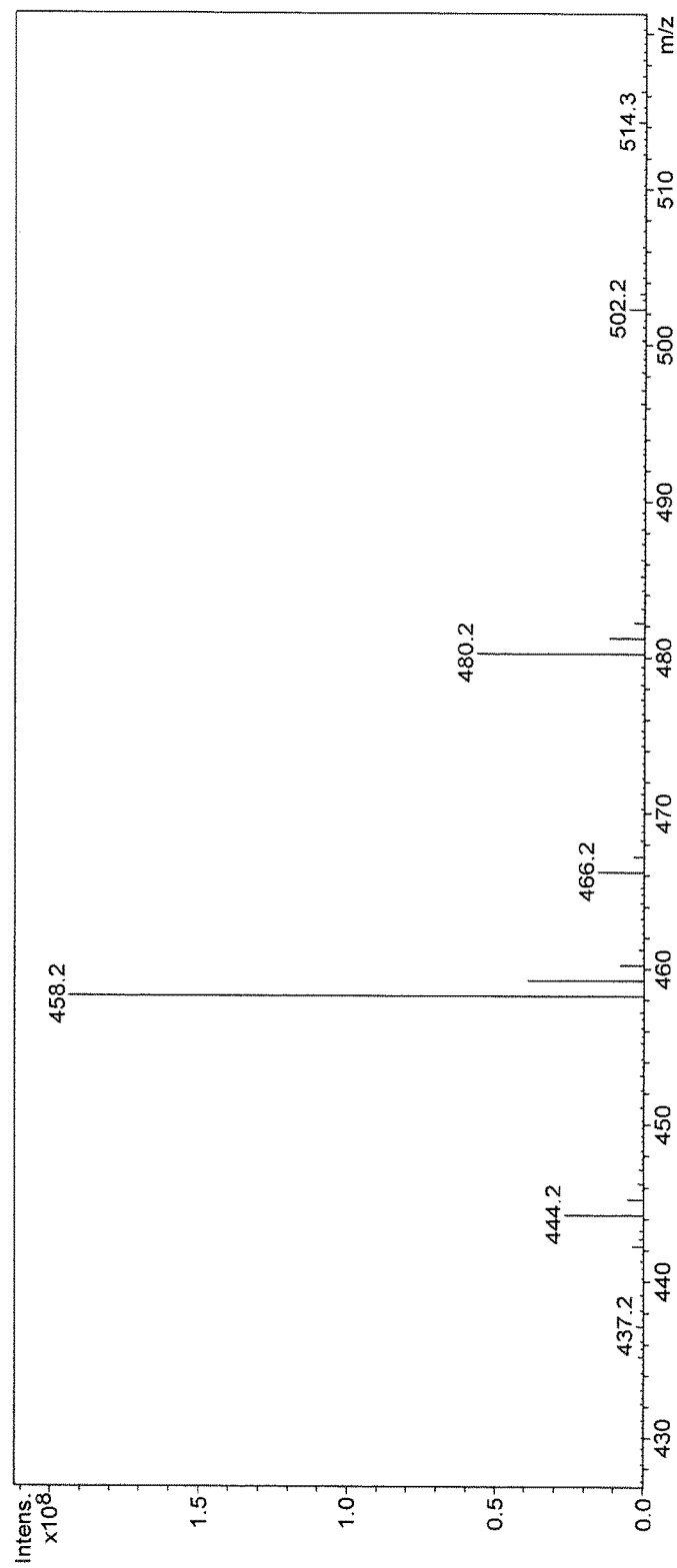
Figure 2A:
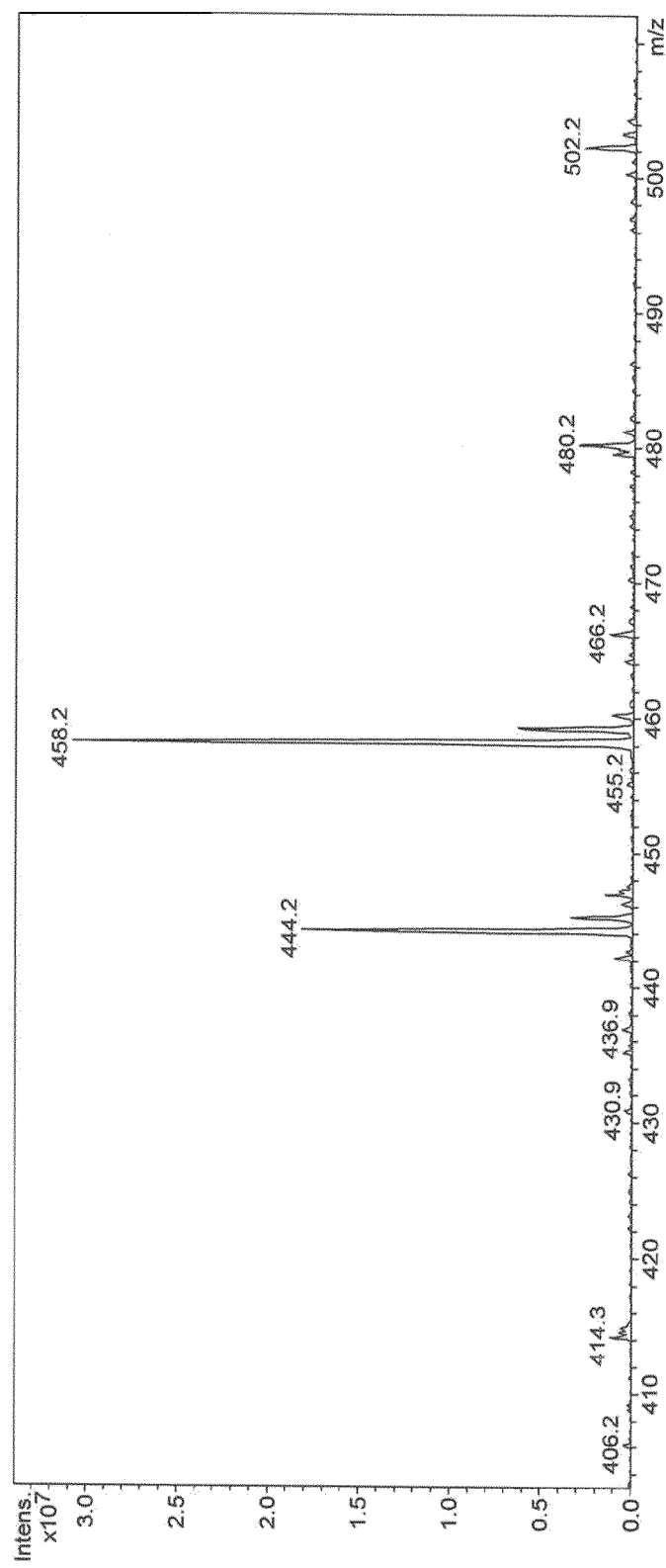
Figure 2B:
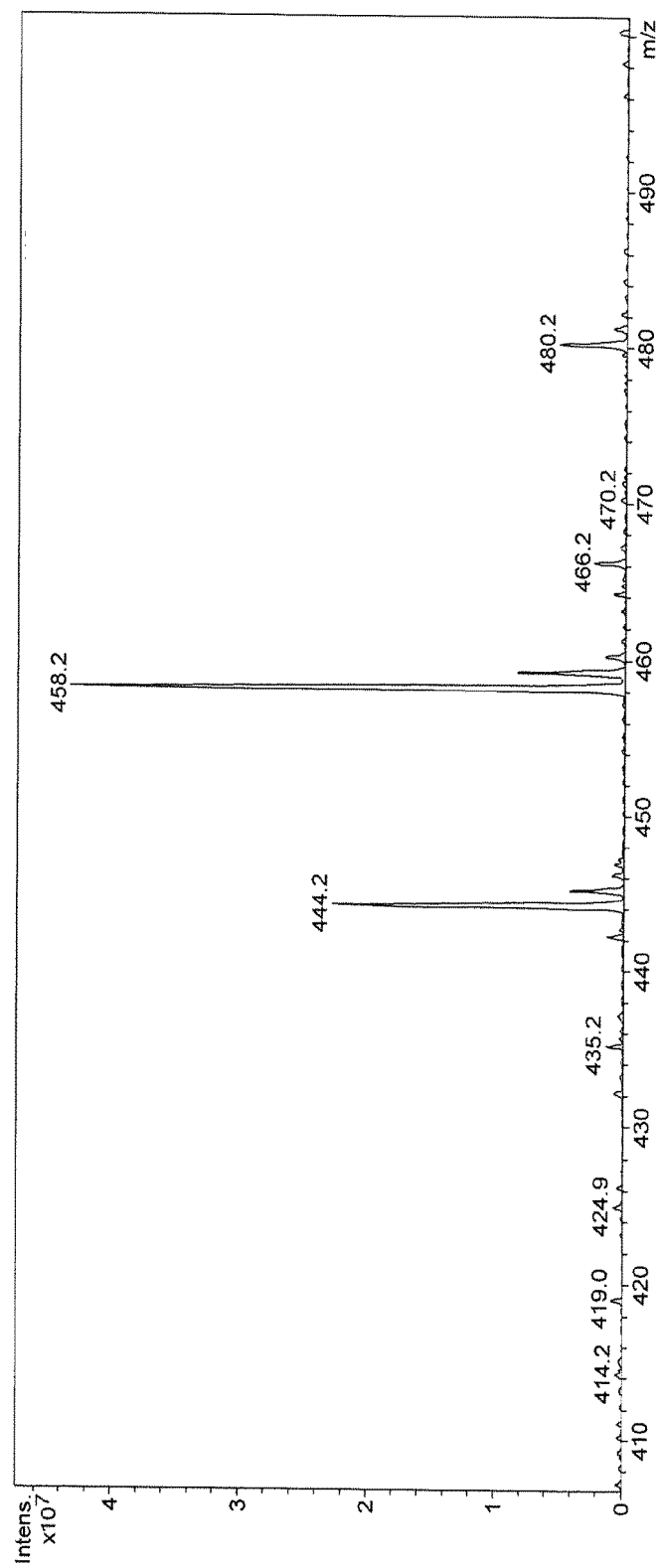
Figure 3A:
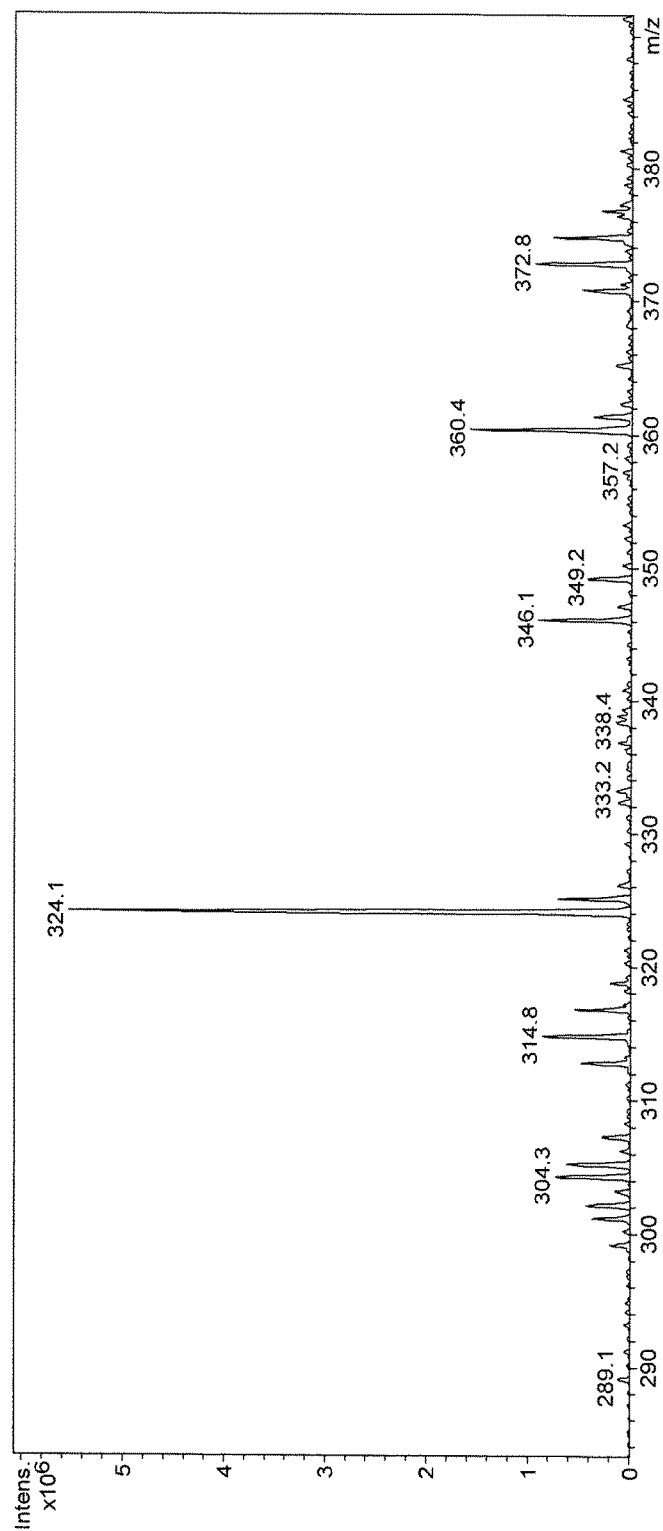
Figure 3B:
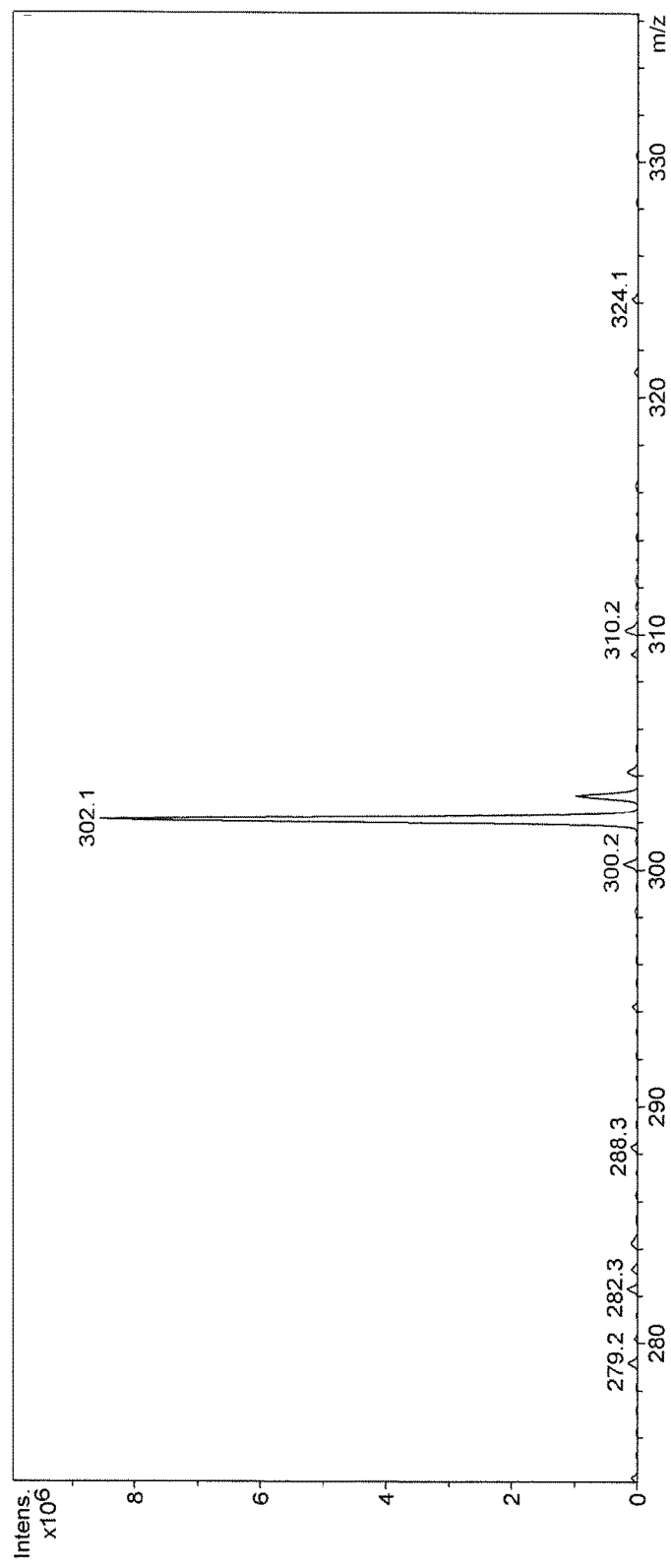
Figure 4A:
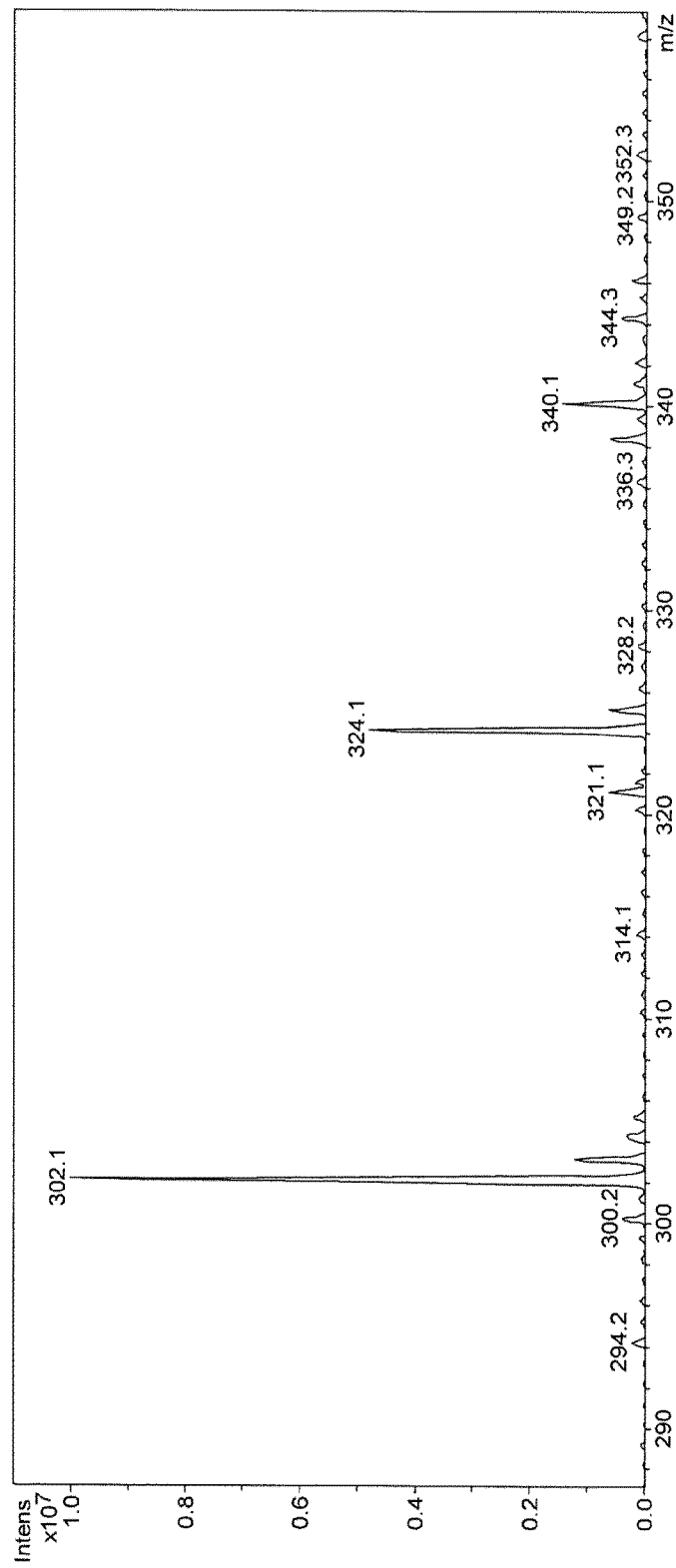
Figure 4B:
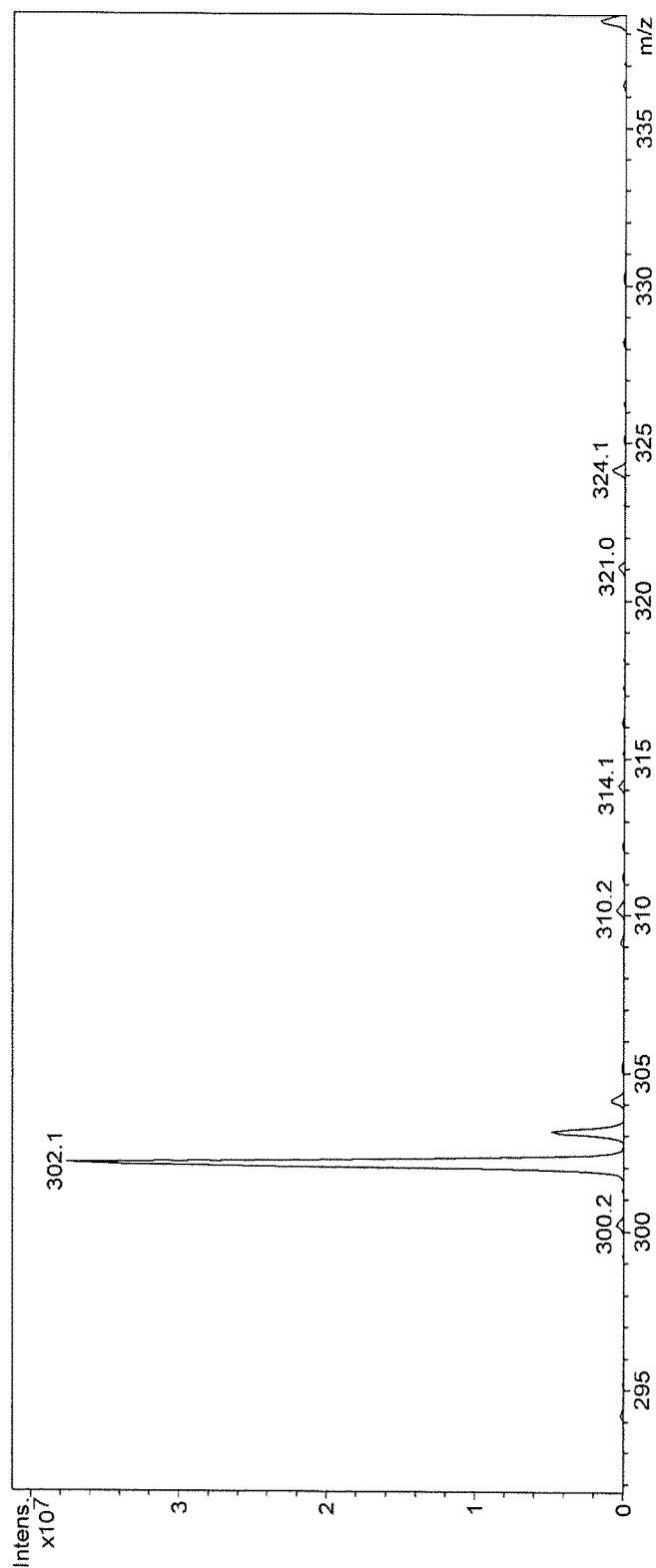
Figure 5A:
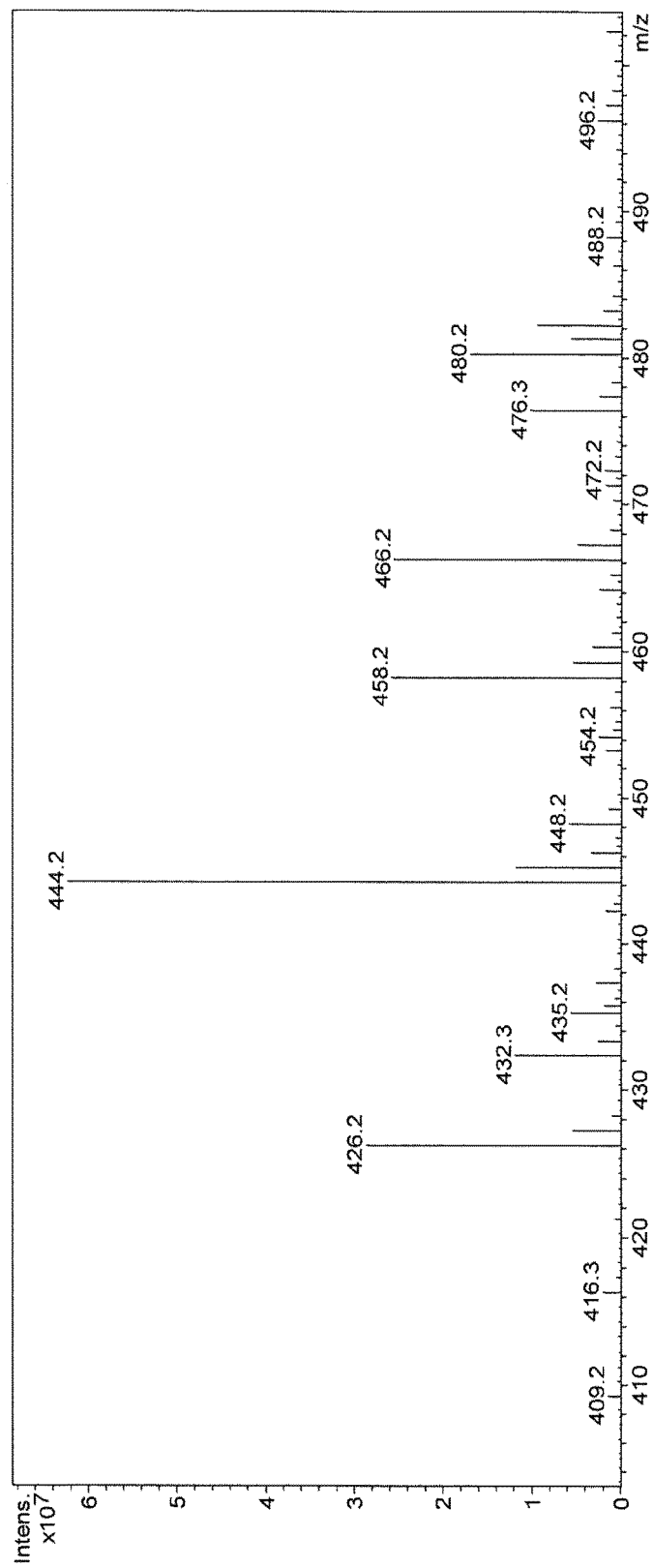
Figure 5B:
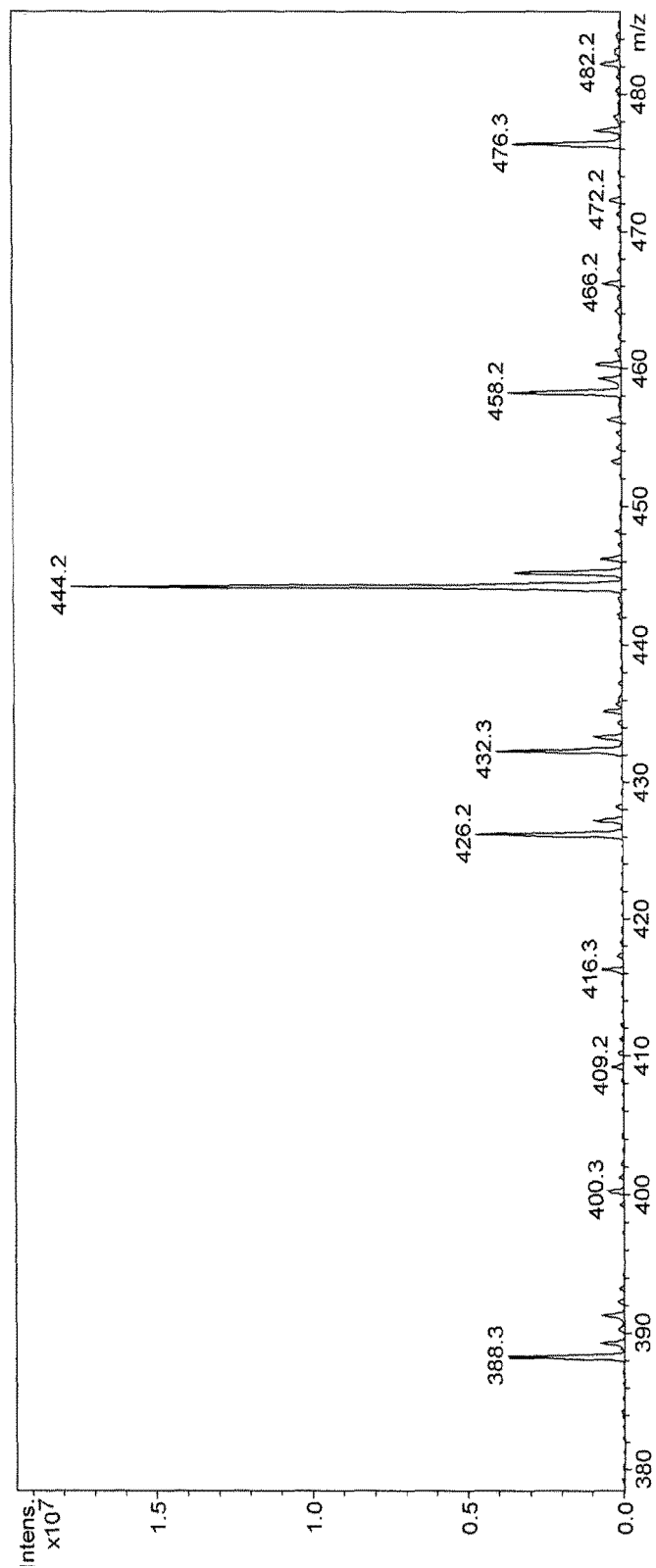
Figure 6A:
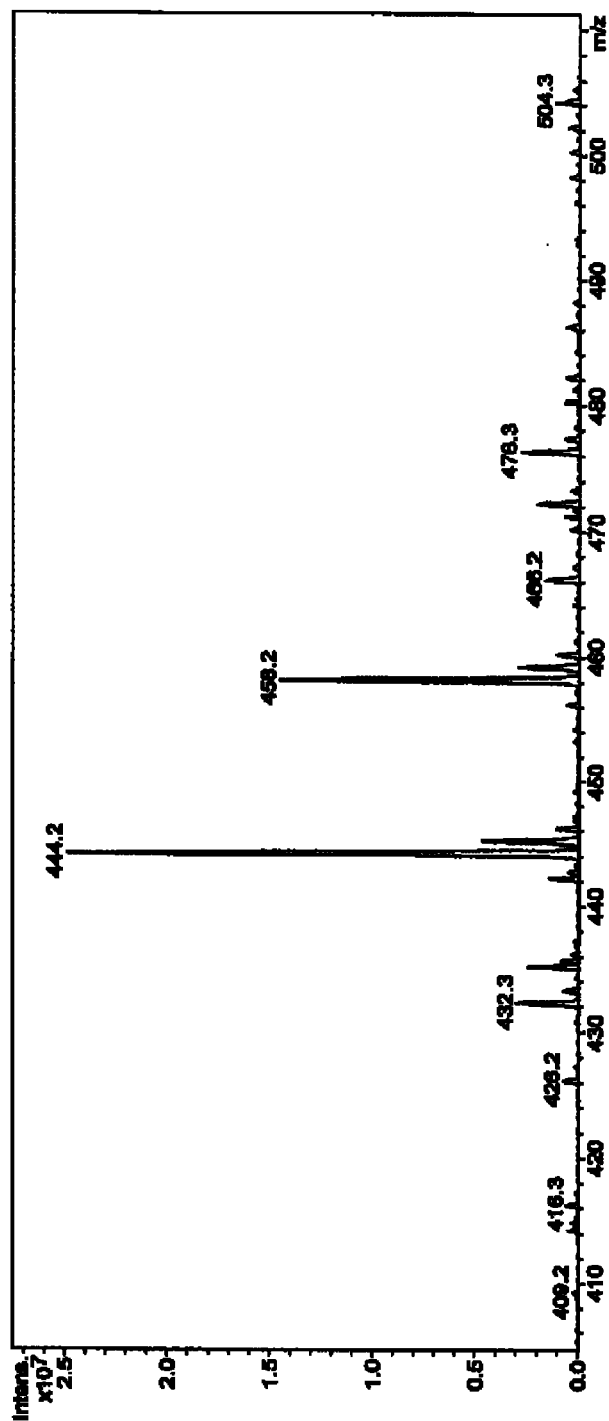
Figure 6B:
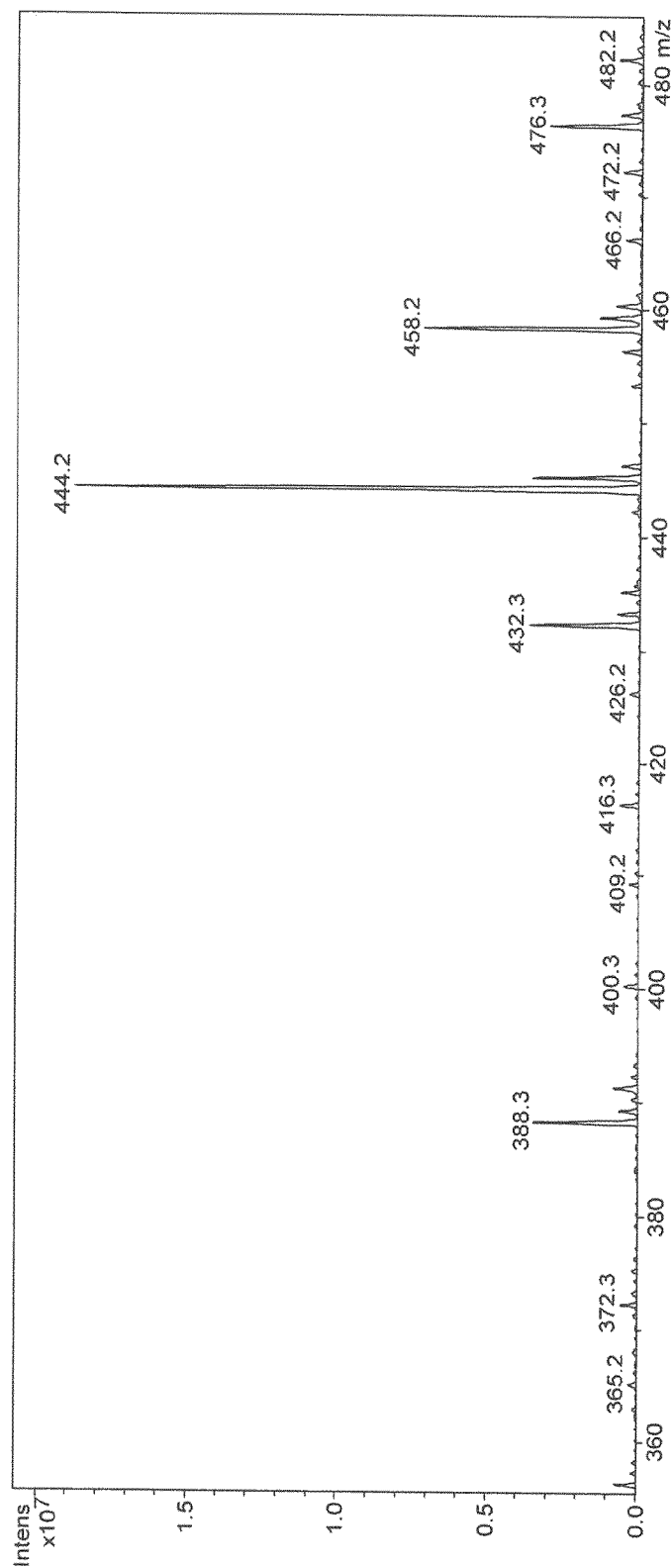

The present invention relates to glycoside-CF$_2$-serine or glycoside-CF$_2$-threonine derivatives, useful as glycoside-O-serine or glycoside-O-threonine mimics, as well as their preparation process, their use in peptide synthesis, said peptide and the use of said peptide.

Glycosylation is a co- or post-translational modification present in more than 50% of all proteins. O-glycosylation on the hydroxyl function of amino acids, such as serine, threonine, tyrosine, hydroxylysine or hydroxyproline, is the most common modification.

Glycoproteins, which are present in the cellular membranes, are implicated in numerous biochemical processes such as fertilisation, embryogenesis, neuronal development, immune responses, inflammatory reactions, intercellular recognition and regulation of the cell growth. Important changes are observed in the structure of sugars present on the surface of cells during the canceration process. Moreover, sugars of host cells are often used by different pathogens to allow their entry into cells.

For all these reasons, glycoproteins are an important key messengers for numerous therapies such as anti-inflammatory, antibacterial, antiviral and in particular anticancer therapies.

Cancer represents the first cause of mortality. In a global point of view, a doubling of the number of cancers is expected in the next 30 years. The discovery of novel anticancer compounds is thus a major endeavor.

Several treatments are actually used for treating cancer such as surgery, chemotherapy, radiotherapy or immunotherapy. However, the 3 first possibilities either are very invasive or lead to side effects such as, for chemotherapy, hair loss, nauseas, diarrheas and diminution of erythrocyte.

New approaches are thus studied to improve the treatments against cancer, notably through "passive" or "active" immunotherapy. The last one seems very promising and consists in the stimulation of the immune response against specific tumoral antigens.

Indeed, a modification of mucins expression has been observed on the surface of cancer cells. Those glycoproteins are over-expressed on the surface of tumoral epithelial cells.

Moreover, contrary to healthy cells, cancerous cells have, on their surface, because of abnormal glycosylations, shorter peptide units, which allowed the identification of specific tumoral antigens of saccharide type. Examples of oside epitopes are described below:

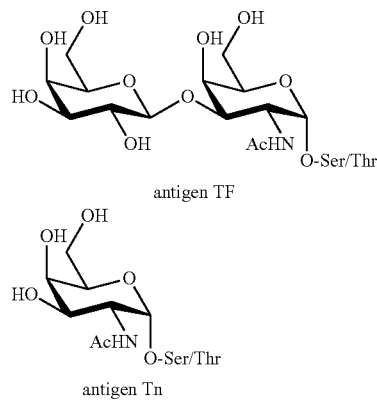

antigen TF antigen Tn

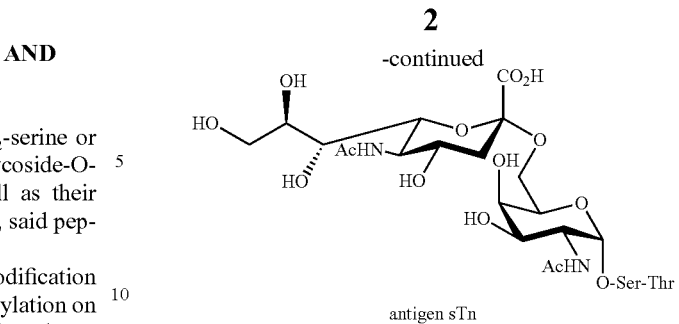

antigen sTn

The common synthon of these antigens is the moiety Gal-O-Ser/Thr. This moiety is currently being extensively studied towards the development of synthetic anticancer vaccines.

The drawback of such structures is the ease in which the O-glycosyl bond is cleaved by enzymatic systems such as hydrolases.

This prompted numerous research teams to design mimics of natural glycoconjugates in order to improve their stability in a biological medium. In this field, C-glycosides are the most studied, with the replacement of the oxygen atom of the O-glycosyl bond with a methylene group which is less sensitive to circulating enzymes. However, even if the stability is improved, the CH$_2$ group is not a good oxygen mimic, and access to this compound is not that straightforward.

The inventors of the present invention have thus developed a synthesis of glyco-CF$_2$-serine or glyco-CF$_2$-threonine derivatives which also constitute a synthetic challenge. Extensive synthetic methodology development was necessary to successfully synthesize the target compounds.

Indeed, a difluoromethylene moiety (—CF$_2$—) is a better mimic of an oxygen atom for electronic reasons. The CF$_2$ group has an electronegativity very closed to the one of the oxygen atom, the two fluorine atoms playing the role of the two electronic doublets of the oxygen. Moreover, the C—F bond is more stable thereby improving the stability of the final molecule. A CF$_2$ group is thus a better mimic of an oxygen atom than a CH$_2$ group.

The introduction of such glyco-CF$_2$-serine or glyco-CF$_2$-threonine derivatives in peptides or proteins moieties stabilizes the resulting glycopeptides or glycoproteins, notably against glycosidases, proteases and acid or basic conditions.

The present invention relates thus to a compound of formula (I):

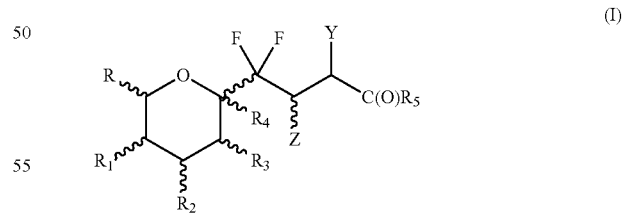

(I)

or a pharmaceutically acceptable salt thereof, a tautomer, a stereoisomer or a mixture of stereoisomers in any proportion, in particular a mixture of enantiomers, and particularly a racemate mixture,
wherein:
Y represents a CN, NO$_2$, NR$_6$R$_7$ or CH$_2$NR$_6$R$_7$ group,
Z represents H or CH$_3$,
R represents a hydrogen or fluorine atom or a CH$_3$, CH$_2$F, CH$_2$OSiR$^{a1}$R$^{b1}$R$^{c1}$, CH$_2$OR$_8$, CH$_2$OC(O)R$_9$, $CH_2OCO_2R_{10}$, $CH_2OC(O)NR_{11}R_{12}$, $CH_2OP(O)(OR_{13})_2$ or $CH_2OSO_3R_{14}$ group, $R_1$ and $R_2$ represent, independently from one another, a fluorine atom or an $OSiR^{a2}R^{b2}R^{c2}$, $OR_{15}$, $OC(O)R_{16}$, $OCO_2R_{17}$, $OC(O)NR_{18}R_{19}$, $OP(O)(OR_{20})_2$ or $OSO_3R_{21}$ group, $R_3$ represents a fluorine atom or an $OSiR^{a3}R^{b3}R^{c3}$, $OR_{22}$, $OC(O)R_{23}$, $OCO_2R_{24}$, $OCONR_{25}R_{26}$, $OP(O)(OR_{27})_2$, $OSO_3R_{28}$, $N_3$, phtalimidyl, $NR_{29}R_{30}$, $NR_{31}C(O)R_{32}$, $NR_{33}C(O)OR_{34}$, $N(C(O)R_{35})C(O)R_{36}$, $N(C(O)R_{37})C(O)OR_{38}$ and $N(C(O)OR_{39})C(O)OR_{40}$ group, $R_4$ represents a hydrogen or halogen atom or an $OSiR^{a4}R^{b4}R^{c4}$, $OR_{41}$, $OC(O)R_{42}$, $OCO_2R_{43}$, $OCONR_{44}R_{45}$, $OP(O)(OR_{46})_2$, or $OSO_3R_{47}$ group, or R and $R_1$, together with the carbon atoms carrying them, form a cyclic acetal having the following formula:

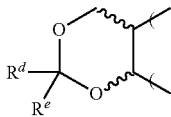

and/or ($R_1$ and $R_2$), ($R_2$ and $R_3$), and/or ($R_3$ and $R_4$), together with the carbon atoms carrying them, form a cyclic acetal having the following formula:

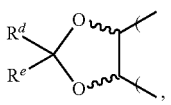

and $R_5$ represents a hydrogen or halogen atom or a $R_{48}$, $OR_{49}$ or $NR_{50}R_{51}$ group, with:

$R_6$ representing:
a hydrogen atom,
a $(C_1-C_6)$alkyl, $(C_2-C_6)$alkenyl, $(C_2-C_6)$alkynyl, $(C_3-C_7)$cycloalkyl, 5- to 7-membered heterocycloalkyl, aryl, heteroaryl, aryl-$(C_1-C_6)$alkyl, heteroaryl-$(C_1-C_6)$alkyl, $(C_1-C_6)$-alkyl-aryl or $(C_1-C_6)$-alkyl-heteroaryl group, this group being possibly substituted with one or more groups chosen among a halogen atom, OH, COOH and CHO; preferably a $(C_1-C_6)$alkyl, $(C_2-C_6)$alkenyl, $(C_2-C_6)$alkynyl, $(C_3-C_7)$cycloalkyl, 5- to 7-membered heterocycloalkyl, aryl-$(C_1-C_6)$alkyl, heteroaryl-$(C_1-C_6)$alkylgroup, this group being possibly substituted with one or more groups chosen among a halogen atom, OH, COOH and CHO,
a $C(O)R_{52}$ group, or
a $C(O)OR_{53}$ group, $R_7$ representing:
a hydrogen atom,
a $(C_1-C_6)$alkyl, $(C_2-C_6)$alkenyl, $(C_2-C_6)$alkynyl, $(C_3-C_7)$cycloalkyl, 5- to 7-membered heterocycloalkyl, aryl, heteroaryl, aryl-$(C_1-C_6)$alkyl, heteroaryl-$(C_1-C_6)$alkyl, $(C_1-C_6)$-alkyl-aryl or $(C_1-C_6)$-alkyl-heteroaryl group, this group being possibly substituted with one or more groups chosen among a halogen atom, OH, COOH and CHO; preferably a $(C_1-C_6)$alkyl, $(C_2-C_6)$alkenyl, $(C_2-C_6)$alkynyl, $(C_3-C_7)$cycloalkyl, 5- to 7-membered heterocycloalkyl, aryl-$(C_1-C_6)$alkyl, heteroaryl-$(C_1-C_6)$alkyl, group, this group being possibly substituted with one or more groups chosen among a halogen atom, OH, COOH and CHO,
a $C(O)R_{52}$ group,
a $C(O)OR_{53}$ group, or
a N-protecting group, $R_8$, $R_{15}$, $R_{22}$ and $R_{41}$ representing, independently from one another, a hydrogen atom, a O-protecting group or a $(C_1-C_6)$alkyl, $(C_2-C_6)$alkenyl, $(C_2-C_6)$alkynyl, $(C_3-C_7)$cycloalkyl, 5- to 7-membered heterocycloalkyl, aryl, heteroaryl, aryl-$(C_1-C_6)$alkyl, heteroaryl-$(C_1-C_6)$alkyl, $(C(C_1-C_6)$-alkyl-heteroaryl, saccharidic or polysaccharidic group, this group being possibly substituted with one or more groups chosen among a halogen atom, OH, COOH and CHO; and in particular a hydrogen atom, a $(C_1-C_6)$alkyl, aryl, aryl-$(C_1-C_6)$alkyl, saccharidic or polysaccharidic group, this group being possibly substituted with one or more groups chosen among a halogen atom, OH, COOH and CHO, $R_9$, $R_{10}$, $R_{16}$, $R_{17}$, $R_{23}$, $R_{24}$, $R_{32}$, $R_{34}$ to $R_{40}$, $R_{42}$, $R_{43}$, $R_{48}$, $R_{52}$ and $R_{53}$ representing, independently from one another, a $(C_1-C_6)$alkyl, $(C_2-C_6)$alkenyl, $(C_2-C_6)$alkynyl, $(C_3-C_7)$cycloalkyl, 5- to 7-membered heterocycloalkyl, aryl, heteroaryl, aryl-$(C_1-C_6)$alkyl, heteroaryl-$(C_1-C_6)$alkyl, $(C_1-C_6)$-alkyl-aryl or $(C_1-C_6)$-alkyl-heteroaryl group, this group being possibly substituted with one or more groups chosen among a halogen atom, OH, COOH and CHO; and in particular a $(C_1-C_6)$alkyl, aryl or aryl-$(C_1-C_6)$alkyl group, this group being possibly substituted with one or more groups chosen among a halogen atom, OH, COOH and CHO, $R_{11}$, $R_{12}$, $R_{18}$, $R_{19}$, $R_{25}$, $R_{26}$, $R_{29}$ to $R_{31}$, $R_{33}$, $R_{44}$, $R_{45}$, $R_{50}$ and $R_{51}$ representing, independently from one another, a hydrogen atom or a $(C_1-C_6)$alkyl, $(C_2-C_6)$alkenyl, $(C_2-C_6)$alkynyl, aryl, heteroaryl, aryl-$(C_1-C_6)$alkyl, heteroaryl-$(C_1-C_6)$alkyl, $(C_1-C_6)$-alkyl-aryl or $(C_1-C_6)$-alkyl-heteroaryl group, this group being possibly substituted with one or more groups chosen among a halogen atom, OH, COOH and CHO; advantageously a hydrogen atom or a $(C_1-C_6)$alkyl, $(C_2-C_6)$alkenyl, $(C_2-C_6)$alkynyl, aryl-$(C_1-C_6)$alkyl, heteroaryl-$(C_1-C_6)$alkylgroup, this group being possibly substituted with one or more groups chosen among a halogen atom, OH, COOH and CHO; and in particular a hydrogen atom or a $(C_1-C_6)$alkyl, aryl or aryl-$(C_1-C_6)$alkyl group, this group being possibly substituted with one or more groups chosen among a halogen atom, OH, COOH and CHO, $R_{13}$, $R_{14}$, $R_{20}$, $R_{21}$, $R_{27}$, $R_{28}$, $R_{46}$ and $R_{47}$ representing, independently from one another, a hydrogen atom or a $(C_1-C_6)$alkyl group, $R_{49}$ representing:
a hydrogen atom,
a $(C_1-C_6)$alkyl, $(C_2-C_6)$alkenyl, $(C_2-C_6)$alkynyl, $(C_3-C_7)$cycloalkyl, 5- to 7-membered heterocycloalkyl, aryl, heteroaryl, aryl-$(C_1-C_6)$alkyl, heteroaryl-$(C_1-C_6)$alkyl, $(C_1-C_6)$-alkyl-aryl or $(C_1-C_6)$-alkyl-heteroaryl group, this group being possibly substituted with one or more groups chosen among an halogen atom, OH, COOH and CHO, or
a O-protecting group, $R^{a1}$ to $R^{a4}$, $R^{b1}$ to $R^{b4}$ and $R^{c1}$ to $R^{c4}$ representing, independently from one another, a $(C_1-C_6)$alkyl, aryl or aryl-$(C_1-C_6)$alkyl group, and $R^d$ and $R^e$ representing, independently from one another, a hydrogen atom or a $(C_1-C_6)$alkyl group.

For the purpose of the invention, the term "pharmaceutically acceptable" is intended to mean what is useful to the preparation of a pharmaceutical composition, and what is generally safe and non toxic, for a pharmaceutical use.

The term <<pharmaceutically acceptable salt>> is intended to mean, in the framework of the present invention, a salt of a compound which is pharmaceutically acceptable, as defined above, and which possesses the pharmacological activity of the corresponding compound. Such salts comprise:

(1) hydrates and solvates, (2) acid addition salts formed with inorganic acids such as hydrochloric, hydrobromic, sulfuric, nitric and phosphoric acid and the like; or formed with organic acids such as acetic, benzenesulfonic, fumaric, glucoheptonic, gluconic, glutamic, glycolic, hydroxynaphtoic, 2-hydroxyethanesulfonic, lactic, maleic, malic, mandelic, methanesulfonic, muconic, 2-naphtalenesulfonic, propionic, succinic, dibenzoyl-L-tartaric, tartaric, p-toluenesulfonic, trimethylacetic, and trifluoroacetic acid and the like, and (3) salts formed when an acid proton present in the compound is either replaced by a metal ion, such as an alkali metal ion, an alkaline-earth metal ion, or an aluminium ion; or coordinated with an organic or inorganic base. Acceptable organic bases comprise diethanolamine, ethanolamine, N-methylglucamine, triethanolamine, tromethamine and the like. Acceptable inorganic bases comprise aluminium hydroxide, calcium hydroxide, potassium hydroxide, sodium carbonate and sodium hydroxide.

For the purpose of this invention, "tautomer" is intended to designate the various tautomer forms that the sugar of compound (I) may assume, namely a pyranose (6-membered ring), furanose (5-membered ring) or linear (open form) form.

However, the compounds of the invention can assume various tautomer forms only when the radical $R_4$ represents an OH group, $R_1$ having also to represent an OH group in order that the compounds of the invention can be in the furanose form.

Thus, for example, in the galactose series, the compounds of the invention might appear under the following various forms:

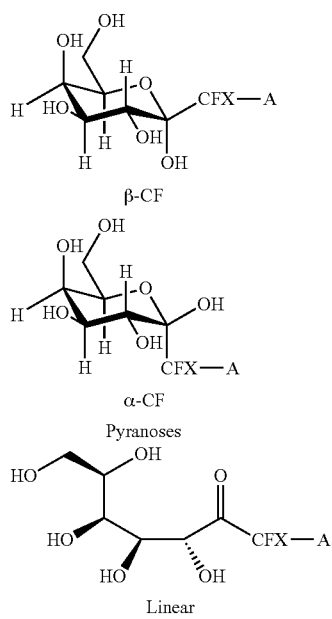

β-CF

α-CF

Pyranoses

Linear

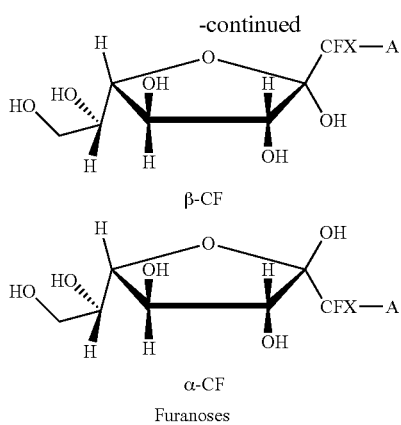

β-CF

α-CF

Furanoses

The anomeric carbon can appear in two different configurations in the closed pyranose and furanose forms.

The compounds of the invention can assume different tautomer forms which can be present in solution in equilibrium, with optionally a major tautomer form relatively to the other(s) tautomer form(s), or the compounds of the invention can assume only one tautomer form, such as only a furanose form, in some cases.

In this last case where the sugar assumes only one tautomer form, it is possible to block the configuration of the sugar in this tautomeric form when $R_4$=OH is transformed, notably by substitution of the OH group or conversion in a hydrogen or halogen atom.

Within the meaning of this invention, "stereoisomers" is intended to designate diastereoisomers or enantiomers. These are therefore optical isomers. Stereoisomers which are not mirror images of one another are thus designated as "diastereoisomers", and stereoisomers which are non-superimposable mirror images are designated as "enantiomers".

Notably, the sugar moiety of the compounds of the invention can belong to the D or L series, and preferably to the D series.

A carbon atom bond to four non-identical substituents is called a "chiral centre".

An equimolar mixture of two enantiomers is called a racemate mixture.

The term "halogen" as used in the present invention refers to an atom of fluorine, bromine, chlorine or iodine. Advantageously, this is an atom of fluorine.

The term "$(C_1-C_6)$-alkyl" as used in the present invention refers to a saturated, linear or branched hydrocarbon chain comprising from 1 to 6 carbon atoms, in particular the methyl, ethyl, n-propyl, isopropyl, n-butyl, iso-butyl, sec-butyl, tert-butyl, n-pentyl, n-hexyl groups.

The term "$(C_2-C_6)$-alkenyl" as used in the present invention refers to a linear or branched hydrocarbon chain comprising at least one double bond and comprising from 2 to 6 carbon atoms, e.g., such as an ethenyl (vinyl) or propenyl group.

The term "$(C_2-C_6)$-alkynyl" as used in the present invention refers to a linear or branched hydrocarbon chain comprising at least one triple bond and comprising from 2 to 6 carbon atoms, e.g., such as an ethynyl or propynyl group.

The term "$(C_3-C_7)$-cycloalkyl" as used in the present invention refers to a saturated hydrocarbon ring comprising from 3 to 7, advantageously from 5 to 7, carbon atoms, in particular the cyclohexyl, cyclopentyl or cycloheptyl group.

The term "heterocycloalkyl" as used in the present invention refers to a saturated hydrocarbon ring having 5 to 7 members and containing one or more, advantageously one or two, heteroatoms, e.g., such as sulphur, nitrogen or oxygen atoms, e.g., such as the tetrahydrofuranyl, piperidinyl, pyrrolidinyl, tetrahydropyranyl, 1,3-dioxolanyl group.

The term "aryl" as used in the present invention refers to an aromatic group preferably comprising from 5 to 10 carbon atoms and including one or more fused rings, e.g., such as a phenyl or naphtyl group. This is advantageously phenyl.

The term "heteroaryl" as used in the present invention refers to any aryl group as defined above wherein one or more carbon atoms have been replaced by one or more heteroatoms, advantageously 1 to 4, and even more advantageously 1 to 2, e.g., such as sulphur, nitrogen or oxygen atoms. Examples of heteroaryl groups are the furyl, thiophenyl, pyrrolyl, pyridyl, pyrimidyl, pyrazolyl, imidazolyl, tetrazolyl or else indyl groups.

The term "aryl-$(C_1$-$C_6)$-alkyl" as used in the present invention refers to any aryl group as defined above, which is bound to the molecule by means of a $(C_1$-$C_6)$-alkyl group as defined above. In particular, a group such as this can be a benzyl group.

The term "heteroaryl-$(C_1$-$C_6)$-alkyl" as used in the present invention refers to mean a heteroaryl group as defined above, which is bound to the molecule by means of a $(C_1$-$C_6)$-alkyl group as defined above.

The term "$(C_1$-$C_6)$-alkyl-aryl" as used in the present invention refers to a $(C_1$-$C_6)$-alkyl group as defined above, which is bound to the molecule by means of an aryl group as defined above. In particular, a group such as this can be a methylphenyl group.

The term "$(C_1$-$C_6)$-alkyl-heteroaryl" as used in the present invention refers to a $(C_1$-$C_6)$-alkyl group as defined above, which is bound to the molecule by means of a heteroaryl group as defined above.

The term "N-protecting group" as used in the present invention refers to those groups intended to protect an amino group against undesirable reactions during synthetic procedures. Commonly used N-protecting groups are disclosed in Greene, "Protective Groups In Organic Synthesis", (John Wiley & Sons, New York (1981)). N-protecting groups comprise carbamates, amides, N-alkyl derivatives, amino acetal derivatives, N-benzyl derivatives, imine derivatives, enamine derivatives and N-heteroatom derivatives. In particular, N-protecting groups include formyl, acetyl, benzoyl, pivaloyl, phenylsulfonyl, benzyl (Bn), t-butyloxycarbonyl (Boc), benzyloxycarbonyl (Cbz), trichloroethoxycarbonyl (TROC), allyloxycarbonyl (Alloc), fluorenylmethyloxycarbonyl (FMOC), and the like. In particular, it will be a t-butyloxycarbonyl, benzyloxycarbonyl or fluorenylmethyloxycarbonyl group.

The term "O-Protecting group" as used in the present invention refers to a substituent which protects hydroxyl groups against undesirable reactions during synthetic procedures such as those O-protecting groups disclosed in Greene, "Protective Groups In Organic synthesis", (John Wiley & Sons, New York (1981)). O-protecting groups comprise ($C_1$-$C_6$)alkyl groups, such as methyl, ethyl, tert-butyl; substituted methyl ethers, for example, methoxymethyl (MOM), benzyloxymethyl, 2-methoxyethoxymethyl, 2-(trimethylsilyl) ethoxymethyl, benzyl and triphenylmethyl; tetrahydropyranyl ethers; substituted ethyl ethers, for example, 2,2,2-trichloroethyl; and silyl ethers, for example, trimethylsilyl, t-butyldimethylsilyl (TBS) and t-butyldiphenylsilyl. In particular, it will be a benzyl or methoxymethyl group.

The term "saccharide" as used in the present invention refers to erythrose, threose, ribose, arabinose, xylose, lyxose, allose, altrose, glucose, mannose, gulose, idose, galactose, talose, erythrulose, ribulose, xylulose, psicose, fructose, sorbose or tagatose, in D or L form.

The term "saccharidic group" as used in the present invention refers to a saccharide as defined above bond to the molecule by means of its oxygen atom present at the anomeric centre.

The term "polysaccharide" as used in the present invention refers to a chain comprising at least 2, and preferably 2 to 10 saccharides as defined above bound together by means of an oxygen bridge formed between the OH function at the anomeric position of a saccharide and the OH function not at the anomeric position of another saccharide.

The term "polysaccharidic group" as used in the present invention refers to a polysaccharide as defined above bond to the molecule by means of the oxygen atom present at the anomeric centre of the terminal saccharide.

The compounds of the invention are advantageously based on the following formulas (Iα) and (Iβ):

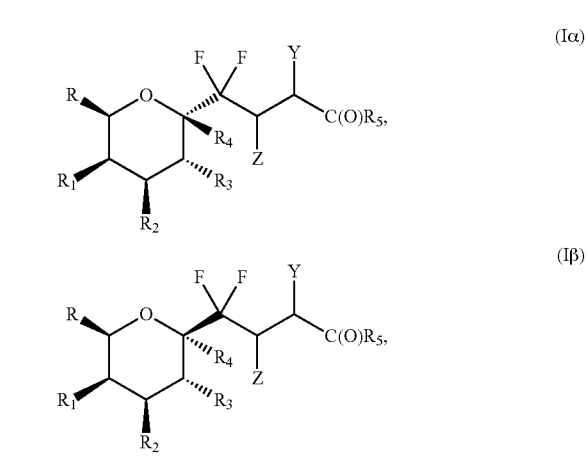

with R, $R_1$, $R_2$, $R_3$, $R_4$, $R_5$, Z and Y as defined above.

R can represent a $CH_2OSiR^{a1}R^{b1}R^{c1}$, $CH_2OR_8$, $CH_2OC(O)R_9$, $CH_2OCO_2R_{10}$, $CH_2OC(O)NR_{11}R_{12}$, $CH_2OP(O)(OR_{13})_2$ or $CH_2OSO_3R_{14}$ group, advantageously a $CH_2OSiR^{a1}R^{b1}R^{c1}$, $CH_2OR_8$ or $CH_2OC(O)R_9$ group, more advantageously a $CH_2OR_8$ or $CH_2OC(O)R_9$ group, and even more advantageously a $CH_2OR_8$ group.

R can represent in particular a $CH_2OR_8$ group with $R_9$ representing a hydrogen atom, a O-protecting group or a $(C_1$-$C_6)$-alkyl, aryl or aryl-$(C_1$-$C_6)$-alkyl group; or a $CH_2OC(O)R_9$ group with $R_9$ representing a $(C_1$-$C_6)$-alkyl, aryl or aryl-$(C_1$-$C_6)$-alkyl group.

R can represent more particularly a $CH_2OR_8$ group with $R_9$ representing a hydrogen atom or a O-protecting group. For instance, R can represent a $CH_2OH$ or $CH_2OBn$ group.

$R_1$ and $R_2$ can represent, independently from one another, an $OSiR^{a2}R^{b2}R^{c2}$, $OR_{15}$, $OC(O)R_{16}$, $OCO_2R_{17}$ or $OC(O)NR_{18}R_{19}$ group, advantageously an $OSiR^{a2}R^{b2}R^{c2}$, $OR_{15}$ or $OC(O)R_{16}$ group, more advantageously an $OR_{15}$ or $OC(O)R_{16}$ group, and even more advantageously an $OR_{15}$ group.

$R_1$ and $R_2$ can represent in particular, independently from one another, an $OR_{15}$ group with $R_{15}$ representing a hydrogen atom, a O-protecting group or a $(C_1$-$C_6)$-alkyl, aryl or aryl-$(C_1$-$C_6)$-alkyl group; or an $OC(O)R_{16}$ group $R_{16}$ representing a $(C_1$-$C_6)$-alkyl, aryl or aryl-$(C_1$-$C_6)$-alkyl group.

$R_1$ and $R_2$ can represent more particularly, independently from one another, an $OR_{15}$ group with $R_{15}$ representing a hydrogen atom or a O-protecting group. For instance, $R_1$ and $R_2$ can represent an OH or OBn group.

Preferably, $R_1$ and $R_2$ are identical, and represent notably an OH or OBn group.

In particular, R represents a $CH_2OR_8$ group and $R_1$ and $R_2$ represent, independently from one another, an $OR_{15}$ group, $R_8$ and $R_{15}$ representing advantageously a hydrogen atom or an O-protecting group. $R_8$ and the two $R_{15}$ can be identical, such as H or an O-protecting group.

According to another particular embodiment, $R=CH_2OH$ and $R_1=R_2=OH$ or $R=CH_2OBn$ and $R_1=R_2=OBn$.

According to a first embodiment, $R_3$ represent an $OSiR^{a3}R^{b3}R^{c3}$, $OR_{22}$, $OC(O)R_{23}$, $OCO_2R_{24}$, $OCONR_{25}R_{26}$, $NR_{29}R_{30}$, $NR_{31}C(O)R_{32}$, $NR_{33}C(O)OR_{34}$, $N(C(O)R_{35})C(O)R_{36}$, $N(C(O)R_{37})C(O)OR_{38}$ or $N(C(O)OR_{39})C(O)OR_{40}$ group, advantageously an $OSiR^{a3}R^{b3}R^{c3}$, $OR_{22}$, $OC(O)R_{23}$, $NR_{29}R_{30}$, $NR_{31}C(O)R_{32}$ or $NR_{33}C(O)OR_{34}$ group, more advantageously an $OR_{22}$, $OC(O)R_{23}$ or $NR_{31}C(O)R_{32}$ group, and even more advantageously an $OR_{22}$ or $NR_{31}C(O)R_{32}$ group.

$R_3$ can represent in particular an $OR_{22}$ group with $R_{22}$ representing a hydrogen atom, a O-protecting group or a $(C_1-C_6)$-alkyl, aryl or aryl-$(C_1-C_6)$-alkyl group; an $OC(O)R_{23}$ group with $R_{23}$ representing a $(C_1-C_6)$-alkyl, aryl or aryl-$(C_1-C_6)$-alkyl group; or a $NR_{31}C(O)R_{32}$ group with $R_{31}$ representing a hydrogen atom or a $(C_1-C_6)$-alkyl, aryl or aryl-$(C_1-C_6)$-alkyl group and $R_{32}$ representing a $(C_1-C_6)$alkyl, aryl or aryl-$(C_1-C_6)$alkyl group.

$R_3$ can represent more particularly an $OR_{22}$ group with $R_{22}$ representing a hydrogen atom or a O-protecting group; or a $NR_{31}C(O)R_{32}$ group with $R_{31}$ representing a hydrogen atom and $R_{32}$ representing a $(C_1-C_6)$alkyl. For instance, $R_3$ can represent an OH, OBn, OMOM or NHAc group.

According to a second embodiment $R_3$ can represent an $OSiR^{a3}R^{b3}R^{c3}$, $OR_{22}$, $OC(O)R_{23}$, $OCO_2R_{24}$ or $OCONR_{25}R_{26}$ group, advantageously an $OSiR^{a3}R^{b3}R^{c3}$, $OR_{22}$ or $OC(O)R_{23}$ group, more advantageously an $OR_{22}$ or $OC(O)R_{23}$ group, and even more advantageously an $OR_{22}$ group.

$R_3$ can represent in particular an $OR_{22}$ group with $R_{22}$ representing a hydrogen atom, a O-protecting group or a $(C_1-C_6)$-alkyl, aryl or aryl-$(C_1-C_6)$-alkyl group; or an $OC(O)R_{23}$ group $R_{23}$ with representing a $(C_1-C_6)$-alkyl, aryl or aryl-$(C_1-C_6)$-alkyl group.

$R_3$ can represent more particularly an $OR_{22}$ group with $R_{22}$ representing a hydrogen atom or a O-protecting group. For instance, $R_3$ can represent an OH, OBn or OMOM group.

According to a particular embodiment, $R_1$, $R_2$ and $R_3$ are identical.

According to another particular embodiment, R represents a $CH_2OR_8$ group; $R_1$ and $R_2$ represent, independently from one another, an $OR_{15}$ group; and $R_3$ represents an $OR_{22}$ group, $R_8$, $R_{15}$ and $R_{22}$ representing advantageously a hydrogen atom or an O-protecting group. $R_8$ and the two $R_{15}$ can be identical, such as H or an O-protecting group. $R_8$, the two $R_{15}$ and $R_{22}$ can also be identical, such as H or an O-protecting group.

According to another particular embodiment, $R=CH_2OH$, $R_1=R_2=OH$ or $R_1=R_2=R_3=OH$.

$R_4$ can advantageously represent a hydrogen or halogen atom or an $OR_{41}$ group, and in particular a hydrogen atom or an $OR_{41}$ group.

Yet even more advantageously, $R_4$ may represent a hydrogen or halogen atom or an OH, O-protecting, —O—$(C_1-C_6)$-alkyl, —O-aryl and —O—$(C_1-C_6)$-alkyl-aryl group, and in particular, a hydrogen atom or an OH, O-protecting, —O—$(C_1-C_6)$-alkyl, —O-aryl and —O—$(C_1-C_6)$-alkyl-aryl group.

$R_4$ can also represent a hydrogen or halogen atom or an OH, —O—$(C_1-C_6)$-alkyl, —O-aryl and —O—$(C_1-C_6)$-alkyl-aryl group, and in particular, a hydrogen atom or an OH, —O—$(C_1-C_6)$-alkyl, —O-aryl and —O—$(C_1-C_6)$-alkyl-aryl group.

In particular, $R_4$ can represent a hydrogen or halogen (such as Br, Cl, F) atom or an OH or O-protecting group, and advantageously, a hydrogen atom or an OH or O-protecting group, such as H, OH or OBn.

$R_4$ can also represent a hydrogen or halogen (such as Br, Cl, F) atom or an OH group, such as H or OH.

According to a particular embodiment, $R_4$ represents a hydrogen atom.

According to a first embodiment, Y represents a $NO_2$ or $NR_6R_7$ group, and notably a $NR_6R_7$ group, with $R_6$ and $R_7$ as defined previously and notably with $R_6$ representing a hydrogen atom or a $(C_1-C_6)$alkyl group and $R_7$ representing:
  a hydrogen atom,
  a $(C_1-C_6)$alkyl, aryl or aryl-$(C_1-C_6)$alkyl group; in particular a $(C_1-C_6)$alkyl or aryl-$(C_1-C_6)$alkyl group,
  a $C(O)R_{52}$ group, with $R_{52}$ as defined above and representing in particular a $(C_1-C_6)$alkyl, aryl or aryl-$(C_1-C_6)$alkyl group,
  a $C(O)OR_{53}$ group, with $R_{53}$ as defined above and representing in particular a $(C_1-C_6)$alkyl, aryl or aryl-$(C_1-C_6)$alkyl group, or
  a N-protecting group.

According to a second embodiment, Y represents a CN or $CH_2NR_6R_7$ group, and notably a $CH_2NR_6R_7$ group, with $R_6$ and $R_7$ as defined previously and notably with $R_6$ representing a hydrogen atom or a $(C_1-C_6)$alkyl group and $R_7$ representing:
  a hydrogen atom,
  a $(C_1-C_6)$alkyl, aryl or aryl-$(C_1-C_6)$alkyl group; in particular a $(C_1-C_6)$alkyl or aryl-$(C_1-C_6)$alkyl group,
  a $C(O)R_{52}$ group, with $R_{52}$ as defined above and representing in particular a $(C_1-C_6)$alkyl, aryl or aryl-$(C_1-C_6)$alkyl group,
  a $C(O)OR_{53}$ group, with $R_{53}$ as defined above and representing in particular a $(C_1-C_6)$alkyl, aryl or aryl-$(C_1-C_6)$alkyl group, or
  a N-protecting group.

$R_5$ represents advantageously an $OR_{49}$ group, with $R_{49}$ as defined previously and advantageously representing a hydrogen atom, a $(C_1-C_6)$alkyl group or a O-protecting group.

According to a particular embodiment (compounds of formula (I-1)), Y represents a $NR_6R_7$ or $CH_2NR_6R_7$ group, and notably a $NR_6R_7$ group, and $R_5$ represents an $OR_{49}$ group, with:
  $R_6$ and $R_7$ representing each a hydrogen atom and $R_{49}$ representing a O-protecting group such as a $(C_1-C_6)$ alkyl group, or
  $R_{49}$ and $R_6$ representing each a hydrogen atom and $R_7$ representing a N-protecting group such as a Boc, Cbz or FMOC group.

In this case, R represents preferably a $CH_2OR_8$ group with $R_8$ representing a O-protecting group; $R_1$ and $R_2$ represent preferably, independently from one another, an $OR_{15}$ group with $R_{15}$ representing a O-protecting group; and $R_3$ represents preferably an $OR_{22}$ group with $R_{22}$ representing a O-protecting group or a $NR_{31}C(O)R_{32}$ group with $R_{31}$ representing a hydrogen atom and $R_{32}$ representing a $(C_1-C_6)$alkyl, and notably $R_3$ represents an $OR_{22}$ group.

$R_4$ can represent a hydrogen atom or an $OR_{41}$ group with $R_{41}$ representing a O-protecting group, and notably $R_4$ can represent a hydrogen atom.

According to a particular embodiment of the present invention, the compound of formula (I) can be chosen among:

11
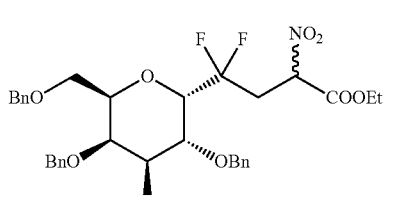
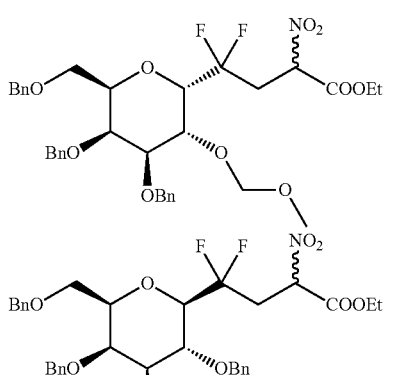
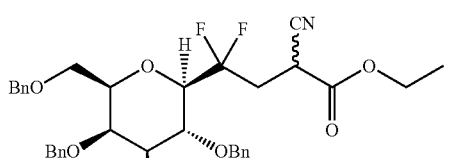
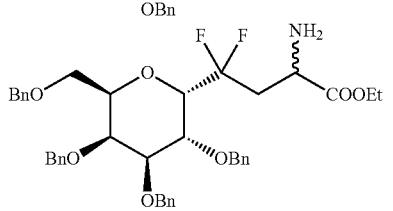
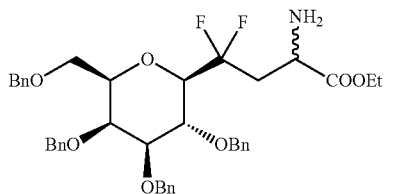
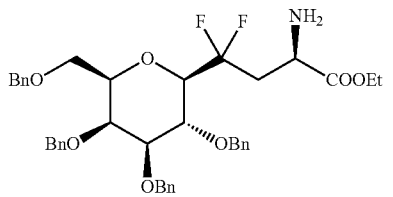
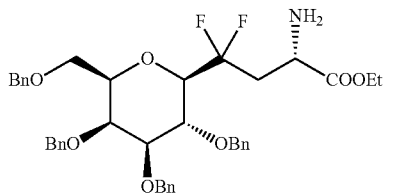
12
-continued
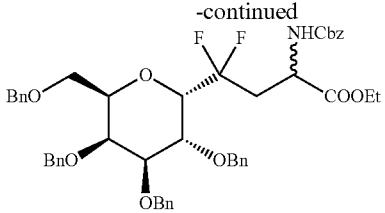
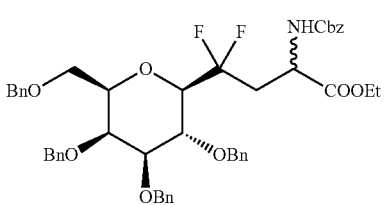
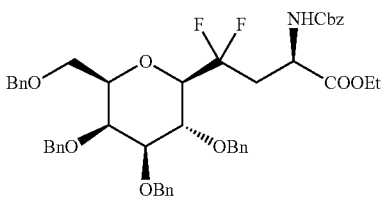
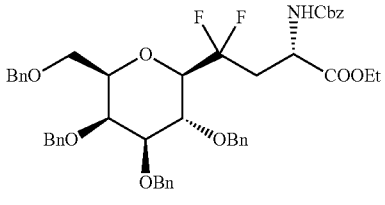
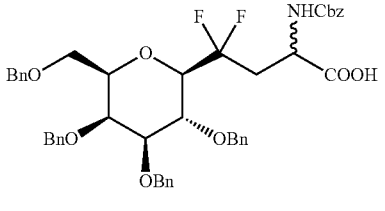
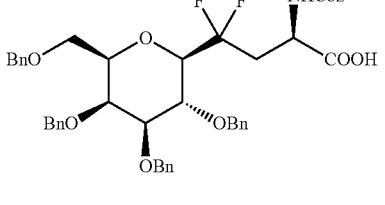
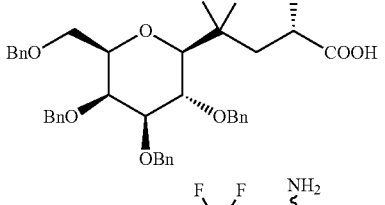
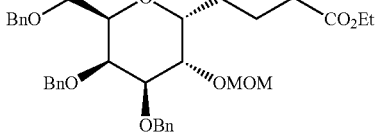

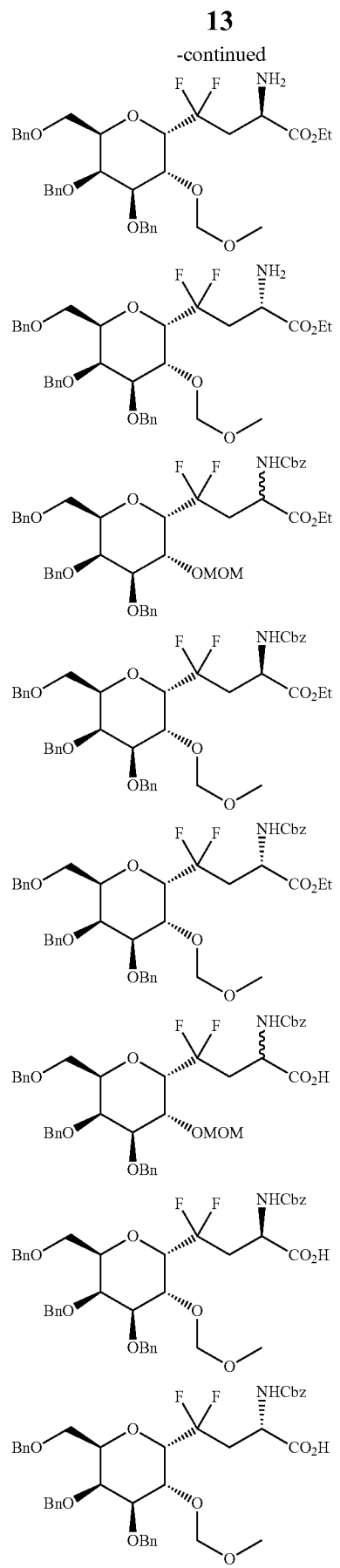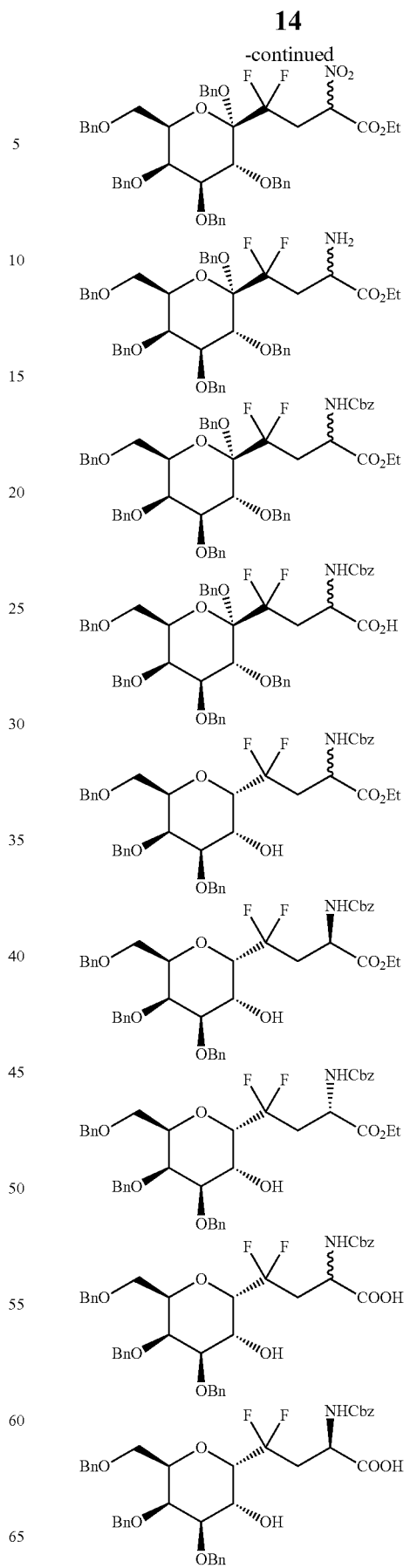

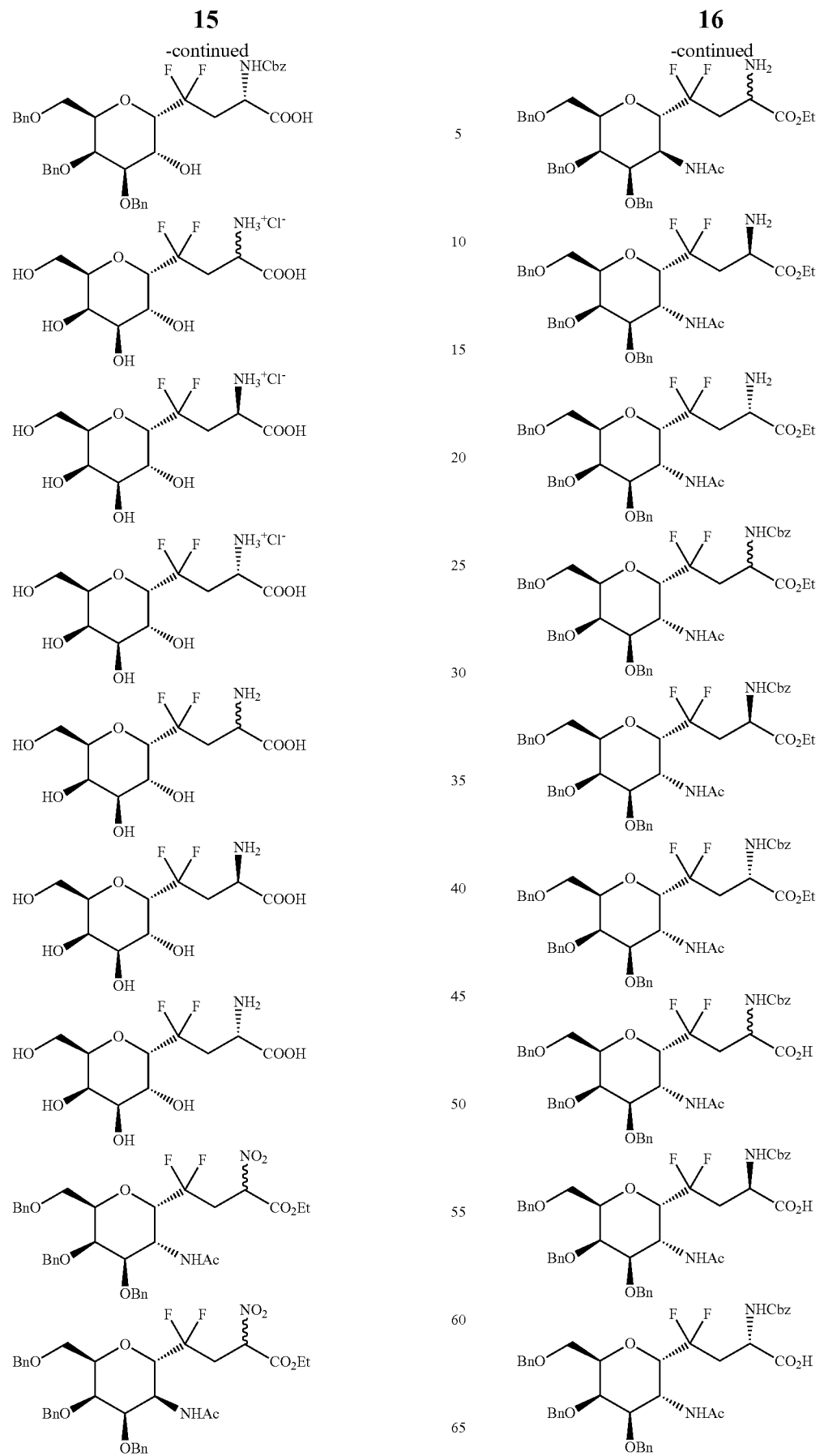

-continued

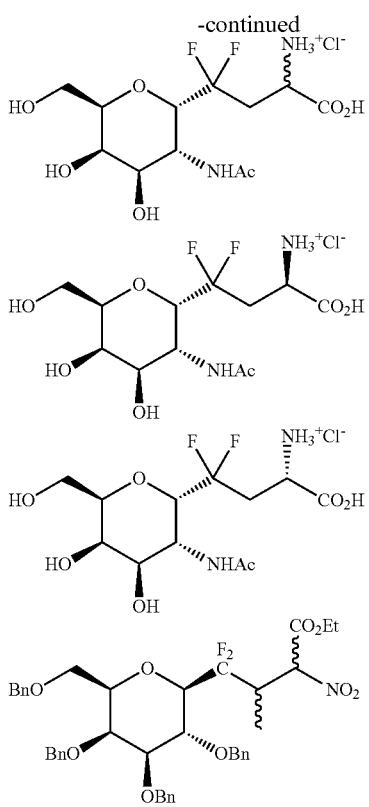

The present invention relates also to a process for preparing a compound of formula (I) as defined above with Z=H, comprising the following successive steps:
i) dehydration of a compound of formula (II):

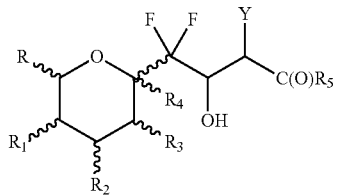

(II)

in which R, $R_1$, $R_2$, $R_3$, $R_4$, $R_5$ and Y are as defined above,
to give a compound of formula (III):

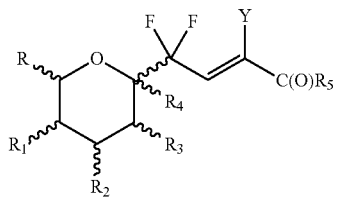

(III)

in which R, $R_1$, $R_2$, $R_3$, $R_4$, $R_5$ and Y are as defined above, and
ii) hydrogenation of the compound of formula (III) obtained in the previous step to give a compound of formula (I) with Z=H.

Step a):
This step can be carried out by transforming the hydroxy function in a leaving group such as a halogen atom, a sulfate (—OS(O)$_2$O-A$_1$), a sulfonate (—OS(O)O-A$_1$) or a carboxylate (—OC(O)-A$_1$), with A$_1$ representing a (C$_1$-C$_6$)alkyl, aryl, (C$_1$-C$_6$)alkyl-aryl or aryl-(C$_1$-C$_6$)alkyl group, said group being optionally substituted with one or more fluorine atoms. Such a leaving group can be, for example, a mesylate (—OSO$_2$Me), a tosylate (—OSO$_2$-PhMe), a triflate (—OSO$_2$CF$_3$) or an acetate (—OC(O)CH$_3$).

The leaving group is then eliminated in the presence of a base such as triethylamine.

For instance, this step can be carried out in the presence of mesyl chloride (MsCl) and a base such as triethylamine.

The elimination step can also be carried out directly from the hydroxy function, i.e. without transforming it first in a leaving group, by reaction with Burgess' reactive or with Martins' persulfane.

Step b):
This step can be carried out by hydrogenation methods well known to the person skilled in the art, notably in the presence of a hydride donor such as a borohydride, notably NaBH$_4$, or by a radical reaction in the presence of Bu$_3$SnH.

The compound thus obtained can be separated from the reaction medium by methods well known to the person skilled in the art, such as by extraction, evaporation of the solvent or by precipitation or crystallisation (followed by filtration).

The compound can be also purified if necessary by methods well known to the person skilled in the art, such as by recrystallisation, chromatography on a column of silica gel or high performance liquid chromatography (HPLC).

According to a first embodiment of the invention, this process can be carried out with a compound of formula (IIa1), which is a compound of formula (II) in which Y=NO$_2$. The compound of formula (Ia1) obtained, i.e. a compound of formula (I) in which Z=H and Y=NO$_2$, can be then hydrogenated to give a compound of formula (Ib1), i.e. a compound of formula (I) in which Z=H and Y=NH$_2$. Compounds of formula (Ic1), i.e. compounds of formula (I) in which Z=H and Y=NR$_6$R$_7$, at least R$_6$ or R$_7$ being not a hydrogen atom, are then obtained by substitution of the amino group of a compound of formula (Ib1).

According to a second embodiment of the invention, this process can be carried out with a compound of formula (IIa2), which is a compound of formula (II) in which Y=CN. The compound of formula (Ia2) obtained, i.e. a compound of formula (I) in which Z=H and Y=CN, can be then hydrogenated or reduced to give a compound of formula (Ib2), i.e. a compound of formula (I) in which Z=H and Y=CH$_2$NH$_2$. However, the compound of formula (Ib2) can be also obtained directly in one step from the compound of formula (IIIa2), corresponding to a compound of formula (III) in which Z=H and Y=CN. Compounds of formula (Ic2), i.e. compounds of formula (I) in which Z=H and Y=CH$_2$NR$_6$R$_7$, at least R$_6$ or R$_7$ being not a hydrogen atom, are then obtained by substitution of the amino group of a compound of formula (Ib2).

Thus, according to a particular embodiment, the process comprises the following successive steps:
a1) dehydration of a compound of formula (IIa) corresponding to a compound of formula (II) in which Y=NO$_2$ or CN to give a compound of formula (Ma) corresponding to a compound of formula (III) in which Y=NO$_2$ or CN,
b1) reduction of the compound of formula (Ma) obtained in the previous step to give a compound of formula (Ia) corresponding to a compound of formula (I) in which Z=H and Y=NO$_2$ or CN, or a compound of formula (Ib)

corresponding to a compound of formula (I) in which Z=H and Y=NH$_2$ or CH$_2$NH$_2$, c1) optionally reduction of the NO$_2$ or CN function of the compound of formula (Ia) obtained in the previous step to give a compound of formula (Ib) as defined in step b1), and d1) optionally substitution of the amino function of the compound of formula (Ib) obtained in the previous step to give a compound of formula (Ic) corresponding to a compound of formula (I) in which Z=H and Y=NR$_6$R$_7$ or CH$_2$NR$_6$R$_7$ respectively, with at least R$_6$ or R$_7$ being not a hydrogen atom.

Step a1): See Step a).

It is to be noted that the compound of formula (IIa) can be obtained by reaction of a compound of formula (IV):

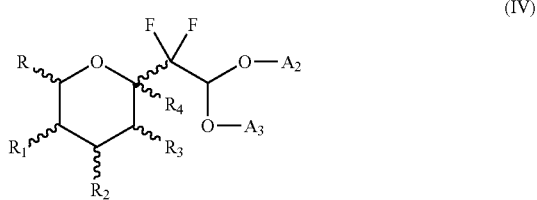

in which R, R$_1$, R$_2$, R$_3$ and R$_4$ are as defined above and A$_2$ and A$_3$ represent, independently from one another, a hydrogen atom or a (C$_1$-C$_6$)alkyl or aryl-(C$_1$-C$_6$)-alkyl group, with a compound of formula (V)

Y—CH$_2$—COR$_5$ (V)

in which R$_5$ is as defined previously and Y=NO$_2$ or CN, in the presence of a base such as HNEt$_2$.

This reaction is carried out in the Henry's conditions.

The compound of formula (IV) can be obtained by methods well known to the person skilled in the art (see for example the experimental part).

Preferably, R$_5$ represents a R$_{48}$ or OR$_{49}$ group, with R$_{48}$ and R$_{49}$ as defined above but with the proviso that R$_{49}$ is not a hydrogen atom.

Step b1): See Step b).

Step c1):

This step can be carried out by methods well known to the person skilled in the art.

Notably, this step can be carried out under a hydrogen atmosphere in the presence of a hydrogenation catalyst, at an atmospheric pressure or at a higher pressure. The catalyst can be based on palladium, nickel or platinum, such as palladium on carbon (Pd/C), Raney's nickel or PtO$_2$. The reaction can be carried out in the presence of an acid or a base to activate the catalyst.

The reduction of the nitro function can be carried out also in the presence of a borohydride, such as NaBH$_4$, and a salt of nickel, cobalt, palladium, tin, copper or lanthanide, e.g. NiCl$_2$, TiCl$_4$, or CoCl$_2$.

Another method consists in the hydrogenation of the nitro function with hydrogen formed in situ by the action of an acid, such as HCl, AcOH, Me$_3$SiCl, CF$_3$COOH or HCO$_2$H, on a metal chosen among zinc, tin and iron.

The nitro function can also be reduced in an oxime (=N—OH) which is then reduced in an amino group. This method is well known to the person skilled in the art.

The reduction of the nitro functionality into an oxime group can be obtained in the presence of a metal salt such as a tin salt (e.g. SnCl$_2$ or Sn(Ph)$_2$), associated or not to Et$_3$N/PhSH or TMSPhSH/Et$_3$N. NaNO$_2$ can also be used in the presence of a proton source such as CH$_3$COOH or H$_2$O in DMSO to reduce the nitro function. These reactions can be carried out at a temperature between 65 and 100° C.

The oxime can then be reduced into an amino function under a hydrogen atmosphere in the presence of a hydrogenation catalyst, at an atmospheric pressure or at a higher pressure. The catalyst can be based on palladium, nickel, platinum, ruthenium, rhodium or iridium, such as palladium on carbon (Pd/C), Pd(OH)$_2$, Pd on graphite, Raney's nickel, PtO$_2$, RuCl$_3$ or IrCl$_3$. The reaction can be carried out in the presence of an acid or a base to activate the catalyst.

This reduction can also be carried out in the presence of an aluminum amalgam prepared from aluminum and HgCl$_2$. The oxime can also be reduced with hydrogen formed in situ by the action of an acid on a metal. Hydrides can also be used, such as NaBH$_4$ or LiAlH$_4$.

All these methods are well known to the person skilled in the art. However, other methods known to the person skilled in the art can be used.

Step d1):

The substitution of the amino function can be carried out by methods well known to the person skilled in the art.

The compound thus obtained can be separated from the reaction medium by methods well known to the person skilled in the art, such as by extraction, evaporation of the solvent or by precipitation or crystallisation (followed by filtration).

The compound can also be purified if necessary by methods well known to the person skilled in the art, such as by recrystallisation, chromatography on a column of silica gel or high performance liquid chromatography (HPLC).

The present invention relates also to a process for preparing a compound of formula (I) as defined above with Z=CH$_3$, comprising the following successive steps:

i) reaction of a compound of formula (VII):

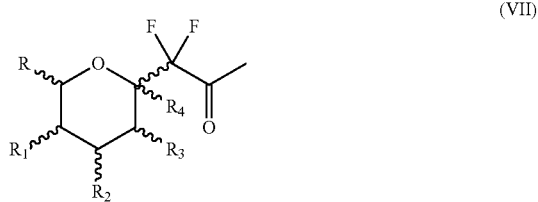

in which R, R$_1$, R$_2$, R$_3$ and R$_4$ are as defined above, with a compound of formula (V):

Y—CH$_2$—COR$_5$ (V)

in which R$_5$ is as defined previously and Y=NO$_2$ or CN, to give a compound of formula (VIII):

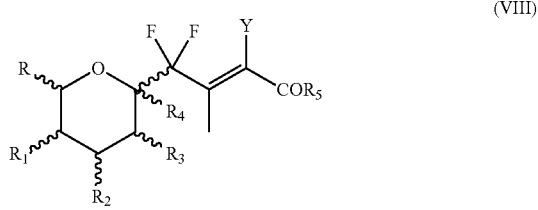

ii) in which R, R$_1$, R$_2$, R$_3$, R$_4$ and R$_5$ are as defined above and Y=NO$_2$ or CN, optionally reduction of the compound of formula (VIII) obtained in the previous step i) to give a compound of formula (I) with Z=CH$_3$ and Y=NO$_2$ or CN, iii) optionally reduction of the NO$_2$ or CN function of the compound of formula (I) obtained in the previous step ii) to give a compound of formula (I) with Z=CH$_3$ and Y=NH$_2$ or CH$_2$NH$_2$, and iv) optionally substitution of the amino function of the compound of formula (I) obtained in the previous step iii) to give a compound of formula (I) with Z=CH$_3$ and Y=NR$_6$R$_7$ or CH$_2$NR$_6$R$_7$, with at least R$_6$ or R$_7$ being not a hydrogen atom.

Step i):

This reaction can be carried out in the presence of a Lewis acid such as TiCl$_4$ and a base such as N-methyl-morpholine (NMM). Tetrahydrofurane, dichloromethane or a mixture thereof can be used as solvent.

The compounds of formula (VII) can be prepared as described in the experimental part below.

Step ii): See Step b1).

Step iii): See Step c1).

Step iv): See Step d1).

The compound thus obtained can be separated from the reaction medium by methods well known to the person skilled in the art, such as by extraction, evaporation of the solvent or by precipitation or crystallisation (followed by filtration).

The compound can be also purified if necessary by methods well known to the person skilled in the art, such as by recrystallisation, chromatography on a column of silica gel or high performance liquid chromatography (HPLC).

If the two processes described above, to prepare compounds of formula (I) with Z=H or CH$_3$ respectively, are carried out from a compound of formula (II) or (VII) with R$_5$ representing a OR$_{49}$ group, with R$_{49}$ as defined above but with the proviso that R$_{49}$ is not a hydrogen atom, a final compound of formula (I) with R$_5$=H or OH can be obtained by reduction or deprotection of the OR$_{49}$ group in conditions well known to the person skilled in the art.

The OH can thus be halogenated to give access to compounds of formula (I) with R$_5$ representing a halogen atom, in conditions well known to the person skilled in the art.

Compounds of formula (I) with R$_5$ representing a NR$_{50}$R$_{51}$ group can be obtained by methods well known to the person skilled in the arts from a compound of formula (I) with R$_5$=OH, notably by a peptide coupling.

It is to be noted moreover that the compound of formula (I) with Z=H can be obtained directly in one step from compound of formula (IV) and a compound of formula Y—CH$_2$—COR$_5$, by carrying out a cascade reaction of olefination and hydrogenation, such as described in *Eur. J. org. Chem.* 2008, 975.

In the synthesis of compounds of formula (I), R represents preferably a CH$_2$OR$_8$ group with R$_8$ representing a O-protecting group; R$_1$ and R$_2$ represent preferably, independently from one another, an OR$_{15}$ group with R$_{15}$ representing a O-protecting group; and R$_3$ represents preferably an OR$_{22}$ group with R$_{22}$ representing a O-protecting group; or a NR$_{31}$C(O)R$_{32}$ group with R$_{31}$ representing a hydrogen atom and R$_{32}$ representing a (C$_1$-C$_6$)alkyl; and notably R$_3$ represents an OR$_{22}$ group. R$_4$ can represent a hydrogen atom or an OR$_{41}$ group with R$_{41}$ representing a O-protecting group, and notably R$_4$ represents a hydrogen atom.

The present invention relates also to the use of a compound of formula (I) with Y=NH$_2$ or CH$_2$NH$_2$, notably NH$_2$, and/or R$_5$=OH, and in particular a compound of formula (I-1), i.e. a compound of formula (I) for which Y represents a NR$_6$R$_7$ or CH$_2$NR$_6$R$_7$ group, and notably a NR$_6$R$_7$ group, and R$_5$ represents an OR$_{49}$ group, with:

R$_6$ and R$_7$ representing each a hydrogen atom and R$_{49}$ representing a O-protecting group such as a (C$_1$-C$_6$) alkyl group, or R$_{49}$ and R$_6$ representing each a hydrogen atom and R$_7$ representing a N-protecting group such as a Boc or Cbz group, in the synthesis of a peptide, in place of an amino acid such as a serine or a threonine.

The term "amino acid" as used in the present invention refers to natural α-amino acids (e.g. Alanine (Ala), Arginine (Arg), Asparagine (Asn), Aspartic acid (Asp), Cysteine (Cys), Glutamine (Gln), Glutamic acid (Glu), Glycine (Gly), Histidine (His), Isoleucine (Ile), Leucine (Leu), Lysine (Lys), Methionine (Met), Phenylalanine (Phe), Proline (Pro), Serine (Ser), Threonine (Thr), Tryptophan (Trp), Tyrosine (Tyr) and Valine (Val)) in the D or L form, as well as non-natural amino acid (e.g. β-alanine, allylglycine, tent-leucine, 3-amino-adipic acid, 2-aminobenzoic acid, 3-aminobenzoic acid, 4-aminobenzoic acid, 2-aminobutanoic acid, 4-amino-1-carboxymethyl piperidine, 1-amino-1-cyclobutanecarboxylic acid, 4-aminocyclohexaneacetic acid, 1-amino-1-cyclohexanecarboxyilic acid, (1R,2R)-2-aminocyclohexanecarboxylic acid, (1R,2S)-2-aminocyclohexanecarboxylic acid, (1S,2R)-2-aminocyclohexanecarboxylic acid, (1S,2S)-2-aminocyclohexanecarboxylic acid, 3-aminocyclohexanecarboxylic acid, 4-aminocyclohexanecarboxylic acid, (1R,2R)-2-aminocyclopentanecarboxylic acid, (1R,2S)-2-aminocyclopentanecarboxyilic acid, 1-amino-1-cyclopentanecarboxylic acid, 1-amino-1-cyclopropanecarboxylic acid, 4-(2-aminoethoxy)-benzoic acid, 3-aminomethylbenzoic acid, 4-aminomethylbenzoic acid, 2-aminobutanoic acid, 4-aminobutanoic acid, 6-aminohexanoic acid, 1-aminoindane-1-carboxylic acid, 4-aminomethyl-phenylacetic acid, 4-aminophenylacetic acid, 3-amino-2-naphtoic acid, 4-aminophenylbutanoic acid, 4-amino-5-(3-indolyl)-pentanoic acid, (4R,5S)-4-amino-5-methylheptanoic acid, (R)-4-amino-5-methylhexanoic acid, (R)-4-amino-6-methylthiohexanoic acid, (S)-4-amino-pentanoic acid, (R)-4-amino-5-phenylpentanoic acid, 4-aminophenylpropionic acid, (R)-4-aminopimeric acid, (4R,5R)-4-amino-5-hyroxyhexanoic acid, (R)-4-amino-5-hydroxypentanoic acid, (R)-4-amino-5-(p-hydroxyphenyl)-pentanoic acid, 8-aminooctanoic acid, (2S,4R)-4-aminopyrrolidine-2-carboxylic acid, (2S,4S)-4-amino-pyrrolidine-2-carboxylic acid, azetidine-2-carboxylic acid, (2S,4R)-4-benzyl-pyrrolidine-2-carboxylic acid, (S)-4,8-diaminooctanoic acid, tert-butylglycine acid, γ-carboxyglutamate, β-cyclohexylalanine, citrulline, 2,3-diamino propionic acid, hippuric acid, homocyclohexylalanine, moleucine, homophenylalanine, 4-hydroxyproline, indoline-2-carboxylic acid, isonipecotic acid, α-methyl-alanine, nicopetic acid, norleucine, norvaline, octahydroindole-2-carboxylic acid, ornithine, penicillamine, phenylglycine, 4-phenyl-pyrrolidine-2-carboxylic acid, pipecolic acid, propargylglycine, 3-pyridinylalanine, 4-pyridinylalanine, 1-pyrrolidine-3-carboxylic acid, sarcosine, statines, tetrahydroisoquinoline-1-carboxylic acid, 1,2,3,4-tetrahydroisoquinoline-3-carboxylic acid, or tranexamic acid). Preferably, it will be a natural or non-natural α-amino acid and preferably a natural α-amino acid.

The term "peptide" as used in the present invention refers to a chain comprising at least 2, and notably 2 to 30, amino acids as defined above (and preferably natural α-amino acid)

bound together by means of peptide bounds (i.e. amide function). It can be in particular an oligopeptide having in particular 2 to 20 amino acids.

The synthesis of the peptide will be carried out by classical methods well known to the person skilled in the art, using notably steps of protection/deprotection and peptide coupling.

The peptide can notably be an oligopeptide comprising 2 to 20 amino acids.

The present invention concerns also a peptide of formula (VI) in which at least one amino acid, such as a serine or a threonine, has been replaced with a compound of formula (I) in which $Y=NHR_7$ or $CH_2NHR_7$, and notably $NHR_7$, and/or $R_5=OH$, and in particular with $Y=NH_2$ or $CH_2NH_2$, and notably $NH_2$, and $R_5=OH$, the Y and/or $R_5$ group being linked to an amino acid of the peptide by means of peptide bond (i.e. an amide bond).

This means that the hydrogen of the $NHR_7$ or $CH_2NHR_7$ moiety of Y is replaced by a bond with a C(=O) moiety derived from the acid function of an amino acid, and/or the OH moiety of $R_5$ is replaced by a bond with a nitrogen derived from the amino function of another amino acid.

The groups R, $R_1$, $R_2$, $R_3$ and $R_4$ of the compound of formula (I) are moreover as defined previously.

The peptide can notably be an oligopeptide comprising 2 to 20 amino acids. It can be chosen notably among the following oligopeptides:

VI-12

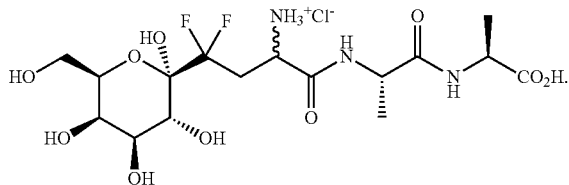

The invention relates also to a peptide (VI) as defined previously for use as medicament, notably for the treatment or the prevention of viral, bacterial or inflammatory diseases.

The invention concerns also the use of a peptide (VI) in the manufacture of a medicament, intended notably for the treatment or the prevention of viral, bacterial or inflammatory diseases.

More specifically, the invention concerns also a method for treating or preventing viral, bacterial or inflammatory diseases comprising the administration to a person in need thereof of a sufficient quantity of a peptide (VI).

The invention concerns also a method for cosmetic treatment comprising the administration to a person in need thereof of a sufficient quantity of a peptide (VI).

The invention relates also to a peptide (VI) as defined previously for use as cancer vaccine.

The invention concerns also the use of a peptide (VI) in the manufacture of a medicament, intended notably for use as cancer vaccine.

More specifically, the invention concerns also a method for preventing cancer comprising the administration to a person in need thereof of a sufficient quantity of a peptide (VI).

Indeed, the compound of formula (I) integrated in the peptide (VI) represents a mimic of antigen Tn.

In this case, advantageously R=CH$_2$OH and R$_1$=R$_2$=OH. R$_4$ can also represent advantageously a hydrogen atom. R$_3$ will be in particular an OH or NHAc group, preferably a NHAc group.

Advantageously, the Y group of the compound of formula (I) integrated in the peptide (VI) will be a NH$_2$ group not bound to another amino acid of the peptide (VI).

The cancer in question can be in particular breast, lung, prostate or colon cancer.

The present invention relates thus also to the use of a compound of formula (I) according to the present invention as a mimic of antigen Tn.

In this case, advantageously R=CH$_2$OH and R$_1$=R$_2$=OH. R$_4$ can also represent advantageously a hydrogen atom. R$_3$ will be in particular an OH or NHAc group, preferably a NHAc group. Advantageously, Y will represent a NH$_2$ group.

The present invention relates also to pharmaceutical or cosmetic compositions comprising at least one peptide (VI) and a pharmaceutically acceptable carrier. Said pharmaceutically acceptable carrier can be a hapten, a protein, a chemical scaffold or a carrier matrix.

The pharmaceutical compositions of the invention can be intended to oral, sublingual, subcutaneous, intramuscular, intravenous, transdermal, local or rectal administration. The active ingredient can be administered in unit forms for administration, mixed with conventional pharmaceutical carriers, to animals or to humans. Suitable unit forms for administration comprise the forms for oral administration, such as tablets, gelatin capsules, powders, granules and oral solutions or suspensions, the forms for sublingual and buccal administration, the forms for subcutaneous, intramuscular, intravenous, intranasal or intraoccular administration and the forms for rectal administration.

The cosmetic compositions of the invention can be intended to oral, sublingual, cutaneous, topical, transdermal or local administration. The active ingredient can be administered in unit forms for administration, mixed with conventional pharmaceutical carriers, to animals or to humans. Suitable unit forms for administration comprise the forms for oral administration, such as tablets, gelatin capsules, powders, granules and oral solutions or suspensions, the forms for sublingual and buccal administration, the forms for topical, cutaneous, transdermal or local administration.

When a solid composition is prepared in the form of tablets, the main active ingredient is mixed with a pharmaceutical vehicle such as gelatin, starch, lactose, magnesium stearate, talc, gum arabic and the like. The tablets may be coated with sucrose or with other suitable materials, or they may be treated in such a way that they have a prolonged or delayed activity and they continuously release a predetermined amount of active principle.

A preparation in gelatin capsules is obtained by mixing the active ingredient with a diluent and pouring the mixture obtained into soft or hard gelatin capsules.

A preparation in the form of syrup or elixir may contain the active ingredient together with a sweetener, an antiseptic, or also a taste enhancer or a suitable coloring agent.

The water-dispersible powders or granules may contain the active ingredient mixed with dispersing agents or wetting agents, or suspending agents, and with flavor correctors or sweeteners.

For rectal administration, suppositories are used which are prepared with binders which melt at rectal temperature, for example cocoa butter or polyethylene glycols.

For parenteral, intranasal or intraoccular administration, aqueous suspensions, isotonic saline solutions or sterile and injectable solutions which contain pharmacologically compatible dispersing agents and/or wetting agents are used.

The active principle may also be formulated in the form of microcapsules, optionally with one or more carrier additives.

The compounds of the invention can be used in a pharmaceutical or cosmetic composition at a dose ranging from 0.01 mg to 1000 mg a day, administered in only one dose once a day or in several doses along the day, for example twice a day. The daily administered dose is advantageously comprises between 5 mg and 500 mg, and more advantageously between 10 mg and 200 mg. However, it can be necessary to use doses out of these ranges, which could be noticed by the person skilled in the art.

The present invention relates also to the use of a peptide (VI) in the preservation of biological materials, such as cells, tissues and organs, notably below 37° C., such as below 0° C., notably for the cryopreservation of biological materials (human organs or tissues (e.g. for transplant) or cells), and the preservation of food.

The present invention relates also to the cosmetic use of a peptide (VI), especially its cosmetic use in anti-aging applications.

Indeed the study of fish present in the iced water of the polar area shown that they resist to temperatures below 0° C. because of the presence in their blood and in their organism of particular proteins protecting them against frost (*Chem. Rev.* 1996, 16, 2).

These proteins are called anti-freeze glycoprotein (AFGP), they contain a repetitive moiety consisting of a glycosylated peptide containing 3 amino acids (threonine-alanine or proline-alanine) and can have the following structure:

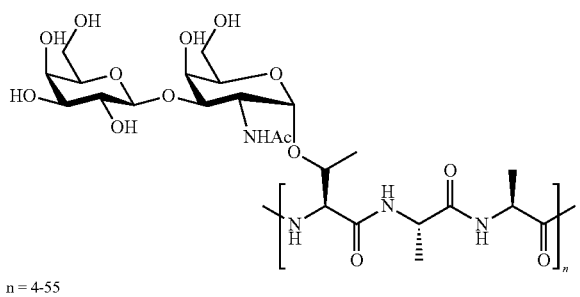

n = 4-55

In this case, the peptide will advantageously respond to the following formula (IX), and in particular (IXa):

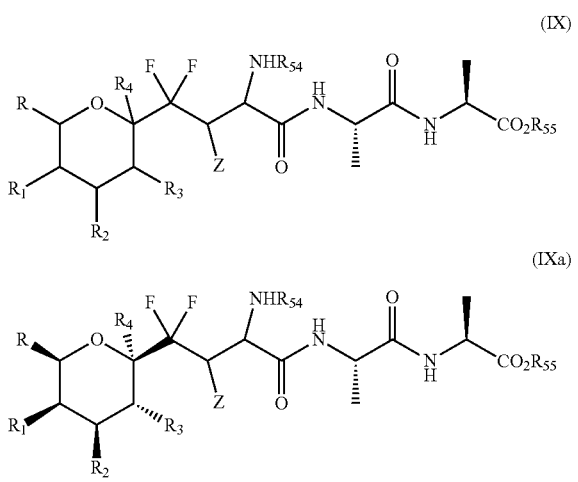

in which R, $R_1$, $R_2$, $R_3$, $R_4$ and Z are as defined above (including the preferred embodiments), $R_{54}$ represents a hydrogen atom or a N-protecting group such as Cbz and $R_{55}$ represents a hydrogen atom or an O-protecting group such as Bn.

Advantageously, $R=CH_2OH$, $R_1=R_2=R_3=OH$ and $R_4=H$ or OH. $R_{54}$ and $R_{55}$ each represent advantageously a hydrogen atom. Z can be also a hydrogen atom.

It will be in particular a peptide chosen from examples VI-1 to VI-12.

Examples of such compound preparations of the present invention, as well as results of their biological activity are described below for non-limiting and illustrative purposes.

FIGURES

FIGS. 1a to 6b represent mass spectra (ESI+) of the following compounds:
FIG. 1a: compound Ad1 without β-Galactosidase,
FIG. 1b: compound Ad1 with β-Galactosidase,
FIG. 2a: compound Ad2 without β-Galactosidase,
FIG. 2b: compound Ad2 with β-Galactosidase,
FIG. 3a: compound Cd1 without α-Galactosidase,
FIG. 3b: compound Cd1 with α-Galactosidase,
FIG. 4a: compound Cd2 without α-Galactosidase,
FIG. 4b: compound Cd2 with α-Galactosidase,
FIG. 5a: compound Dd1 without α-Galactosidase,
FIG. 5b: compound Dd1 with α-Galactosidase,
FIG. 6a: compound Dd2 without α-Galactosidase, and
FIG. 6b: compound Dd2 with α-Galactosidase.

Figure 7:
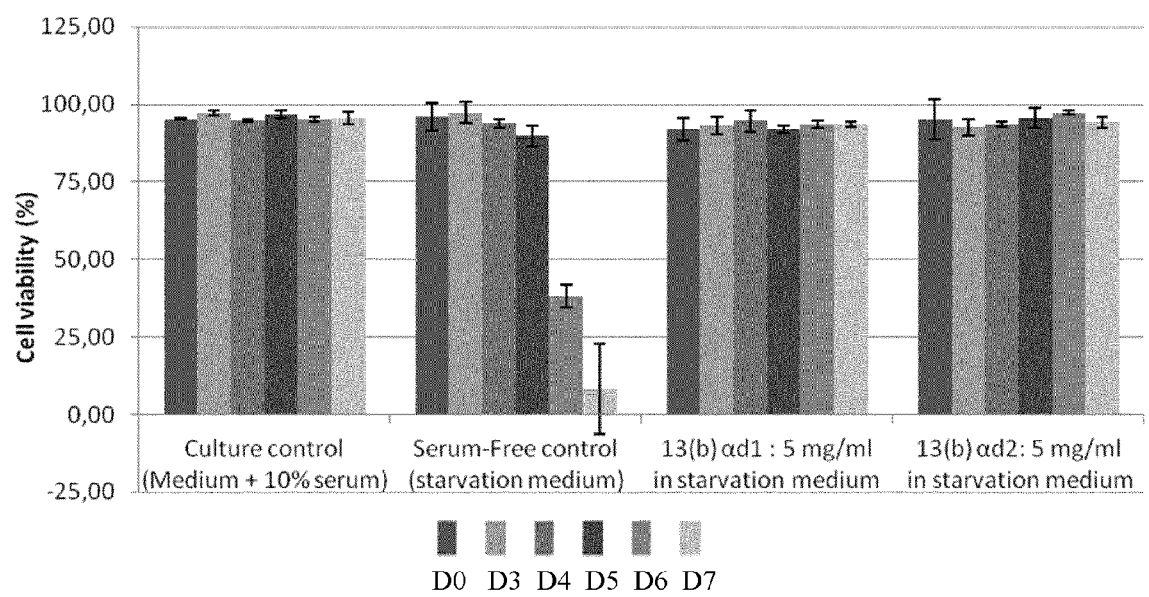

FIG. 7 represents the evolution of the percentage of fibroblast viability for 7 days after serum deprivation.

EXAMPLES

I—Preparation of the Compounds According to the Invention

The features of the devices used to conduct analyses of all of the compounds described in this application are indicated below:

The $^{19}F$ NMR spectra were recorded on BRUKER DPX 300 and DPX 600 spectrometers. The internal reference used is fluorotrichloromethane ($CFCl_3$). Chemical shifts are expressed in parts per million (ppm) and coupling constants (J) in Hertz (Hz).

The following abbreviations were used:
s for singlet, bs for a broad singlet, d for doublet, t for triplet, qdt for quartet, m for multiplet or massive, dd for doublet of doublets, etc.

The mass spectra were obtained on a spectrophotometer Micromass TOF-SPEC E 20 kV, α-cyano type, for MALDI ionization and JEOL AX500, 3 kV, Canon FAB JEOL, Xe, 4 kV, 10 μA limiting current, Gly-NBA 50:50 for FAB ionization.

Separations via column chromatography are carried out under light pressure on Kieselgel 60 silica (230-400 Mesh, Merck).

Monitoring of reactions is performed by thin-layer chromatography (Kieselgel 60E-254-0.25-mm plates). The ratio of the migration distance of a compound on a given support to the migration distance of an eluent is called the retardation factor.

The compounds have been numbered by assigning the symbol α to the alpha derivatives and β to the beta derivatives, and when necessary by assigning the letter G to the galactose derivatives and the letter T to the talose derivatives.

Synthesis of Compound 2β

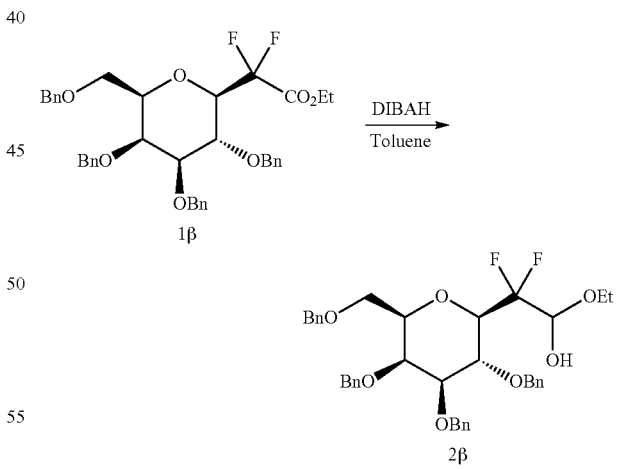

To a cooled (−78° C.) solution of compound 1β (1.03 g; 1.60 mmol; 1 eq.), synthesized according to *Synlett* 2005, 17, 2627-2630 and *Org. Lett.* 2002, 4, 757-759 —see also WO 2004/014928, WO 2007/125203 and WO 2007/125194, in anhydrous toluene (40 mL) was added a solution of diisobutylaluminium hydride (1.2 M in toluene; 2.00 mL; 2.40 mmol; 1.5 eq.) and the resultant mixture was stirred for 1 h at this temperature. The reaction was then quenched with ethanol (10 mL) and the solution was warmed to −20° C. for 10 min. A Rochelle's salt solution (20%, 45 mL) was then added and the solution was vigorously stirred for 1 h. The reaction medium was extracted with ethyl acetate. The combined organic extracts were washed with brine, dried over magnesium sulfate, filtered and evaporated in vacuo to give compound 2β (1.03 g; yellow oil).

2β: $C_{38}H_{42}F_2O_7$ M=648.73 g·mol$^{-1}$
Mass (ESI$^+$): 666.51 (M+H$_2$O); 671.43 (M+Na)

Synthesis of Compound 2(a)α

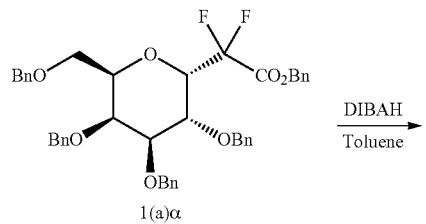

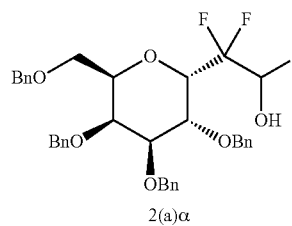

2(a)α

To a cooled (−78° C.) solution of compound 1(a)α (0.112 g, 0.157 mmol, 1 eq), (synthesized according to *Org. Lett.* 2007, 9, 2477-2480 with the use of Al(OiPr)$_3$/iPrOH in refluxing DCM for the reducing step, in anhydrous toluene (4.1 mL) was added a solution of diisobutylaluminium hydride (1.2 M in toluene; 0.211 mL; 0.253 mmol; 1.6 eq.) and the resultant mixture was stirred for 1 h at this temperature. The reaction media was warmed to −20° C. for 10 min and then quenched with ethanol (5 mL). A Rochelle's salt solution (20%, 10 mL) was then added and the solution was vigorously stirred for 1 h. The reaction medium was extracted with ethyl acetate. The combined organic extracts were washed with brine, dried over magnesium sulfate, filtered and evaporated in vacuo to give compound 2(a)α (0.100 g) which was used in the next step without any further purification.

2(a)α: $C_{43}H_{44}F_2O_7$ M=710.80 g·mol$^{-1}$
Mass (ESI$^+$): 728.20=[M+H$_2$O]$^+$; 733.33=[M+Na]$^+$ Synthesis of Compound 2(b)α

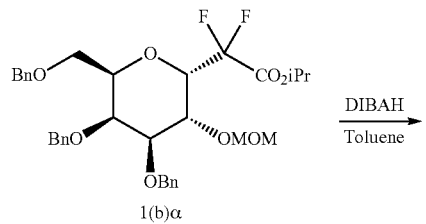

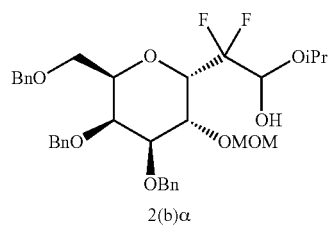

2(b)α

To a cooled (−78° C.) solution of compound 1(b)α (0.248 g, 0.404 mmol, 1 eq), synthesized according to *Org. Lett.* 2007, 9, 2477-2480 with the use of Al(OiPr)$_3$/iPrOH in refluxing DCM for the reducing step, in anhydrous toluene (9 mL) was added a solution of diisobutylaluminium hydride (1 M in toluene; 0.600 mL; 0.605 mmol; 1.5 eq.) and the resultant mixture was stirred for 1 h at this temperature. The reaction medium was warmed to −20° C. for 10 min and then quenched with ethanol (2 mL). A Rochelle's salt solution (20%, 10 mL) was then added and the solution was vigorously stirred for 1 h. The reaction medium was extracted with ethyl acetate. The combined organic extracts were washed with brine, dried over magnesium sulfate, filtered and evaporated in vacuo to give compound 2(b)α (0.244 g) which was used in the next step without further purification.

2(b)α: $C_{34}H_{42}F_2O_8$ M=616.69 g·mol$^{-1}$
Mass (ESI$^+$): 639.20 [M+Na]$^+$; 1255.07 [2M+Na]$^+$ Synthesis of Compounds 3(b)α and 3β

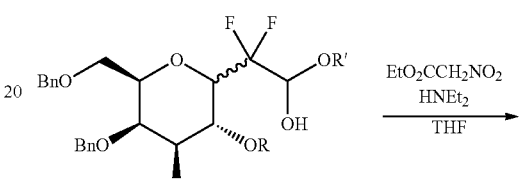

2(b)α (R = MOM; R' = iPR)
2β (R = Bn; R' = Et)

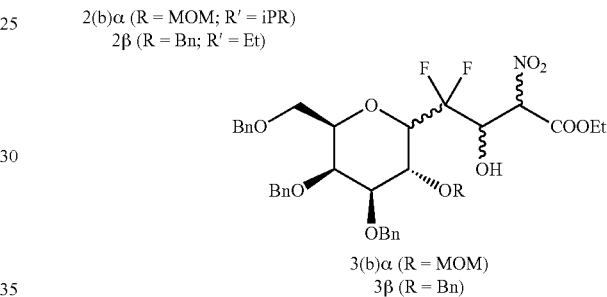

3(b)α (R = MOM)
3β (R = Bn)

Compound 3β: Diethylamine (246 μL; 2.39 mmol; 1.5 eq.) was added to a solution of compound 2β (1.03 g) and ethyl nitroacetate (264 μL; 2.39 mmol; 1.5 eq.) in THF (5 mL) at 0° C. The mixture was stirred for 3 h, then at 0° C., ethyl acetate (5 mL) and HCl (0.5N, 5 mL) were added. The organic layer was separated and the aqueous layer was extracted with ethyl acetate. The combined organic extracts were dried over magnesium sulfate, filtered and evaporated to produce compound 3β (1.19 g; yellow oil). Compound 3β was used in the next step without further purification.

3β: $C_{40}H_{43}F_2NO_{10}$ M=735.77 g·mol$^{-1}$
Mass (ESI$^+$): 753.00 (M+H$_2$O); 758.13 (M+Na)

Compound 3(b)α: This compound (145 mg) was prepared from compound 2(b)α (244 mg) following the same procedure as for compound 3β.

3(b)α: $C_{35}H_{41}F_2NO_{11}$ M=689.70 g·mol$^{-1}$
Mass (ESI$^+$): 707.33 (M+H$_2$O)

Synthesis of Compounds 4 (b)α et 4β

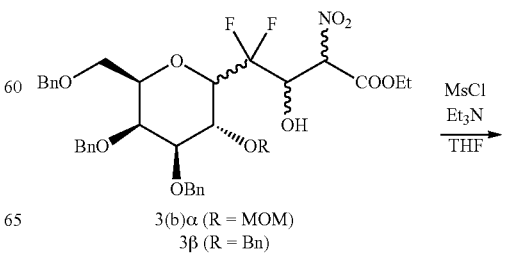

3(b)α (R = MOM)
3β (R = Bn)

-continued

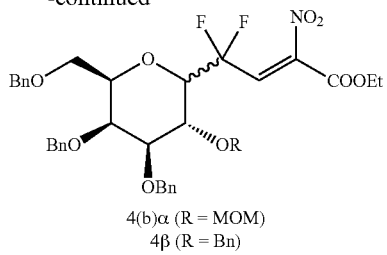

4(b)α (R = MOM)
4β (R = Bn)

Compound 4β: To a chilled (0° C.) solution of compound 3β (1.19 g) in THF (30 mL) was added mesyl chloride (377 μL; 4.87 mmol) and triethylamine (684 μL; 4.87 mmol). After stirring for 4 h, water was added (20 mL) and the mixture was extracted with Et$_2$O. The combined organic phase was dried (MgSO$_4$), filtered, and evaporated. The residue was purified by chromatography (cyclohexane/ethyl acetate 100/0 to 80/20) to give compound 4β (0.50 g; 0.70 mmol, yellow oil) as a diastereomeric mixture (50/50 ratio as measured by $^{19}$F NMR).

4β: $C_{40}H_{41}F_2NO_9$ M=717.75 g·mol$^{-1}$
Mass (ESI$^+$): 735.33 (M+H$_2$O); 740.33 (M+Na)

Compound 4(b)α: This compound (55 mg) was prepared from compound 3(b)α (64 mg) following the same procedure as for compound 4β.

4(b)α: $C_{35}H_{39}F_2NO_{10}$ M=671.68 g·mol$^{-1}$
Mass (ESI$^+$): 689.13 (M+H$_2$O)

Synthesis of Compounds 5(b)α and 5β

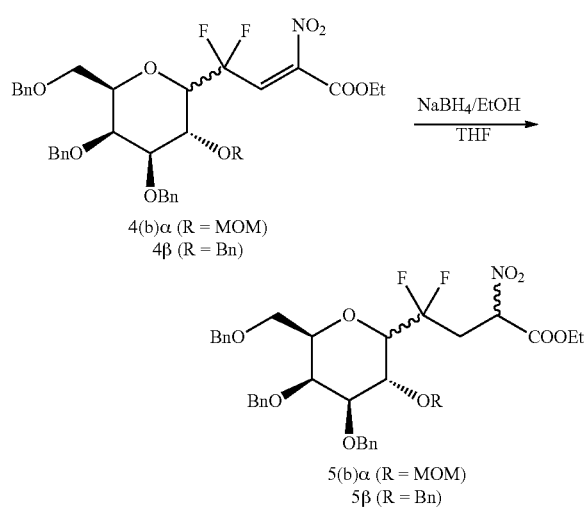

4(b)α (R = MOM)
4β (R = Bn)

5(b)α (R = MOM)
5β (R = Bn)

Compound 5β: To a chilled (0° C.) solution of compound it (3.90 g; 5.43 mmol) in THF (150 mL) and ethanol (150 mL) was added NaBH$_4$ (410 mg; 10.84 mmol; 2 eq.). The reaction mixture was quenched with HCl 2N and was extracted with Et$_2$O. The combined organic extracts were dried over magnesium sulfate, filtered and evaporated. The residue was then purified by chromatography (cyclohexane/ethyl acetate 95/5 to 60/40) to give compound 5β as a diastereomeric mixture (2.49 g; 3.46 mmol; yellow oil) with a yield of 64%. The two diastereomers were present in a 50/50 ratio as measured by $^{19}$F NMR.

5β: $C_{40}H_{43}F_2NO_9$ M=719.77 g·mol$^{-1}$
Mass (ESI$^+$): 737.13 (M+H$_2$O); 742.20 (M+Na)
NMR $^{19}$F (CDCl$_3$, 282.5 MHz) (with H coupled): −101.9/−103.7 (4 m, 2F); −107.1/−108.7 (4 m, 2F).

NMR $^{19}$F (CDCl$_3$, 282.5 MHz) (without H coupled): −102.5 (d, J=258 Hz, 1F); −103.2 (d, J=258 Hz, 1F); −107.7 (d, J=258 Hz, 1F); −108.2 (d, J=258 Hz, 1F).

Compound 5(b)α: This compound (25 mg; 0.04 mmol; yellow oil) was prepared from compound 4(b)α (53 mg) following the same procedure as for compound 5β.

5(b)α: $C_{35}H_{41}F_2NO_{10}$ M=673.70 g·mol$^{-1}$
Mass (ESI$^+$): 691.13 (M+H$_2$O)

Synthesis of Compounds 5(a)α and 5(b)α

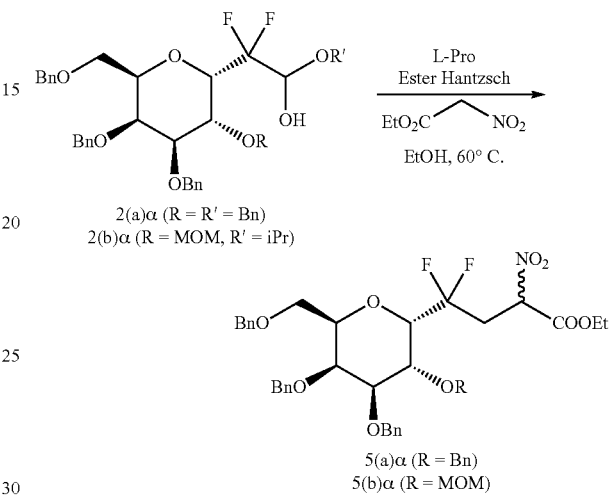

2(a)α (R = R' = Bn)
2(b)α (R = MOM, R' = iPr)

5(a)α (R = Bn)
5(b)α (R = MOM)

Compound 5(a)α: To a mixture of compound 2a(α) (0.100 g, 0.142 mmol, 1 eq), L-proline (L-Pro) (0.5 eq) and Hantzsch ester (1.3 eq) in ethanol (1 ml) was added ethyl nitroacetate (1.5 eq). The reaction mixture was stirred overnight at 60° C. Ether (15 ml) was added and the organic phase was washed with water (3×10 ml), dried over magnesium sulfate, filtered and evaporated. The residue was then purified by chromatography (cyclohexane/ethyle acetate 97/3 to 40/60) to give compound 5(a) a (68.4 mg, n=0.095 mmol, yield 67%)

5(a)α: $C_{40}H_{43}F_2NO_9$ M=719.77 g/mol
NMR $^{19}$F (CDCl$_3$) 282.5 MHz (with H coupled): −96.7/−98.5 (2F; 3m); −107.5/−108.7 (2F; 2m)
NMR $^{19}$F (CDCl$_3$) 282.5 MHz (without H coupled): −97.2 (1F; d; J=260 Hz); −97.9 (1F; d; J=260 Hz); −108.1 (1F; d; J=257 Hz); −108.2 (1F; d; J=257 Hz);
Mass (ESI$^+$): 742.20 [M+Na]$^+$ Compound 5(b)α: This compound (3.55 g, 5.27 mmol, yield 47%) was prepared from compound 2(b)α (6.96 g, 11.29 mmol) following the same procedure as for compound 5(a)α.

5(b)α: $C_{35}H_{41}F_2NO_{10}$ M=673.70 g·mol$^{-1}$
Mass (ESI$^+$): 691.13 (M+H$_2$O)

Synthesis of Compounds 5(c)β

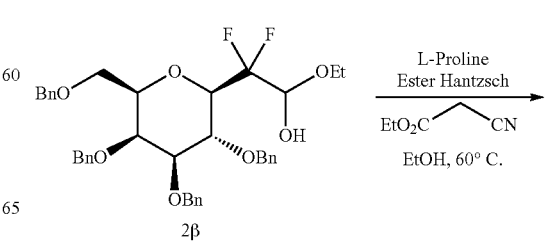

2β

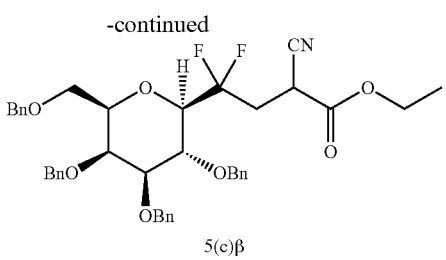

5(c)β

Compound 5(c)β: This compound (yield=43%) was prepared from compound 2β (213 mg) and ethylcyanoacetate (52 µL, 0.49 mmol) following the same procedure as for compound 5(a)α

5(c)α: $C_{41}H_{43}F_2NO_7$ M=699.78 g·mol$^{-1}$
Mass (ESI$^+$): 700.29[M+H]$^+$; 722.27 [M+Na]$^+$.
NMR $^{19}$F (CDCl$_3$, 282.5 MHz) (without H coupled): −103.3 (d, J=256 Hz, 1F, CF$_2$); −103.6 (d, J=256 Hz, 1F, CF$_2$); −107.1 (d, J=256 Hz, 1F, CF$_2$); −108.1 (d, J=256 Hz, 1F, CF$_2$).
NMR $^{19}$F (CDCl$_3$, 282.5 MHz) (with H coupled): −102.8/−104.1 (4m, 2F, CF$_2$); −106.6/−108.5 (3m, 2F, CF$_2$).

Synthesis of Compounds 6β (6βd1+6βd2), 6(a)α and 6(b)α (6(b)αd1/6(b)αd2

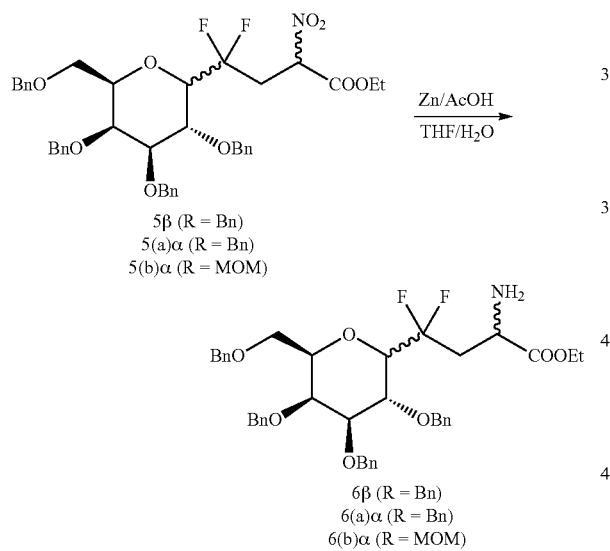

5β (R = Bn)
5(a)α (R = Bn)
5(b)α (R = MOM)

6β (R = Bn)
6(a)α (R = Bn)
6(b)α (R = MOM)

Compound 6β: To a solution of compound 5β (1.53 g; 2.13 mmol) in THF (7 mL), water (10 mL) and acetic acid (10 mL), was added Zn dust (2.9 g; 44 mmol; 20 eq.). The resultant mixture was stirred at room temperature for 12 hours. The reaction mixture was filtered through Celite and concentrated. A solution of NH$_4$OH was added to adjust the pH of the aqueous layer to pH8, and the resultant aqueous layer was then extracted with ethyl acetate. The combined organic phase was dried (MgSO$_4$), filtered, and concentrated. The crude mixture was purified by chromatography on silica gel (cyclohexane/ethyl acetate 90/10 to 20/80) to give compounds 6β (6βd1/6βd2 (50/50)) (0.91 g; 1.32 mmol, yellow oil) 62% yield. Each diastereomer (6βd1 and 6βd2) was obtained separately.

6βd1+6βd2: $C_{40}H_{45}F_2NO_7$ M=689.78 g·mol$^{-1}$
Mass (ESI$^+$): 690.53 (M+H)
NMR $^{19}$F (CDCl$_3$, 282.5 MHz) (with H coupled):
6βd1: −103.2/−104.2 (2m, 1F); −104.2/−105.2 (2m, 1F).
6βd2: −102.6/−103.7 (2m, 1F); −105.0/−106.0 (2m, 1F).
NMR $^{19}$F (CDCl$_3$, 282.5 MHz) (without H coupled):
6βd1: −103.8 (d, J=256 Hz, 1F); −104.7 (d, J=256 Hz, 1F).
6βd2: −103.1 (d, J=255 Hz, 1F); −105.5 (d, J=255 Hz, 1F).

Compound 6(a)α: This compound (m=44.9 mg, n=0.065 mmol, yield=47%) was prepared from compound 5(a)α (100 mg, 0.139 mmol, 1 eq) following the same procedure as for compound 6β.

6(a)α: $C_{40}H_{45}F_2NO_7$ M=689.78 g/mol
Mass (ESI$^+$): 690.33=[M+H]$^+$

Compound 6(b)α: This compound was obtained as a mixture of diastereomer in a proportion 50/50 from compound 5(b)α (3.55 g, 5.27 mmol, 1 eq) following the same procedure as for 6β. Each diastereomer has been isolated 6(b)αd1 (m=1.03 g, n=1.60 mmol, yield=30%) and 6(b)αd2 (m=1.06 mg, n=1.60 mmol, yield=31%).

6(b)αd1/6(b)αd2: $C_{35}H_{43}F_2NO_8$ M=643.71 g/mol
6(b)αd1
Mass (ESI$^+$): 644.5 [M+H]$^+$, 666.5 [M+Na]$^+$
NMR $^{19}$F (CDCl$_3$, 282.5 MHz) (without H coupled): −101.1 (1F; d; J=258 Hz); −106.2 (1F; d; J=258 Hz)
6(b)αd2
Mass (ESI$^+$): 644.5 [M+H]$^+$
NMR $^{19}$F (CDCl$_3$, 282.5 MHz) (without H coupled): −99.4 (1F; d; J=256 Hz); −106.1 (1F; d; J=256 Hz)

Synthesis of Compound 7β

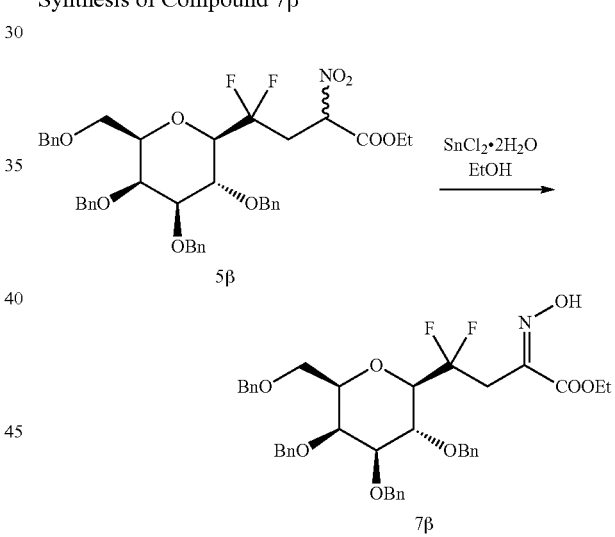

5β

7β

To a solution of compound 5β (54 mg; 0.075 mmol) in ethanol, SnCl$_2$.2H$_2$O (170 mg; 0.75 mmol; 10 eq.) was added. The mixture was then stirred for 24 h and concentrated. The residue was then diluted in ethyl acetate and a solution of KOH (2M) was added. The aqueous layer was further extracted with portions of ethyl acetate and the combined organic phase was washed with brine and water, dried over magnesium sulfate, filtered and concentrated. The crude residue was purified by chromatography (cyclohexane/ethyl acetate 90/10 to 40/60) to give compounds 7β in 56% yield.

7β: $C_{40}H_{43}F_2NO_8$ M=703.77 g·mol$^{-1}$
Mass (ESI$^+$): 721.47 (M+H$_2$O); 726.46 (M+Na)
NMR $^{19}$F (CDCl$_3$, 282.5 MHz) (with H coupled): −100.0/−101.0 (2m, 1F); −103.8/−104.6 (2m, 1F).
NMR $^{19}$F (CDCl$_3$, 282.5 MHz) (without H coupled): −100.5 (d, J=253 Hz, 1F); −104.2 (d, J=253 Hz, 1F).

Synthesis of Compounds 8β (8βd1/8βd2), 8(a)α and 8(b)α (8(b)αd1/8(b)αd2)

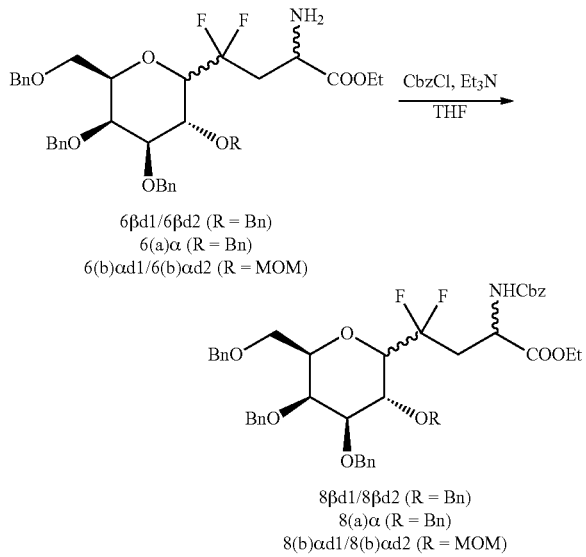

6βd1/6βd2 (R = Bn)
6(a)α (R = Bn)
6(b)αd1/6(b)αd2 (R = MOM)

8βd1/8βd2 (R = Bn)
8(a)α (R = Bn)
8(b)αd1/8(b)αd2 (R = MOM)

Compound 8β: To a chilled (0° C.) solution of compound 6βd1 (810 mg; 1.18 mmol) in THF (15 mL) was added benzyl chloroformate (420 μL; 2.95 mmol; 2.5 eq.) and triethylamine (247 μL; 1.77 mmol; 1.5 eq.). The resultant mixture was stirred for 12 h and then extracted with ethyl acetate, washed with a saturated aqueous NaHCO$_3$ solution, dried (MgSO$_4$), filtered and evaporated. The crude residue was purified by chromatography (cyclohexane/ethyl acetate 90/10 to 40/60) to give compound 8βd1 (792 mg; 0.96 mmol) as a yellowish solid 81% yield.

Compound 8βd2 (773 mg; 0.94 mmol) in the form of yellow oil, was prepared following the same procedure but starting from compound 6βd2 (718 mg; 1.04 mmol).

8βd1+8βd2: $C_{48}H_{51}F_2NO_9$ M=823.92 g·mol$^{-1}$
Mass (ESI$^+$):824.27 (M+H); 841.47 (M+H$_2$O); 846.47 (M+Na)
NMR $^{19}$F (CDCl$_3$, 282.5 MHz) (with H coupled):
8βd1: −102.0/−103.0 (2m, 1F); −103.5/−104.6 (2m, 1F).
8βd2: −101.0/−102.1 (2m, 1F); −104.0/−105.1 (2m, 1F).
NMR $^{19}$F (CDCl$_3$, 282.5 MHz) (without H coupled):
8βd1: −102.5 (d, J=257 Hz, 1F); −104.1 (d, J=257 Hz, 1F).
8βd2: −101.5 (d, J=258 Hz, 1F); −104.6 (d, J=258 Hz, 1F).

Compound 8(a)α: This compound (m=27 mg, n=0.033 mmol, yield=52%) was prepared from compound 6(a)α (44 mg, 0.064 mmol, 1 eq) following the same procedure as for compound 8β.

8(a)α: $C_{48}H_{51}F_2NO_9$ M=823.92 g·mol$^{-1}$
Masse (ESI$^+$): 846.3 (M+Na); 862.3 (M+K)

Compound 8(b)α: The compound 8(b)αd1 (m=847 mg, n=1.09 mmol, yield=100%) was prepared from compound 6(b)αd1 (700 mg, 1.09 mmol, 1 eq) following the same procedure as for compound 8β.

The compound 8(b)αd2 (m=847 mg, n=1.09 mmol, yield=100%) was prepared from compound 6(b)αd2 (700 mg, 1.09 mmol, 1 eq) following the same procedure as for compound 8β.

8(b)αd1/8(b)αd2: $C_{43}H_{49}F_2NO_{10}$ M=777.85 g·mol$^{-1}$
8(b)αd1
Mass (ESI$^+$): 778.4 [M+H]$^+$; 795.4 [M+H$_2$O]$^+$
NMR $^{19}$F (CDCl$_3$, 282.5 MHz) (with H coupled): −100.5/−101.8 (1F; 2m); −104.9/−106.2 (1F; 2m)
NMR $^{19}$F (CDCl$_3$, 282.5 MHz) (without H coupled): −101.1 (1F; d; J=258 Hz); −105.6 (1F; d; J=258 Hz)
8(b)αd2
Mass (ESI$^+$): 778.3 [M+H]$^+$, 795.4 [M+H$_2$O]$^+$
NMR $^{19}$F (CDCl$_3$, 282.5 MHz) (with H coupled): −98.0/−99.2 (1F; 2m); −106.2/−107.6 (1F; 2m)
NMR $^{19}$F (CDCl$_3$, 282.5 MHz) (without H coupled): −98.5 (1F; d; J=259 Hz); −106.9 (1F; d; J=259 Hz)

Synthesis of Compounds 9β (9βd1/9βd2) and 9(b)α (9(b)αd1/9(b)αd2)

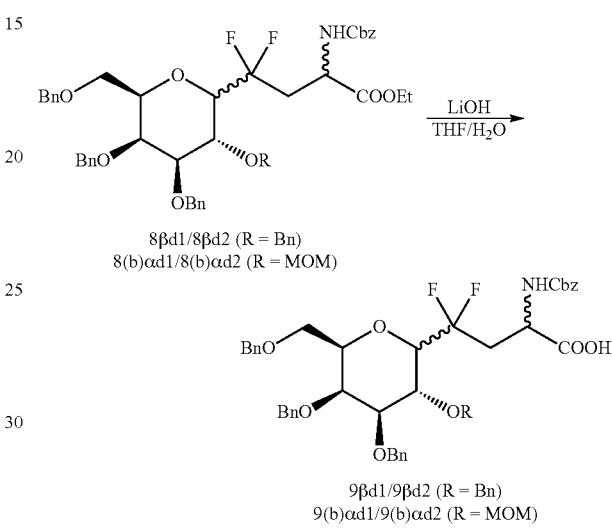

8βd1/8βd2 (R = Bn)
8(b)αd1/8(b)αd2 (R = MOM)

9βd1/9βd2 (R = Bn)
9(b)αd1/9(b)αd2 (R = MOM)

Compound 9β2: To a solution of compound 8βd1 (800 mg; 0.97 mmol) in THF (30 mL) and water (1.7 mL) was added LiOH (70 mg; 2.91 mmol). The solution was stirred for 12 hours then quenched with 1N HCl aqueous solution. The reaction mixture was then extracted with dichloromethane, dried over sulfate magnesium, filtered and evaporated to give compound 9βd1 (680 mg; 0.86 mmol, yellow oil) in 89% yield.

Compound 9βd2 (703 mg; 0.88 mmol) was prepared in 97% yield from compound 8βd2 (750 mg; 0.91 mmol) following the same procedure as for compound 9βd1.

9βd1/9βd2: $C_{46}H_{47}F_2NO_9$ M=795.86 g·mol$^{-1}$
Mass (ESI$^+$): 796.04 (M+H); 818.39 (M+Na)
NMR $^{19}$F (CDCl$_3$, 282.5 MHz) (with H coupled):
9βd1: −98.3/−99.3 (2m, 1F); −100.4/−101.4 (2m, 1F).
9βd2: −100.0/−101.3 (2m, 1F); −103.4/−104.7 (2m, 1F).
NMR $^{19}$F (CDCl$_3$, 282.5 MHz) (without H coupled):
9βd1: −98.8 (d, J=262 Hz, 1F); −100.9 (d, J=262 Hz, 1F).
9βd2: −100.8 (d, J=259 Hz, 1F); −104.0 (d, J=259 Hz, 1F).

Compound 9(b)α: The compound 9(b)αd1 (m=818 mg, n=1.09 mmol, yield=100%) was prepared from compound 8(b)αd1 (847 mg, 1.09 mmol, 1 eq) following the same procedure as for compound 9βd1.

The compound 9(b)αd2 (m=818 mg, n=1.09 mmol, yield=100%) was prepared from compound 8(b)αd2 (847 mg, 1.09 mmol, 1 eq) following the same procedure as for compound 9βd1.

9(b)αd1/9(b)αd2: $C_{41}H_{45}F_2NO_{10}$ M=749.79 g·mol$^{-1}$
9(b)αd1
Mass (ESI$^+$): 750.3 [M+H]$^+$, 767.3 [M+H$_2$O]$^+$
NMR $^{19}$F (CDCl$_3$, 282.5 MHz) (with H coupled): −99.9/−101.1 (1F; 2m); −103.6/−105.0 (1F; 2m)

NMR $^{19}$F (CDCl$_3$, 282.5 MHz) (without H coupled): −100.4 (1F; d; J=258 Hz); −104.2 (1F; d; J=258 Hz)

9(b)αd2

Mass (ESI$^+$): 750.3 [M+H]$^+$, 767.3 [M+H$_2$O]$^+$

NMR $^{19}$F (CDCl$_3$, 282.5 MHz) (with H coupled): −96.5/−97.7 (1F; 2 m); −105.6/−107.0 (1F; 2m)

NMR $^{19}$F (CDCl$_3$, 282.5 MHz) (without H coupled): −97.1 (1F; d; J=261 Hz); −106.3 (1F; d; J=261 Hz)

Synthesis of Compounds 10β (10βd1/10βd2) and 10(b)α (10(b)αd1/10(b)αd2)

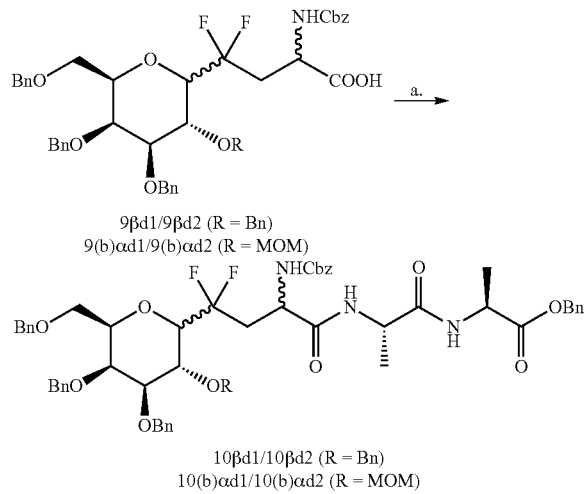

9βd1/9βd2 (R = Bn)
9(b)αd1/9(b)αd2 (R = MOM)

10βd1/10βd2 (R = Bn)
10(b)αd1/10(b)αd2 (R = MOM)

a. CF$_3$CO$_2^-$+$_3$HN-Ala-Ala-OBn; PyBOP/NMM; DMF

Compound 10β: To a solution of compound 9βd1 (672 mg; 0.85 mmol) in DMF (9 mL) was added CF$_3$COO$^-$+H$_3$NAlaAlaOBn (340 mg; 1.10 mmol), PyBOP (953 mg; 1.83 mmol) and N-methylmorpholine (284 μL; 2.58 mmol). The reaction mixture was stirred for 48 h. Brine was then added and the reaction mixture was extracted with ethyl acetate. The combined organic phase was washed with an aqueous acid citric (10%) solution, water and aqueous NaHCO$_3$ (5%) solution. The organic layer was then dried over magnesium sulfate, filtered and evaporated. The crude residue was purified by chromatography (cyclohexane/ethyl acetate 90/10 to 40/60) to give compound 10βd1 (630 mg; 0.61 mmol), in 72% yield as a yellowish oil.

Compound 10βd2 (594 mg; 0.58 mmol) was prepared from compound 9βd2 (686 mg; 0.86 mmol) in 67% yield as a white solid, following the same procedure as for compound 10βd1.

10βd1/10βd2: C$_{59}$H$_{63}$F$_2$N$_3$O$_{11}$ M=1028.14 g·mol$^{-1}$

Mass (ESI$^+$):1028.19 (M+H); 1050.44 (M+Na)

NMR $^{19}$F (CDCl$_3$, 282.5 MHz) (with H coupled):

10βd1: −101.4/−102.3 (2m, 1F); −102.4/−103.5 (2m, 1F).

10βd2: −98.5/−99.5 (2m, 1F); −102.9/−104.0 (2m, 1F).

NMR $^{19}$F (CDCl$_3$, 282.5 MHz) (without H coupled):

10βd1: −102.0 (d, J=258 Hz, 1F); −103.0 (d, J=258 Hz, 1F).

9βd2: −99.0 (d, J=258 Hz, 1F); −103.4 (d, J=258 Hz, 1F).

Compound 10(b)α: The compound 10(b)αd1 (m=910 mg, n=0.93 mmol, yield=85%) was prepared from compound 9(b)αd1 (818 mg, 1.09 mmol, 1 eq) following the same procedure as for compound 10βd1.

The compound 10(b)αd2 (m=845 mg, n=0.86 mmol, yield=79%) was prepared from compound 9(b)αd2 (818 mg, 1.09 mmol, 1 eq) following the same procedure as for compound 10βd1.

10(b)αd1/10(b)αd2: C$_{54}$H$_{61}$F$_2$N$_3$O$_{12}$ M=982.07 g·mol$^{-1}$

10(b)αd1

Mass (ESI$^+$): 982.4 [M+H]$^+$, 999.5 [M+H$_2$O]$^+$

NMR $^{19}$F (CDCl$_3$, 282.5 MHz) (with H coupled): −97.9/−99.2 (1F; 2m); −103.4/−104.6 (1F; 2m)

NMR $^{19}$F (CDCl$_3$, 282.5 MHz) (without H coupled): −98.6 (1F; d; J=261 Hz); −104.0 (1F; d; J=261 Hz)

10(b)αd2

Mass (ESI$^+$): 982.4 [M+H]$^+$, 999.5 [M+H$_2$O]$^+$, 1004.4 [M+Na]$^+$

NMR $^{19}$F (CDCl$_3$, 282.5 MHz) (with H coupled): −97.5/−98.8 (1F; 2m); −104.4/−105.6 (1F; 2m)

NMR $^{19}$F (CDCl$_3$, 282.5 MHz) (without H coupled): −98.1 (1F; d; J=260 Hz); −105.0 (1F; d; J=260 Hz)

Synthesis of Compounds 11β (11βd1/11βd2)

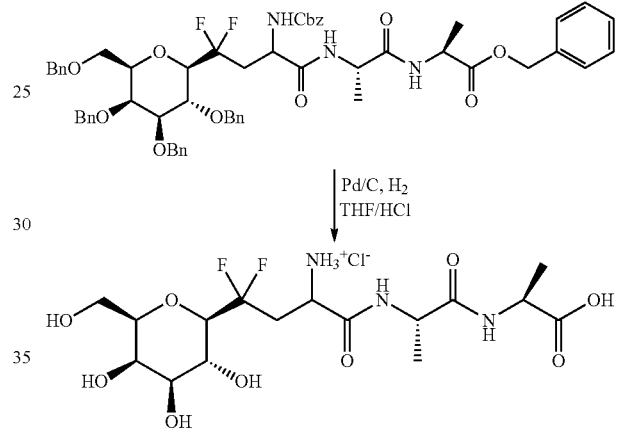

Compound 10βd1 (395 mg; 0.38 mmol) dissolved in a mixture of THF (12 mL) and HCl 1N (1.4 mL) and in the presence of Pd/C 10% was placed under a hydrogen atmosphere. The mixture was stirred for 48 h, then Millipore-filtered and evaporated to give compound 11βd1 (182 mg, 0.38 mmol, yield 100%) quantitatively as a white solid.

Compound 11βd2 (187 mg, 0.39 mmol, yield 100%) was prepared as a white solid in quantitative yield from compound 10βd2 (399 mg; 0.39 mmol) following the same procedure as for compound 11βd1.

11βd1/11βd2: C$_{16}$H$_{28}$ClF$_2$N$_3$O$_9$ M=479.86 g·mol$^{-1}$

Mass (ESI$^+$): 442.1 (M−HCl)

NMR $^{19}$F (D$_2$O, 282.5 MHz) (with H coupled):

11βd1: −102.2/−103.3 (m, 1F); −108.4/−109.5 (m, 1F).

11βd2: −102.8/−103.7 (m, 1F); −107.4/−108.4 (m, 1F).

NMR $^{19}$F (D$_2$O, 282.5 MHz) (without H coupled):

11βd1: −102.7 (d, J=258 Hz, 1F); −108.9 (d, J=258 Hz, 1F)

11βd2: −103.3 (d, J=257 Hz, 1F); −107.9 (d, J=257 Hz, 1F).

Synthesis of compounds 12(b)α (12(b)αd1/12(b)αd2)

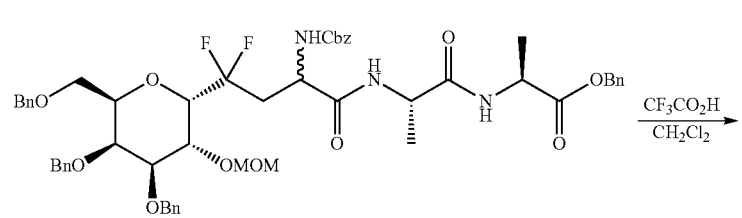

-continued

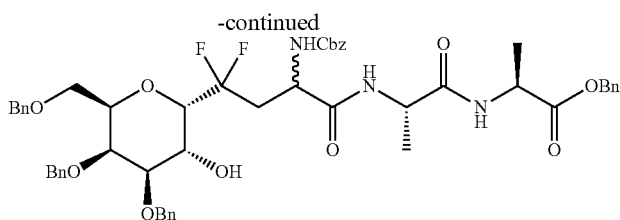

Compound 12(b)α: Trifluoroacetic acid (3.4 mL, 45.6 mmol) was added dropwise to a solution of compound 10(b)αd1 (675 mg, 0.687 mmol, 1 eq) in dichloromethane (3.4 mL) under inert atmosphere. The reaction mixture was stirred for 3 h and was then poured into a NaHCO$_3$ saturated aqueous solution. The obtained solution was extracted two times with dichloromethane and the combined organic layers were dried over sodium sulfate, filtered and concentrated. Purification of the crude residue by flash column chromatography (cyclohexane/AcOEt 65/35 to 25/75) afford compound 12(b)αd1 (m=385 mg, n=0.41 mmol, yield=60%) as a white solid.

The compound 12(b)αd2 (m=368 mg, n=0.39 mmol, yield=60%) was prepared from compound 10(b)αd2 (642 mg, 0.654 mmol, 1 eq) following the same procedure as for compound 12(b)αd1.

12(b)αd1/12(b)αd2: $C_{52}H_{57}F_2N_3O_{11}$ M=938.02 g·mol$^{-1}$
12(b)αd1
Mass (ESI$^+$): 938.4 [M+H]$^+$, 955.4 [M+H$_2$O]$^+$, 960.4 [M+Na]$^+$
NMR $^{19}$F (CDCl$_3$, 282.5 MHz) (with H coupled): −97.3/−98.6 (1F; 2m); −101.6/−102.7 (1F; 2m)
NMR $^{19}$F (CDCl$_3$, 282.5 MHz) (without H coupled): −97.9 (1F; d; J=262 Hz); −102.1 (1F; d; J=262 Hz
12(b)αd2
Mass (ESI$^+$): 938.4 [M+H]$^+$ 955.4 [M+H$_2$O]$^+$, 960.4 [M+Na]$^+$
NMR $^{19}$F (CDCl$_3$, 282.5 MHz) (with H coupled): 97.3/−98.5 (1F; 2m); −103.6/−104.7 (1F; 2m)
NMR $^{19}$F (CDCl$_3$, 282.5 MHz) (without H coupled): −97.9 (1F; d; J=259 Hz); −104.1 (1F; d; J=259 Hz)

Synthesis of Compounds 13(b)α (13(b)αd1/13(b)αd2)

Compound 13(b)α: Compound 12(b)αd1 (395 mg, 0.42 mmol, 1 eq) dissolved in a mixture of THF (13.2 mL) and HCl 1N (1.5 mL) and in the presence of Pd/C 10% (112 mg, 0.25 eq) was placed under a hydrogen atmosphere. The mixture was stirred for 24 h, then Millipore-filtered and evaporated to give compound 13(b)αd1 (m=197 mg, n=0.41 mmol, yield=97%)

The compound 13(b)αd2 (m=172 mg, n=0.36 mmol, yield=100%) was prepared from compound 12(b)αd2 (338 mg, 0.36 mmol, 1 eq) following the same procedure as for compound 13(b)αd1.

13(b)αd1/13(b)αd2: $C_{16}H_{28}ClF_2N_3O_9$ M=479.86 g·mol$^{-1}$
13(b)αd1
Mass (ESI$^+$): 444.2 [M−HCl+H]$^+$, 466.2 [M−HCl+Na]$^+$, 482.1 [M−HCl+K]$^+$
NMR $^{19}$F (CDCl$_3$, 282.5 MHz) (with H coupled): −97.2/−98.4 (1F; 2m); −101.8/−103.0 (1F; 2m)
NMR $^{19}$F (CDCl$_3$, 282.5 MHz) (without H coupled): −97.8 (1F; d; J=256 Hz); −102.4 (1F; d; J=256 Hz)
13(b)αd2
Mass (ESI$^+$): 444.2 [M−HCl+H]$^+$, 466.2 [M−HCl+Na]$^+$, 482.1 [M−HCl+K]
NMR $^{19}$F (CDCl$_3$, 282.5 MHz) (with H coupled): −97.7/−98.8 (1F; 2m); −100.5/−101.8 (1F; 2m)
NMR $^{19}$F (CDCl$_3$, 282.5 MHz) (without H coupled): −98.2 (1F; d; J=257 Hz); −101.0 (1F; d; J=257 Hz)

Synthesis of Compounds 15

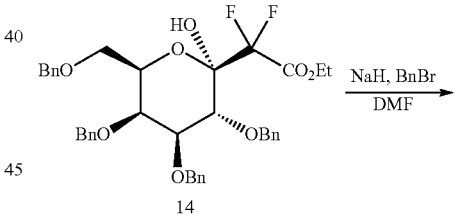

14

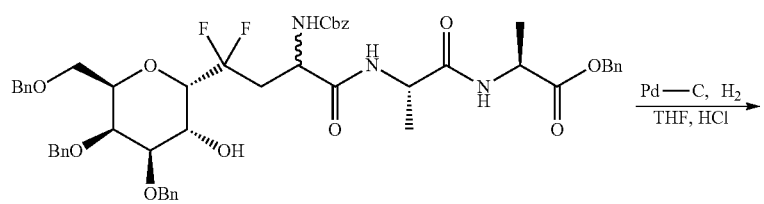

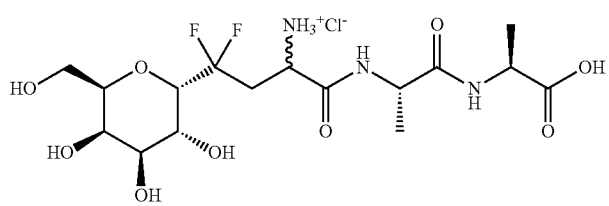

Synthesis of Compounds 17d1/17d2

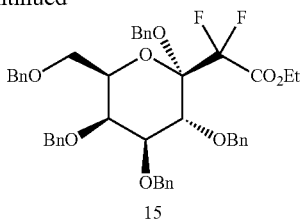

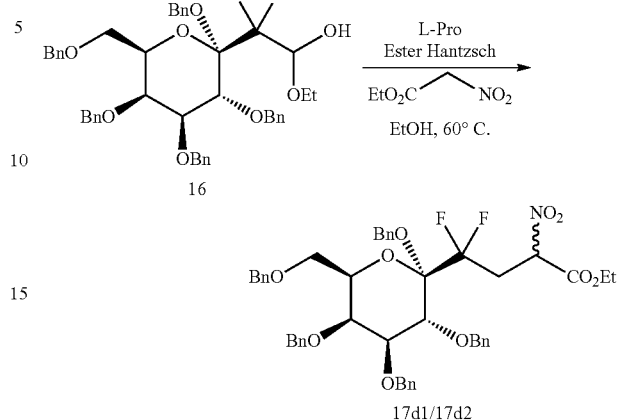

Compound 15: Compound 14 (3 g, 4.50 mmol, 1 eq) obtained from a process described in *Synlett* 2005, 17, 2627-2630 —see also WO 2004/014928, WO 2007/125203 and WO 2007/125194 was dissolved in anhydrous DMF (45 mL). The solution was cooled to 0° C. and sodium hydride (129 mg, 5.40 mmol, 1.2 eq) was added portion wise. After 45 min. stirring at 0° C., benzyl bromide (1.1 mL, 9 mmol, 2 eq.) was added drop wise. The reaction mixture was warmed to room temperature and stirred 5 h 30. A saturated aqueous solution of ammonium chloride was added and the mixture was extracted three times with ethyl acetate. The combined organic layers were washed with water, then with brine before being dried and evaporated. Purification by chromatography (cyclohexane/ethyl acetate 98/2 to 75/25) afford compound 15 (m=2.61 mg, n=3.47 mmol, yield=77%).

15: $C_{45}H_{46}F_2O_8$ M=752.84 g·mol$^{-1}$
Mass (ESI$^+$): 775.4 [M+Na]$^+$, 791.3 [M+K]$^+$
NMR $^{19}$F (CDCl$_3$, 282.5 MHz) (with H coupled): −111.4 (1F; d; J=265 Hz); −116.1 (1F; d; J=265 Hz); −112.0 (1F; d; J=263 Hz); −115.3 (1F; dd; J=265 Hz; J=3 Hz Synthesis of Compounds 16

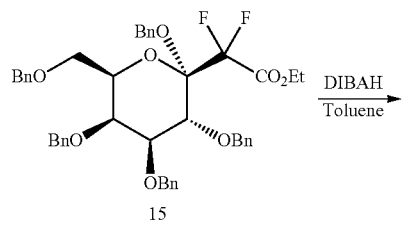

To a cooled (−78° C.) solution of Compound 15 (1.34 g, 1.78 mmol, 1 eq) in anhydrous toluene (18 mL) was added a solution of diisobutylaluminium hydride (1.2M in toluene; 2.15 mL; 2.58 mmol; 1.45 eq.) and the resultant mixture was stirred for 5 h at this temperature. The reaction was then quenched with methanol (4 mL) and the solution was warmed to −20° C. for 10 min. A Rochelle's salt solution (20%) was then added and the solution was vigorously stirred for 1 h. The reaction medium was extracted with ethyl acetate. The combined organic extracts were washed with brine, dried over magnesium sulfate, filtered and evaporated in vacuo to give compound 16 (m=1.3 g, yellow oil). Compound 16 was used in the next step without further purification.

16: $C_{45}H_{48}F_2O_8$ M=754.85 g·mol$^{-1}$
Mass (ESI$^+$): 777.4 [M+Na]$^+$, 793.3 [M+K]$^+$ Compound 17: To a mixture of compound 16 (1.56 g, 2.07 mmol, 1 eq), L-proline (L-Pro) (119 mg, 1.04 mmol, 0.5 eq) and Hantzsch ester (70 mg, 2.69 mmol, 1.3 eq) in ethanol (20 ml) was added ethyl nitroacetate (0.3 mL, 3.11 mmol, 1.5 eq). The reaction mixture was stirred 20 hours at 60° C. Ether was added and the organic phase was washed three times with water, dried over sodium sulfate, filtered and evaporated. The residue was then purified by chromatography (cyclohexane/ethyle acetate 80/20) to give compound 17 (17d1/17d2 60/40) (m=1.3 g, 1.57 mmol, yield=75%, yellow solid) as a mixture of diastereomer.

17d1/17d2: $C_{47}H_{49}F_2NO_{10}$ M=825.89 g·mol$^{-1}$
Mass (ESI$^+$): 843.4 [M+H$_2$O]$^+$, 848.3 [M+Na]$^+$, 864.3 [M+K]$^+$ Synthesis of Compounds 18d1/18d2

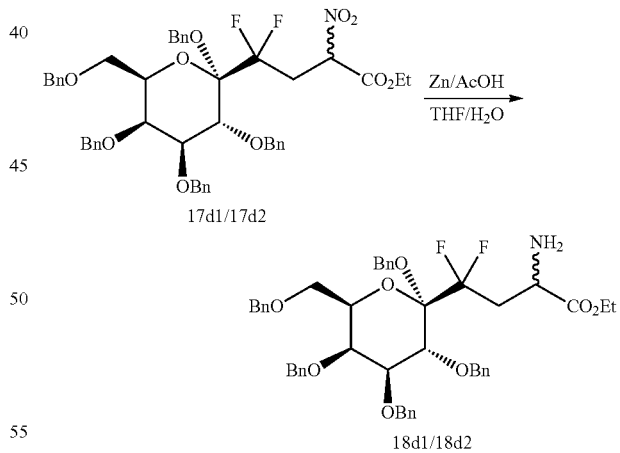

Compound 18: To a solution of compound 17d1/17d2 (17d1/17d2 60/40) (1.23 g, 1.55 mmol, 1 eq) in THF (4.9 mL), water (7.3 mL) and acetic acid (7.3 mL), was added Zn dust (2.1 g; 32.5 mmol; 21 eq.). The resultant mixture was stirred at room temperature for 5 hours. The reaction mixture was filtered through Celite and concentrated. A solution of NaHCO$_3$ was added to adjust the pH of the aqueous layer to pH8, and the resultant aqueous layer was then extracted with ethyl acetate. The combined organic phase was dried (MgSO$_4$), filtered, and concentrated. The crude mixture was purified by chromatography on silica gel (cyclohexane/ethyl acetate 80/20) to give compound 18 (18d1/18d2 60/40) (m=780 mg, n=0.98 mmol, yield=63%).

18d1/18d2: $C_{47}H_{51}F_2NO_8$ M=795.91 g·mol$^{-1}$

Mass (ESI$^+$): 796.4 [M+H]$^+$, 818.4 [M+Na]$^+$, 834.4 [M+K]$^+$

Synthesis of Compounds 19d1/19d2

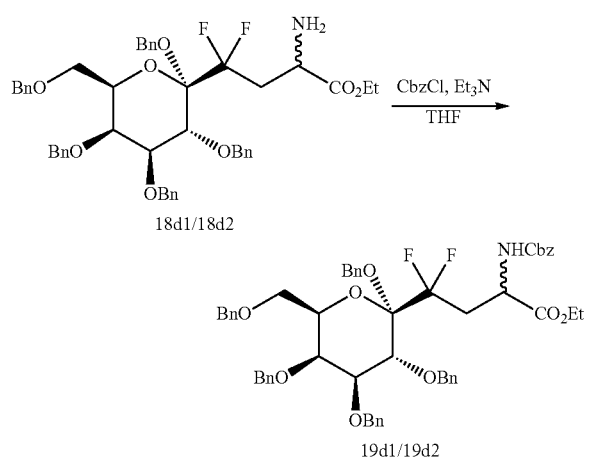

Compound 19: To a chilled (0° C.) solution of compound 18 (18d1/18d2 60/40) (658 mg, 0.827 mmol, 1 eq) in THF (8 mL) was added benzyl chloroformate (300 µL; 2.07 mmol; 2.5 eq.) and triethylamine (290 µL; 2.07 mmol; 2.5 eq.). The resultant mixture was stirred for 24 h and then extracted with ethyl acetate, washed with a saturated aqueous NaHCO$_3$ solution, dried (MgSO$_4$), filtered and evaporated. The crude residue was purified by chromatography (cyclohexane/ethyl acetate 2/98 to 80/20) to give compound 19 (19d1/19d2 60/40) (m=592 mg, n=0.637 mmol, yield=77%).

19d1/19d2: $C_{55}H_{57}F_2NO_{10}$ M=930.04 g·mol$^{-1}$

Mass (ESI$^+$): 947.44 [M+NH$_4$]$^+$, 953 [M+Na]$^+$, 968.37 [M+K]$^+$

Synthesis of Compounds 20d1/20d2

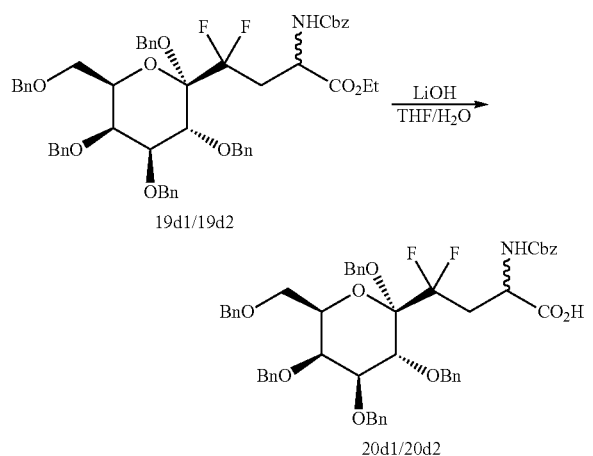

Compound 20: To a solution of compound 19 (19d1/19d2 60/40) (575 mg, 0.618 mmol, 1 eq) in THF (6 mL) was added LiOH 2N solution (0.93 mL; 1.85 mmol, 3 eq.). The solution was stirred for 12 hours then quenched with 1N HCl aqueous solution. The reaction mixture was then extracted with ethyl acetate, dried over sodium sulfate, filtered and evaporated to give compound 20 (20d1/20d2 55/45) as a white solid (m=526 mg, n=0.583 mmol, yield=94%).

20d1/20d2: $C_{53}H_{53}F_2NO_{10}$ M=901.99 g·mol$^{-1}$

Mass (ESI$^+$): 919.4 [M+H$_2$O]$^+$, 924.4 [M+Na]$^+$, 940.3 [M+K]$^+$

Synthesis of Compounds 21d1/21d2

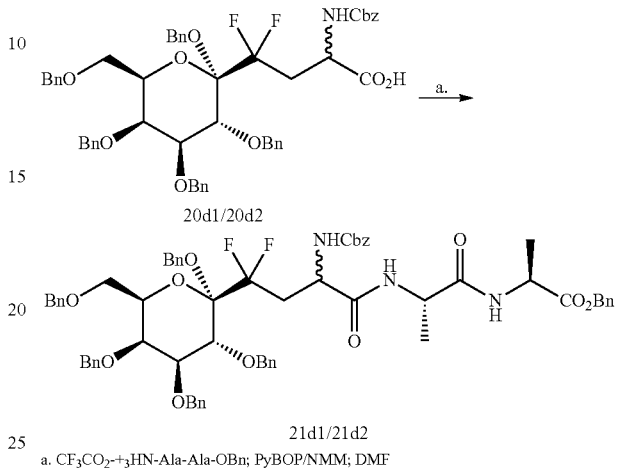

a. CF$_3$CO$_2^-$·$^+_3$HN-Ala-Ala-OBn; PyBOP/NMM; DMF

Compound 21: To a solution of compound 20 (20d1/20d2 55/45) (432 mg, 0.477 mmol, 1 eq) in DMF (4.6 mL) was added CF$_3$COO$^-$ $^+$H$_3$NAlaAlaOBn (223 mg; 0.612 mmol, 1.3 eq.), PyBOP (510 mg; 1 mmol, 2.1 eq.) and N-methylmorpholine (160 µL; 1.43 mmol, 3 eq.). The reaction mixture was stirred for 18 h. Brine was then added and the reaction mixture was extracted with ethyl acetate. The combined organic phase was washed with an aqueous acid citric (10%) solution, water and aqueous NaHCO$_3$ (5%) solution. The organic layer was then dried over sodium sulfate, filtered and evaporated. The crude residue was purified by chromatography (cyclohexane/ethyl acetate 4/96 to 60/40) to give compound 21 (21d1/21d2 55/45) as a colourless oil (m=453 mg, n=0.4 mmol, yield=84%).

21d1/21d2: $C_{66}H_{69}F_2N_3O_{12}$ M=1134.26 g·mol$^{-1}$

Mass (ESI$^+$): 1134.5 [M+H]$^+$, 1151.5 [M+H$_2$O]$^+$, 1156.5 [M+Na]$^+$, 1172.5 [M+K]$^+$ NMR $^{19}$F (CDCl$_3$, 282.5 MHz) (without H coupled): −102.9 (1F; d; J=259 Hz); −103.2 (1F; d; J=259 Hz), −104.6 (1F; d; J=259 Hz); −104.8 (1F; d; J=259 Hz)

Synthesis of Compounds 22d1/22d2

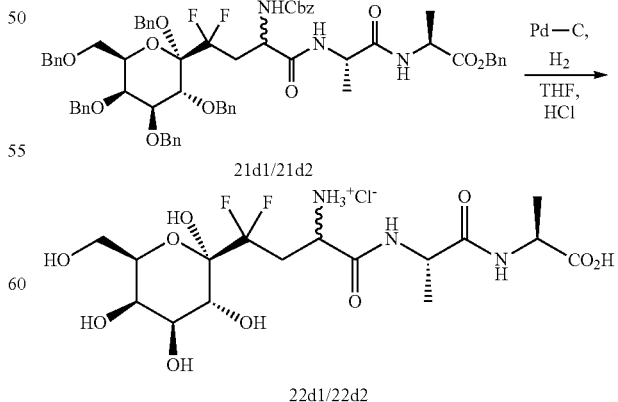

Compound 22: Compound 21 (21d1/21d2 55/45) (51 mg; 0.045 mmol) dissolved in a mixture of THF and HCl 1N (590

μL) and in the presence of Pd/C 10% was placed under a hydrogen atmosphere. The mixture was stirred for 48 h, then Millipore-filtered and evaporated to give compound 22 (m=22 mg, n=0.044 mmol, yield=99%).

22d1/22d2: $C_{16}H_{28}ClF_2N_3O_{10}$ M=495.86 g·mol$^{-1}$

Mass (ESI$^+$): 459.2[M−HCl+H]$^+$, 477.2 [M−HCl+H$_2$O]$^+$

Synthesis of Compounds 23d1/23d2

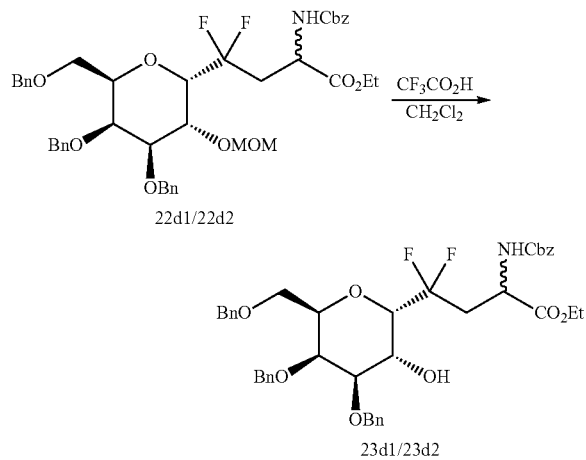

Compound 23d1 (174 mg, 0.24 mmol, yield 52%) was prepared from compound 8(b)αd1 (m=355 mg, n=0.46 mmol) following the same procedure as for compound 12(b)α.

Compound 23d2 (228 mg, 0.31 mmol, yield 60%) was prepared from compound 8(b)αd2 (m=402 mg, n=0.52 mmol) following the same procedure as for compound 12(b)α.

23d1/23d2: $C_{41}H_{45}F_2NO_9$ M=733.79 g·mol$^{-1}$

23d1

Masse (ESI$^+$): 756.4 [M+Na]$^+$, 772.4 [M+K]$^+$

NMR $^{19}$F (CDCl$_3$, 282.5 MHz) (with H coupled): −102.3/−103.5 (1F; 2m); −103.5/−104.7 (1F; 2m)

NMR $^{19}$F (CDCl$_3$, 282.5 MHz) (without H coupled): −102.9 (1F; d; J=259 Hz); −104.2 (1F; d; J=259 Hz)

23d2

Mass (ESI$^+$): 756.4 [M+Na]$^+$, 772.4 [M+K]$^+$

NMR $^{19}$F (CDCl$_3$, 282.5 MHz) (with H coupled): −99.3/−100.6 (1F; 2m); −104.9/−106.2 (1F; 2m)

NMR $^{19}$F (CDCl$_3$, 282.5 MHz) (without H coupled): −99.9 (1F; d; J=254 Hz); −105.5 (1F; d; J=254 Hz)

Synthesis of Compounds 24d1/24d2

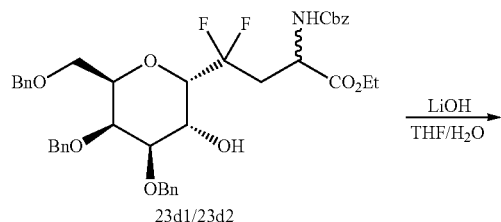

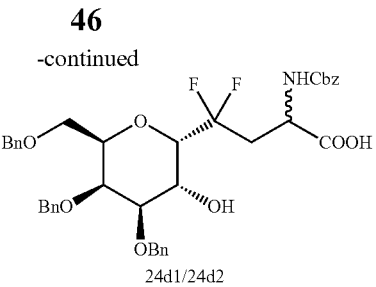

Compound 24d1 (77 mg, 0.11 mmol, yield 100%) was prepared from compound 23d1 (m=80 mg, n=0.11 mmol) following the same procedure as for compound 9(b)αd1.

Compound 24d2 (77 mg, 0.11 mmol, yield 100%) was prepared from compound 23d1 (m=80 mg, n=0.11 mmol) following the same procedure as for compound 9(b)αd1.

24d1/24d2: $C_{39}H_{41}F_2NO_9$ M=705.74 g·mol$^{-1}$

24d1

Masse (ESI$^+$): 706.3 [M+H]$^+$, 723.3 [M+H$_2$O]$^+$, 728.3 [M+Na]$^+$

NMR $^{19}$F (CDCl$_3$, 282.5 MHz) (with H coupled): −100.8/−101.9 (1F; 2m); −102.2/−103.4 (1F; 2m)

NMR $^{19}$F (CDCl$_3$, 282.5 MHz) (without H coupled): −101.3 (1F; d; J=262 Hz); −102.9 (1F; d; J=262 Hz)

24d2

Mass (ESI$^+$): 706.3 [M+H]$^+$, 723.3 [M+H$_2$O]$^+$, 728.3 [M+Na]$^+$

NMR $^{19}$F (CDCl$_3$, 282.5 MHz) (with H coupled): −98.2/−99.3 (1F; 2m); −104.4/−105.7 (1F; 2m)

NMR $^{19}$F (CDCl$_3$, 282.5 MHz) (without H coupled): −98.7 (1F; d; J=260 Hz); −105.0 (1F; d; J=260 Hz)

Synthesis of Compounds 25d1/25d2

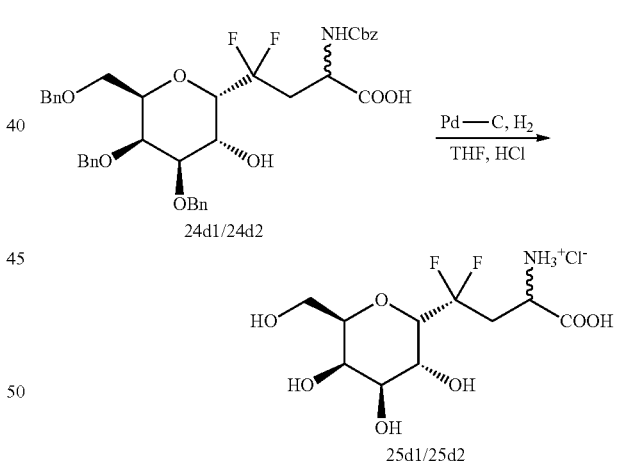

Compound 25d1 (35 mg, 0.11 mmol, yield 100%) was prepared from compound 24d1 (m=74 mg, n=0.11 mmol) following the same procedure as for compound 13(b)α.

Compound 25d2 (32 mg, 0.09 mmol, yield 93%) was prepared from compound 24d1 (m=72 mg, n=0.10 mmol) following the same procedure as for compound 13(b)α.

25d1/25d2: $C_{10}H_{18}ClF_2NO_7$ M=337.70 g·mol$^{-1}$

25d1

Masse (ESI$^+$): 302.1 [M−HCl+H]$^+$

NMR $^{19}$F (CDCl$_3$, 282.5 MHz) (with H coupled): −97.2/−98.3 (1F; 2m); −101.9/−103.0 (1F; 2m)

NMR $^{19}$F (CDCl$_3$, 282.5 MHz) (without H coupled): −97.7 (1F; d; J=256 Hz); −102.4 (1F; d; J=256 Hz)

25d2
Mass (ESI+): 302.1 [M−HCl+H]+
NMR 19F (CDCl3, 282.5 MHz) (without H coupled): −97.9 (1F; d; J=257 Hz); −100.9 (1F; d; J=257 Hz)

Synthesis of Compounds 27

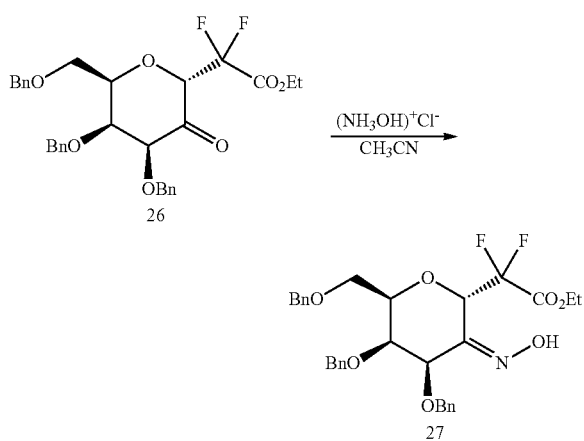

Compound 26 (24.2 g, 43.6 mmol, 1 eq) obtained from a process described in *Org. Lett.* 2007, 9, 2477-2480 was dissolved in acetonitrile (58 mL) and the obtained solution was added to a solution of hydroxylamine hydrochloride (5.46 g, 78.5 mmol, 1.8 eq) and sodium acetate (7.15 g, 87.2 mmol, 2 eq) in water (58 mL). The reaction mixture was stirred at room temperature overnight before being evaporated and purified by chromatography (cyclohexane/ethyl acetate 100/0 to 70/30) to give compound 27 (m=11.59 g, n=20.3 mmol, yield=47%) as a yellow oil.

27: $C_{31}H_{33}F_2NO_7$ M=569.59 g·mol$^{-1}$
Mass (ESI+): 570.2 [M+H]+
NMR 19F (CDCl3, 282.5 MHz) (with H coupled): −109.5 (1F; dd; J=255 Hz; J=9 Hz); −113.1 (1F; dd; J=255 Hz; J=23 Hz)
NMR 19F (CDCl3, 282.5 MHz) (without H coupled): −109.5 (1F; d; J=255 Hz); −113.1 (1F; d; J=255 Hz)

Synthesis of Compounds 28G/28T

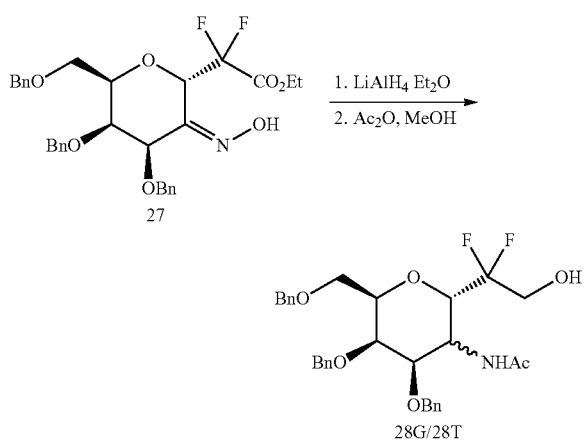

A solution of compound 27 (5.5 g, 9.66 mmol, 1 eq) in diethyl ether (250 mL) was added drop wise to a suspension of lithium aluminium hydride (3.67 g, 96.6 mmol, 10 eq) in diethyl ether (150 mL) under inert atmosphere. The suspension was stirred for 10 min at room temperature and then refluxed overnight before being cooled to 0° C. A Rochelle's salt aqueous solution was carefully added drop wise. The mixture was then warmed to room temperature and filtered through a pad of Celite. The pad was washed with diethyl ether. The layers were separated and the aqueous one was extracted with diethyl ether. The combined organic layers were washed with water, dried over sodium sulfate and evaporated. The yellow crude residue obtained was dissolved in methanol (700 mL) and acetic anhydride (10.8 mL, 115 mmol, 12 eq) was added. The reaction mixture was stirred at room temperature for 1.5 h, then evaporated to give a mixture of two diastereomers (28T/28G 70/30). Each diastereomer has been isolated by chromatography (cyclohexane/ethyl acetate 60/40 to 35/65) of the crude residue 28T (m=1.65 g, n=2.97 mmol, yield=31%) and 28G (m=516 mg, n=0.93 mmol, yield=10%).

28T/28G: $C_{31}H_{35}F_2NO_6$ M=555.61 g·mol$^{-1}$

28T
Mass (ESI+): 562.3 [M+Li]+
NMR 19F (CDCl3, 282.5 MHz) (with H coupled): −109.5/−110.7 (1F; 2m); −112.9/−114.6 (1F, 2m)
NMR 19F (CDCl3, 282.5 MHz) (without H coupled): −110.1 (1F; d; J=261 Hz); −113.7 (1F; d; J=261 Hz)

28G
Mass (ESI+): 562.3 [M+Li]+ 578.2 [M+Na]+
NMR 19F (CDCl3, 282.5 MHz) (with H coupled): −112.2/−113.7 (1F; 2m); −120.3/−121.7 (1F; 2m)
NMR 19F (CDCl3, 282.5 MHz) (without H coupled): −112.8 (1F; d; J=269 Hz); −120.8 (1F; d; J=269 Hz)

Synthesis of Compounds 29G

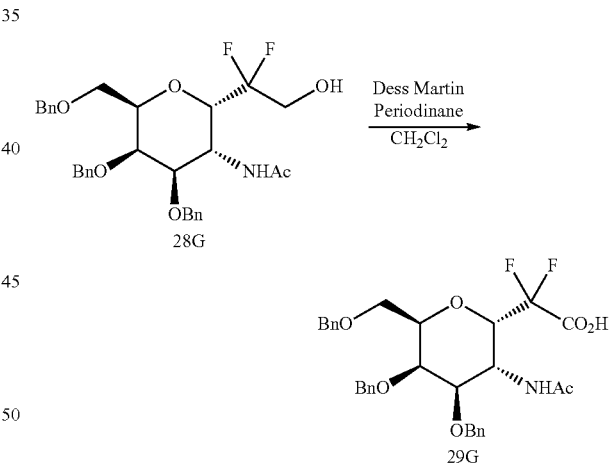

Compound 28G (200 mg, 0.36 mmol, 1 eq) was dissolved in dichloromethane (1 mL) under inert atmosphere and Dess Martin periodinane (458 mg, 1.08 mmol, 3 eq) was added. The reaction mixture was stirred at room temperature overnight. Dichloromethane and water were added and the layers separated. The aqueous layer was extracted with dichloromethane and the combined organic layers were dried over sodium sulfate. Evaporation and purification by chromatography (dichloromethane/methanol 90/10 to 85/15) afford compound 29G (m=45 mg, n=0.079 mmol, yield=22%)

29G: $C_{31}H_{33}F_2NO_7$ M=569.59 g·mol$^{-1}$
Mass (ESI+): 570.2 [M+H]+, 592.2 [M+Na]+, 608.1 [M+K]+

Synthesis of Compounds 30G

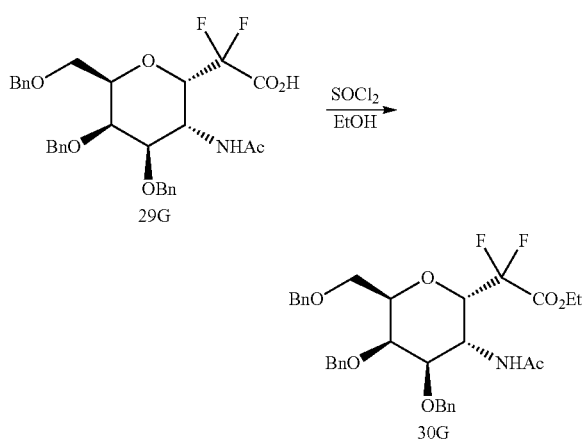

Thionyl chloride (21 µL, 0.278 mmol, 3.6 eq) was added to a solution of compound 29G (44 mg, 0.077 mmol, 1 eq) in ethanol (510 µL). The reaction mixture was refluxed 1 h, then cooled and slowly added to an aqueous saturated solution of sodium hydrogenocarbonate. The solution was extracted two times with diethyl ether and the combined organic layers were dried over sodium sulfate. Evaporation and purification by chromatography afford compound 30G (m=6 mg, n=0.01 mmol, yield=13%)

30G: $C_{33}H_{37}F_2NO_7$ M=597.65 g·mol$^{-1}$

Mass (ESI$^+$): 598.3 [M+H]$^+$, 620.2 [M+Na]$^+$, 636.2 [M+K]$^+$

Synthesis of Compounds 31G

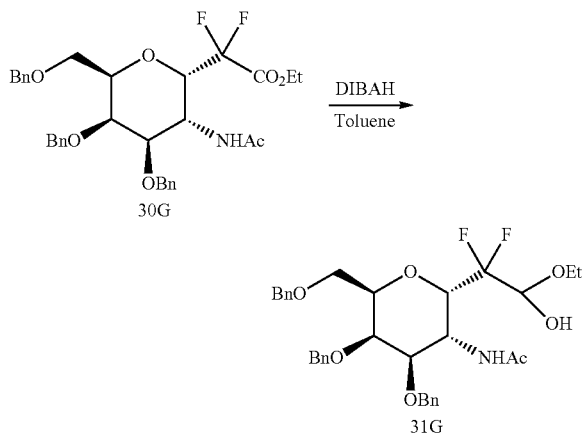

The compound 31G (m=702 mg, n=1.17 mmol, yield=89%) was prepared from compound 30G (790 mg, 1.32 mmol, 1 eq) following the same procedure as for compound 16. The crude mixture containing compound 31G is used in the next step without further purification and without characterization.

Synthesis of Compounds 32Gd1/32Gd2

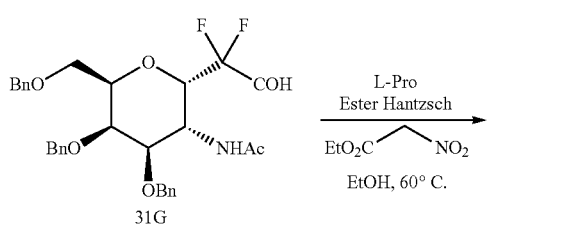

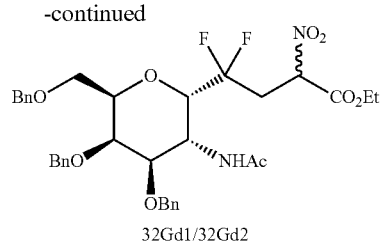

The compound 32Gd1/32Gd2 (m=365 mg, n=0.54 mmol, yield=47%) was prepared from compound 31G (702 mg, 1.17 mmol, 1 eq) following the same procedure as for compound 17.

32Gd1/32Gd2: $C_{35}H_{40}F_2N_2O_9$ M=670.70 g·mol$^{-1}$

Mass (ESI$^+$): 693.3 [M+Na]$^+$, 709.3 [M+K]$^+$

Synthesis of Compounds 33Gd1/33Gd2

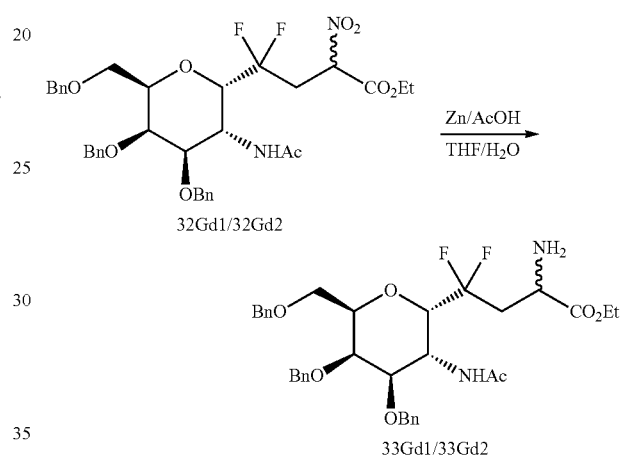

The compound 33Gd1/33Gd2 (m=332 mg, n=0.52 mmol, yield=96%) was prepared from compound 32Gd1/32Gd2 (362 mg, 0.54 mmol, 1 eq) following the same procedure as for compound 18. At this stage, both diastereomers could be isolated by purification on chromatography.

33Gd1/33Gd2: $C_{35}H_{42}F_2N_2O_7$ M=640.71 g·mol$^{-1}$

Mass (ESI$^+$): 641.4 [M+H]$^+$, 663.4 [M+Na]$^+$, 679.4 [M+K]$^+$

Synthesis of Compounds 34Gd1/34Gd2

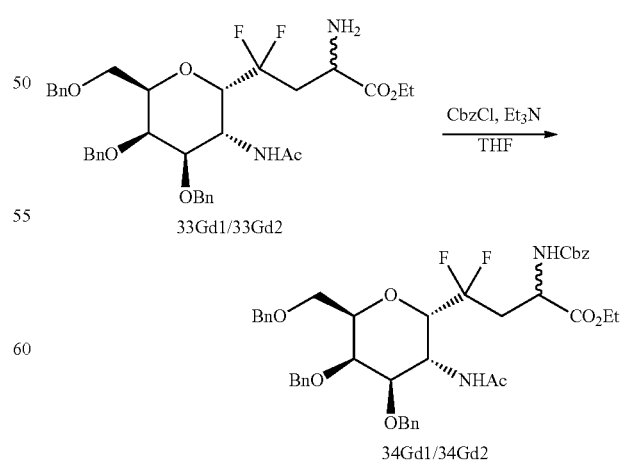

The compound 34Gd1/34Gd2 (m=51 mg, n=0.066 mmol, yield=28%) was prepared from compound 33Gd1/33Gd2

(150 mg, 0.23 mmol, 1 eq) following the same procedure as for compound 19.

34Gd1/34Gd2: $C_{43}H_{48}F_2N_2O_9$ M=774.85 g·mol$^{-1}$

Mass (ESI$^+$): 775.3 [M+H]$^+$, 792.3 [M+H$_2$O]$^+$, 797.3 [M+Na]$^+$, 813.3 [M+K]$^+$ Synthesis of Compounds 35Gd1/35Gd2

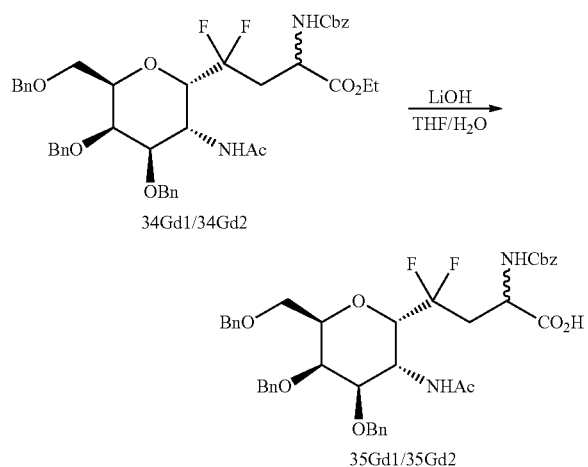

The compound 35Gd1/35Gd2 (m=48 mg, n=0.065 mmol, yield=100%) was prepared from compound 34Gd1/34Gd2 (50 mg, 0.65 mmol, 1 eq) following the same procedure as for compound 20.

35Gd1/35Gd2: $C_{41}H_{44}F_2N_2O_9$ M=746.79 g·mol$^{-1}$

Mass (ESI$^+$): 747.3 [M+H]$^+$, 764.3 [M+H$_2$O]$^+$, 769.3 [M+Na]$^+$, 785.3 [M+K]$^+$ Synthesis of Compounds 36Gd1/36Gd2

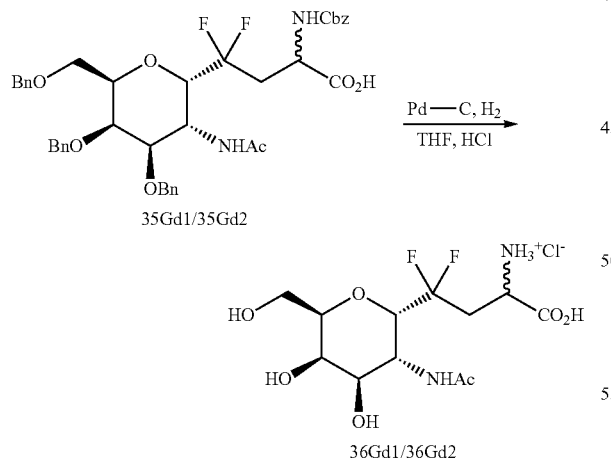

The compound 36Gd1/36Gd2 (m=24 mg, n=0.065 mmol, yield=100%) was prepared from compound 35Gd1/35Gd2 (48 mg, 0.065 mmol, 1 eq) following the same procedure as for compound 13(b)α.

36Gd1/36Gd2: $C_{12}H_{21}ClF_2N_2O_7$ M=378.75 g·mol$^{-1}$

Mass (ESI$^+$): 343.2 [M–HCl+K]$^+$, 360.2 [M+NH$_4$]$^+$, 365.2 [M+Na]$^+$

Synthesis of Compound 38

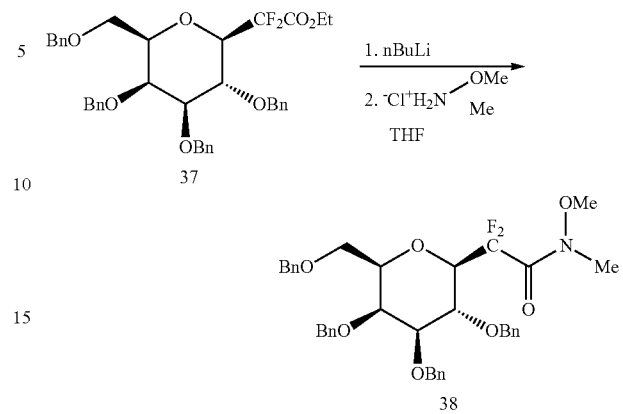

Into a round-bottom flask, under an inert atmosphere, BuLi (1.5 M, 1.6 mL, 5.7 eq.) is added carefully at −78° C. to a solution of Weinreb amine (122 mg; 1.25 mmol; 3 eq) in THF anhydrous (2.5 mL). The mixture is left under agitation for 20 minutes, with the media put back at room temperature. The compound 37 (271 mg; 0.420 mmol; 1 eq.) in THF (0.5 mL) is then added at −78° C. Then the media is allowed to get back to room temperature, and stirred for 30 minutes. The mixture is hydrolyzed with HCl 1N to obtained pH 7, extracted three times with Et$_2$O, dried over magnesium sulfate, filtered and then evaporated. The crude mixture containing compound 38 is used in the next step without further purification.

38: $C_{38}H_{41}F_2NO_7$ M=661.73 g·mol$^{-1}$

Mass (ESI$^+$): 684.4 (M+Na).

Synthesis of Compound 39

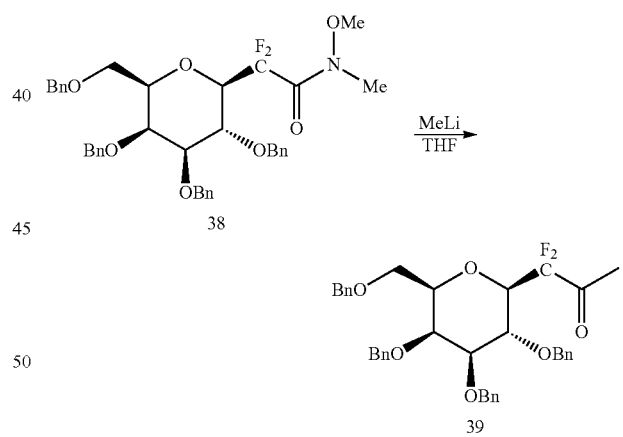

Into a round-bottom flask, under an inert atmosphere, MeLi (1.6 M solution in Et$_2$O, 0.9 mL, 4 eq.) was added at −78° C. to a solution of crude compound 38 (226 mg) in THF (5 mL). The mixture was stirred for 30 minutes. Then, a saturated aqueous solution of NH$_4$Cl was added and the mixture was extracted with Et$_2$O. The combined organic layers were dried over magnesium sulfate, filtered and evaporated. Then the residue was purified by chromatography (cyclohexane/ethyl acetate 93/7 to 40/60) to give compound 39 (120 mg, 0.20 mmol).

39: $C_{37}H_{38}F_2O_6$ M=616.69 g·mol$^{-1}$

Mass (ESI$^+$): 634.3 [M+H$_2$O]$^+$, 639.3 [M+Na]$^+$, 655.2 [M+K]$^+$.

NMR $^{19}$F (CDCl$_3$, 282.5 MHz): −115.5 (1F, dd, J=257 Hz, J=11 Hz); −119.6 (1F, ddd, J=257 Hz, J=11 Hz, J=3 Hz).

Synthesis of Compound 40

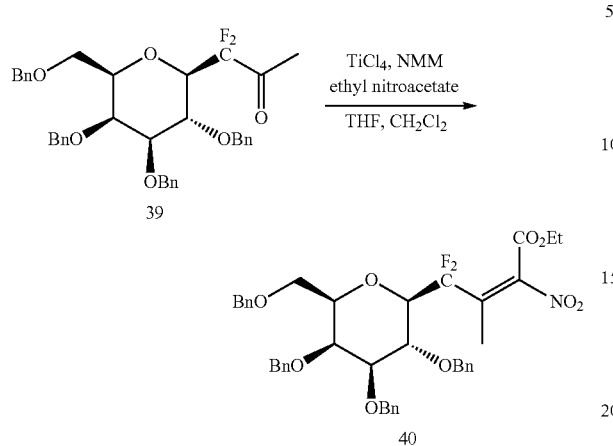

Under an inert atmosphere, a solution of ethyl nitroacetate (0.036 mL, 0.32 mmol) and compound 39 (100 mg, 0.16 mmol) in CH$_2$Cl$_2$ (1.5 mL) was added to a stirred solution of TiCl$_4$ (1M solution in CH$_2$Cl$_2$, 0.3 ml, 0.3 mmol) in anhydrous THF (2 mL) at 0° C. The mixture was stirred for 15 min at 0° C. and a solution of N-methyl morpholine (NMM) (0.071 mL, 0.65 mmol) in THF (1 mL) was added. Then the reaction mixture was stirred for an additional time of 15 min. at 0° C., allowed to warm to room temperature for 15 h and heated at 60° C. for 15 h. Then H$_2$O was added and the mixture was extracted with Et$_2$O. The combined organic layers were dried over magnesium sulfate, filtered and evaporated.

40: C$_{41}$H$_{43}$F$_2$NO$_9$ M=731.78 g·mol$^{-1}$

Mass (ESI$^+$): 732.28 [M+H]$^+$; 749.33[M+H$_2$O]$^+$.

II—Stability of Pseudo Glycosidic Bond

Compound 11βd1, 11βd2, 12(b)αd1, 12(b)αd2, 25d1 and 25d2 have all been neutralized using the following process before to be used in the stability test described below.

Compound 11βd1 (196 mg, 0.41 mmol) was dissolved in methanol (3 mL). Ion exchange resin (Amberlite IRA-67 weakly basic, previously washed with water, then with methanol) was added and the suspension thus obtained was stirred for 30 min. The mixture was filtered and the resin washed with methanol (10 mL). Evaporation, dissolution in water (25 mL) and freeze drying afford compound Ad1 (120 mg, 0.27 mmol, yield 66%) as a white solid.

Using the previous process, compound 11βd2 leads to compound Ad2, compound 12(b)αd1 leads to compound Dd1, compound 12(b)αd2 leads to compound Dd2, compound 25d1 leads to compound Ed1 and compound 25d2 leads to compound Ed2.

Stability of β-Gal-CF$_2$-Ser Pseudo-glycosidic Bond

The enzymatic stability has been performed with compound Ad1 and Ad2 according to the invention and compound B used as a reference compound to control the efficacy of the β-galactosidase. Both compounds have been treated with β-galactosidase. The stability of compound Ad1 and Ad2 has been assessed by mass spectrum (MS) analysis after incubation with β-galactosidase. The samples have been injected and ionized by electrospray (ES) (in positive and negative mode). The procedure has been adapted from Maljaars et al. J. Comb. Chem. 2006, 8, 812-819.

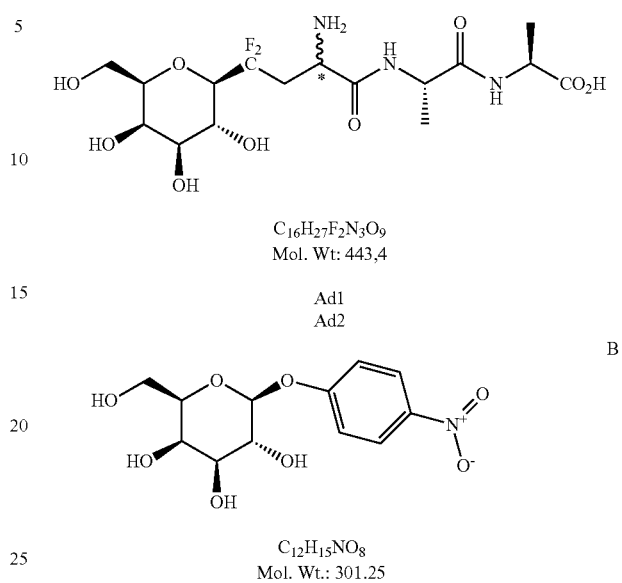

Test compound Ad1 (12 μmol, 5.3 mg) in 1.5 mL ammonium acetate buffer (10 mM, pH 7) was kept 24 h at 37° C. in the presence and absence of β-galactosidase (4.5 U, 32 μL of a 1 mg·mL$^{-1}$ solution in ammonium acetate buffer, (48275 sigma, 140 U per mg)). 300 μL of the sample was filtered through a 3-kDa-cutoff centrifugal filter (Millipore), and the filter was washed with H$_2$O (2×300 μL). The obtained solutions were diluted in water/methanol 1:1 (3 μL in 1 mL).

Test compound Ad2 (12 μmol, 5.3 mg) has been treated in the presence and absence of β-galactosidase following the same process.

These samples of compound Ad1 and Ad2 in presence of β-galactosidase have been submitted to mass spectra and compared to the mass spectra of compound Ad1 and Ad2 in absence of β-galactosidase. For both compound Ad1 (FIGS. 1a and 1b) and Ad2 (FIGS. 2a and 2b), the spectra show that no hydrolysis occurs and that both compounds remain intact.

The two samples were also analyzed by F-NMR to confirm that the test compound Ad1 and Ad2 were not cleaved by the β-galactosidase.

In parallel, p-nitrophenyl-β-galactoside (compound B, 12 μmol, 3.6 mg) in 1.5 mL ammonium acetate buffer (10 mM, pH 7) was kept 24 h at 37° C. in the presence and absence of β-galactosidase (4.5 U, 32 μL of a 1 mg·mL$^{-1}$ solution in ammonium acetate buffer (48275 sigma, 140 U per mg)).

During the process in the presence of β-Galactosidase, a yellow coloration was observed that underlines the decomposition of compound B.

The optical density (OD) of the two samples was measured at 420 nm to verify that the β-galactosidase is working and that degradation occurs on compound B (OD$_{420}$ with β-galactosidase=1.5786/OD$_{420}$ without β-galactosidase=0.0465).

Stability of α-Gal-CF$_2$-Ser Pseudo-glycosidic Bond

The enzymatic stability has been performed with compounds Cd1, Cd2, Dd1 and Dd2 according to the invention and compound F was used as a reference compound to control the efficacy of the α-galactosidase. All the compounds have been treated with α-galactosidase. The stability of compounds Cd1, Cd2, Dd1 and Dd2 has been assessed by MS analysis after incubation with α-galactosidase. The procedure has been adapted from Maljaars et al. J. Comb. Chem. 2006, 8, 812-819.

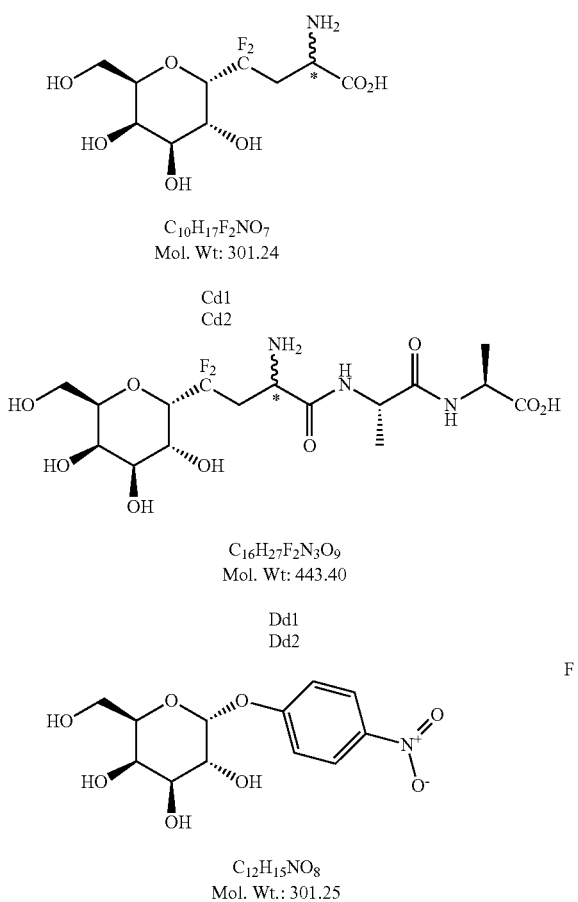

Cd1
Cd2

Dd1
Dd2

F

Test compound Cd1 (6 mol, 1.8 mg) in 0.75 mL ammonium acetate buffer (10 mM, pH 7) was kept 24 h at 37° C. in the presence and absence of α-galactosidase (2.25 U, 41 µL of a 3.7 mg·mL$^{-1}$ suspension in ammonium sulphate (G8507 sigma, 14.7 U/mg)). 300 µL of the samples were filtered through a 3-kDa-cutoff centrifugal filter (Millipore) and the filter was washed with $H_2O$ (2×300 µL). The resultant solutions were diluted in water/methanol 1:1 (3 µL in 1 mL);

Test compound Cd2 (12 mol, 5.3 mg) has been treated in the presence and absence of α-galactosidase following the same process.

The samples of compound Cd1 and Cd2 in presence of α-galactosidase have been analyzed by mass spectrometry and their spectra compared to the mass spectra of compound Cd1 and Cd2 in absence of α-galactosidase. For both compound Cd1 (FIGS. 3a and 3b) and Cd2 (FIGS. 4a and 4b), the spectra underline that no hydrolysis occurs and that both compounds remain intact.

The two samples were also analyzed by F-NMR to confirm that the test compounds Cd1 and Cd2 were not cleaved by α-galactosidase.

The same procedure was applied to compound Dd1 (6 mol, 2.6 mg) and Dd2 (6 mol, 2.6 mg).

The samples of compound Dd1 and Dd2 in presence of α-galactosidase have been submitted to mass spectra and compared to the mass spectra of compound Dd1 and Dd2 in absence of α-galactosidase. For both compounds Dd1 (FIGS. 5a and 5b) and Dd2 (FIGS. 6a and 6b), the spectra underline that no hydrolysis occurs on both compounds that remain intact.

The two samples were also analyzed by F-NMR to confirm that the test compounds Dd1 and Dd2 were not cleaved by α-galactosidase.

In parallel, p-nitrophenyl-α-galactoside (compound F, 6 µmol, 1.8 mg) in 0.75 mL of ammonium acetate buffer (10 mM, pH 7) was kept 24 h at 37° C. in the presence and absence of α-galactosidase 2.25 U, 41 µL of a 3.7 mg·mL$^{-1}$ suspension in ammonium sulphate ((G8507 sigma) 14.7 U/mg). The OD of the two samples was measured at 420 nm to verify that the α-galactosidase is working and that degradation occurs on compound F ($OD_{420}$ with α-galactosidase=1.6303/$OD_{420}$ without α-galactosidase=0.0124).

In conclusion, we showed in these experiments that the $CF_2$ bond is stable and does not undergo hydrolysis in the presence of galactosidase. To the contrary the O-glycosidic bound has been shown to undergo hydrolysis in the presence of galactosidases (vide supra) and as described in the literature (vide infra). Indeed O-glycosidic amino acid such as O-glycosidic serine and threonine can be cleaved by glycosidases (cf Maljaars et al. J. Comb. Chem. 2006, 8, 812-819 and Allen et al. Biochem. J. 1978, 171, 665-674).

III—Effect of Glycopeptides 13(b)αd1 and 13(b)αd2 on the Preservation of Neonatal Skin Fibroblast Under Starvation Conditions Materials and Methods
Subculturing
  The neonatal human skin fibroblasts (Cell line: CCD-27SK, ATCC number CRL-1475) were grown with DMEM medium supplemented with Fetal Bovine Serum 10% final, antibiotics (Penicillin/Streptomycin) 1% final and Amphotericin B 0.1% final.
  Fibroblasts were grown in 75 cm$^2$ culture flask to 80% confluence, in 37° C. and 10% $CO_2$ incubator. The medium was changed every two days by 37° C. preheated fresh medium.
Starvation Medium
  This medium was composed of 45% subculture medium without Fetal Bovine Serum mixed with 55% of Phosphate Buffer Saline 1× containing EDTA (final concentration of 0.45 mM). This was referred to as serum free or starvation medium.
Product Preparation
  The compounds 13(b)αd1 and 13(b)αd2 (M=479.9 g/mol) were diluted in starvation medium to 5 mg/ml final and pH was adjusted at 7.4 by addition of NaOH 1N.
General Experimental Procedure
Assays on 96 Well Plates
  Fibroblast cells were concentrated to 2·10$^5$ cells/ml and 100 µl of cell suspension was added in wells of a 96-well plate and incubated in 37° C. and 10% $CO_2$ incubator for 4 hours.
  After cell adhesion the medium was changed and plates were incubated (37° C.-10% $CO_2$) to perform the assay as follow:
    1 plate for each sampling times: days D0, D3, D4, D5, D6, and D7
    3 wells for each condition (triplicate count) added with 120 µl of culture medium, starvation medium, 13(b) αd1 solution (5 mg/ml) or 13(b)αd2 solution (5 mg/ml)

Viability Assay
Cell Viability was evaluated by the Trypan blue exclusion technique based on the principle that live cells possess intact cell membranes that exclude the Trypan blue dye. So, only the dead cells are blue at microscopic observation.
For sampling, 110 µl of Trypan Blue (SIGMA T8154) was added to 110 µl of trypsinated cell suspension of matching well for counting.
200 µl of the trypan blue/cell mixture are dropped to a hemacytometer. Cells are counting by using a Neubauer-counting chamber. The unstained (viable) and stained (nonviable) cells are counted separately on 9 area of a large square (1 mm²) and added to obtain the total number of cells per sample. An average of three counts was used to calculate the viability percentage as:

[number of viable cells/total number of cells]*100

The cell viability percentages from cultures under starvation conditions were compared with control culture for several days after their addition (D0, D3, D4, D5, D6, D7).
Results
The results were plotted in the histogram of FIG. 7 which represents the evolution of fibroblast viability in vitro during a 7 day period while deprived of nutrients.
The viability of 13(b)αd1 and 13(b)αd2 treated cells remained around 95% up to 7 days of incubation whereas the cell viability in the nutrient deprivation control decreased from 94% after 4 days to 89%, 38% and 8% after 5, 6 and 7 days, respectively.
Compounds 13(b)αd1 and 13(b)αd2 showed thus a preservative effect on skin fibroblasts since cells have been maintained in a healthy state under unfavorable conditions for growth.
Abbreviations
Ala Alanin
Bn Benzyl
Cbz Benzyloxycarbonyl
de Diastereomeric excess
DIBAH Diisobutylaluminium hydride
DMF Dimethylformamide
DMSO Dimethylsulfoxide
eq. Equivalent
Et Ethyl
g Gram
Hz Hertz
mg Milligram
MHz MegaHertz
Min Minute
mL Mililiter
mmol Millimole
µmol Micromole
MOM Methoxymethyl
Ms Mesyl
NMM N-methylmorpholine
nmol Nanomole
NMR Nuclear Magnetic Resonance
PyBOP (1H-Benzotriazol-1-yloxy)tripyrrolidinophosphonium hexafluorophosphate
Rf Retardation factor
THF Tetrahydrofuran
TLC Thin Layer chromatography
TMS Trimethylsilyl

The invention claimed is:
1. A compound of formula (I):

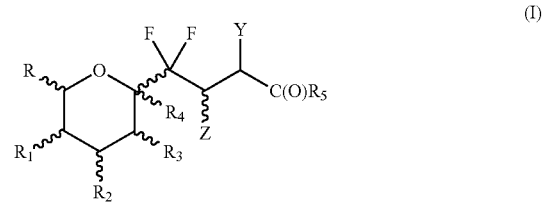

or a pharmaceutically acceptable salt thereof, a tautomer, a stereoisomer or a mixture of stereoisomers in any proportion,
wherein:
Y represents a CN, $NO_2$, $NR_6R_7$ or $CH_2NR_6R_7$ group,
Z represents H or $CH_3$,
R represents a hydrogen or fluorine atom or a $CH_3$, $CH_2F$, $CH_2OSiR^{a1}R^{b1}R^{c1}$, $CH_2OR_8$, $CH_2OC(O)R_9$, $CH_2OCO_2R_{10}$, $CH_2OC(O)NR_{11}R_{12}$, $CH_2OP(O)(OR_{13})_2$ or $CH_2OSO_3R_{14}$ group,
$R_1$ and $R_2$ represent, independently from one another, a fluorine atom or an $OSiR^{a2}R^{b2}R^{c2}$, $OR_{15}$, $OC(O)R_{16}$, $OCO_2R_{17}$, $OC(O)NR_{18}R_{19}$, $OP(O)(OR_{20})_2$ or $OSO_3R_{21}$ group,
$R_3$ represents a fluorine atom or an $OSiR^{a3}R^{b3}R^{c3}$, $OR_{22}$, $OC(O)R_{23}$, $OCO_2R_{24}$, $OCONR_{25}R_{26}$, $OP(O)(OR_{27})_2$, $OSO_3R_{28}$, $N_3$, phtalimidyl, $NR_{29}R_{30}$, $NR_{31}C(O)R_{32}$, $NR_{33}C(O)OR_{34}$, $N(C(O)R_{35})C(O)R_{36}$, $N(C(O)R_{37})C(O)OR_{38}$ and $N(C(O)OR_{39})C(O)OR_{40}$ group,
$R_4$ represents a hydrogen or halogen atom or an $OSiR^{a4}R^{b4}R^{c4}$, $OR_{41}$, $OC(O)R_{42}$, $OCO_2R_{43}$, $OCONR_{44}R_{45}$, $OP(O)(OR_{46})_2$ or $OSO_3R_{47}$ group,
or R and $R_1$, together with the carbon atoms carrying them, form a cyclic acetal having the following formula:

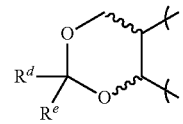

and/or ($R_1$ and $R_2$), ($R_2$ and $R_3$), and/or ($R_3$ and $R_4$), together with the carbon atoms carrying them, form a cyclic acetal having the following formula:

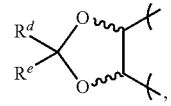

and
$R_5$ represents a hydrogen or halogen atom or a $R_{48}$, $OR_{49}$ or $NR_{50}R_{51}$ group, with:
$R_6$ representing:
a hydrogen atom,
a ($C_1$-$C_6$)alkyl, ($C_2$-$C_6$)alkenyl, ($C_2$-$C_6$)alkynyl, ($C_3$-$C_7$)cycloalkyl, 5- to 7-membered heterocycloalkyl, aryl, heteroaryl, aryl-($C_1$-$C_6$)alkyl, heteroaryl-($C_1$-$C_6$)alkyl, ($C_1$-$C_6$)-alkyl-aryl or ($C_1$-$C_6$)-alkyl-heteroaryl group, this group being possibly substituted with one or more groups chosen among a halogen atom, OH, COOH and CHO, a C(O)R$_{52}$ group, or a C(O)OR$_{53}$ group, R$_7$ representing:

a hydrogen atom, a (C$_1$-C$_6$)alkyl, (C$_2$-C$_6$)alkenyl, (C$_2$-C$_6$)alkynyl, (C$_3$-C$_7$)cycloalkyl, 5- to 7-membered heterocycloalkyl, aryl, heteroaryl, aryl-(C$_1$-C$_6$)alkyl, heteroaryl-(C$_1$-C$_6$)alkyl, (C$_1$-C$_6$)-alkyl-aryl or (C$_1$-C$_6$)-alkyl-heteroaryl group, this group being possibly substituted with one or more groups chosen among a halogen atom, OH, COOH and CHO, a C(O)R$_{52}$ group, a C(O)OR$_{53}$ group, or a N-protecting group, R$_8$, R$_{15}$, R$_{22}$ and R$_{41}$ representing, independently from one another, a hydrogen atom; an O-protecting group; or a (C$_1$-C$_6$)alkyl, (C$_2$-C$_6$)alkenyl, (C$_2$-C$_6$)alkynyl, (C$_3$-C$_7$) cycloalkyl, 5- to 7-membered heterocycloalkyl, aryl, heteroaryl, aryl-(C$_1$-C$_6$)alkyl, heteroaryl-(C$_1$-C$_6$)alkyl, (C$_1$-C$_6$)-alkyl-aryl, (C$_1$-C$_6$)-alkyl-heteroaryl, saccharidic or polysaccharidic group, this group being possibly substituted with one or more groups chosen among a halogen atom, OH, COOH and CHO, R$_9$, R$_{10}$, R$_{16}$, R$_{17}$, R$_{23}$, R$_{24}$, R$_{32}$, R$_{34}$ to R$_{40}$, R$_{42}$, R$_{43}$, R$_{48}$, R$_{52}$ and R$_{53}$ representing, independently from one another, a (C$_1$-C$_6$)alkyl, (C$_2$-C$_6$)alkenyl, (C$_2$-C$_6$)alkynyl, (C$_3$-C$_7$)cycloalkyl, 5- to 7-membered heterocycloalkyl, aryl, heteroaryl, aryl-(C$_1$-C$_6$)alkyl, heteroaryl-(C$_1$-C$_6$)alkyl, (C$_1$-C$_6$)-alkyl-aryl or (C$_1$-C$_6$)-alkyl-heteroaryl group, this group being possibly substituted with one or more groups chosen among a halogen atom, OH, COOH and CHO, R$_{11}$, R$_{12}$, R$_{18}$, R$_{19}$, R$_{25}$, R$_{26}$, R$_{29}$ to R$_{31}$, R$_{33}$, R$_{44}$, R$_{45}$, R$_{50}$ and R$_{51}$ representing, independently from one another, a hydrogen atom or a (C$_1$-C$_6$)alkyl, (C$_2$-C$_6$)alkenyl, (C$_2$-C$_6$)alkynyl, aryl, heteroaryl, aryl-(C$_1$-C$_6$)alkyl, heteroaryl-(C$_1$-C$_6$)alkyl, (C$_1$-C$_6$)-alkyl-aryl or (C$_1$-C$_6$)-alkyl-heteroaryl group, this group being possibly substituted with one or more groups chosen among a halogen atom, OH, COOH and CHO, R$_{13}$, R$_{14}$, R$_{20}$, R$_{21}$, R$_{27}$, R$_{28}$, R$_{46}$ and R$_{47}$ representing, independently from one another, a hydrogen atom or a (C$_1$-C$_6$)alkyl group, R$_{49}$ representing:

a hydrogen atom, a (C$_1$-C$_6$)alkyl, (C$_2$-C$_6$)alkenyl, (C$_2$-C$_6$)alkynyl, (C$_3$-C$_7$)cycloalkyl, 5- to 7-membered heterocycloalkyl, aryl, heteroaryl, aryl-(C$_1$-C$_6$)alkyl, heteroaryl-(C$_1$-C$_6$)alkyl, (C$_1$-C$_6$)-alkyl-aryl or (C$_1$-C$_6$)-alkyl-heteroaryl group, this group being possibly substituted with one or more groups chosen among an halogen atom, OH, COOH and CHO, or a O-protecting group, R$^{a1}$ to R$^{a4}$, R$^{b1}$ to R$^{b4}$ and R$^{c1}$ to R$^{c4}$ representing, independently from one another, a (C$_1$-C$_6$)alkyl, aryl or aryl-(C$_1$-C$_6$)alkyl group, and R$^d$ and R$^e$ representing, independently from one another, a hydrogen atom or a (C$_1$-C$_6$)alkyl group.

2. The compound according to claim 1, wherein said compound has formula (Iα) or (Iβ):

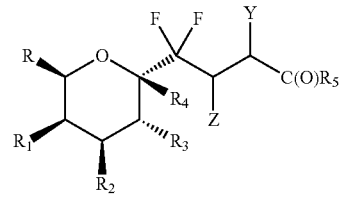

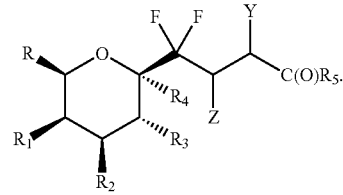

3. The compound according to claim 1, wherein R represents a CH$_2$OR$_3$ group; R$_1$ and R$_2$ represent, independently from one another, an OR$_{15}$ group; and R$_3$ represents an OR$_{22}$ or NR$_{31}$C(O)R$_{32}$ group.

4. The compound according to claim 3, wherein R$_8$, R$_{15}$ and R$_{22}$ represent a hydrogen atom or an O-protecting group, R$_{31}$ represents a hydrogen atom and R$_{32}$ represents a (C$_1$-C$_6$) alkyl group.

5. The compound according to claim 1, wherein R$_4$ represents a hydrogen atom or an OR$_{41}$ group.

6. The compound according to claim 5, wherein R$_{41}$ represents a hydrogen atom or an O-protecting group.

7. The compound according to claim 1, wherein Y represents a NR$_6$R$_7$ or CH$_2$NR$_6$R$_7$ group.

8. The compound according to claim 7, wherein R$_6$ represents a hydrogen atom or a (C$_1$-C$_6$)alkyl group and R$_7$ represents:

a hydrogen atom, a (C$_1$-C$_6$)alkyl, aryl or aryl-(C$_1$-C$_6$)alkyl group, a C(O)R$_{52}$ group, a C(O)OR$_{53}$ group, or an N-protecting group.

9. The compound according to claim 8, wherein R$_{52}$ represents a (C$_1$-C$_6$)alkyl, aryl or aryl-(C$_1$-C$_6$)alkyl group.

10. The compound according to claim 8, wherein R$_{53}$ represents a (C$_1$-C$_6$)alkyl, aryl or aryl-(C$_1$-C$_6$)alkyl group.

11. The compound according to claim 1, wherein R$_5$ represents an OR$_{49}$ group.

12. The compound according to claim 11, wherein R$_{49}$ represents a hydrogen atom, a (C$_1$-C$_6$)alkyl group or an O-protecting group.

13. The compound according to claim 1, wherein Y represents a NR$_6$R$_7$ or CH$_2$NR$_6$R$_7$ group and R$_5$ represents an OR$_{49}$ group, with:

R$_6$ and R$_7$ representing each a hydrogen atom and R$_{49}$ representing an O-protecting group, or R$_{49}$ and R$_6$ representing each a hydrogen atom and R$_7$ representing a N-protecting group.

14. The compound according to claim 1, selected from the group consisting of the following compounds:

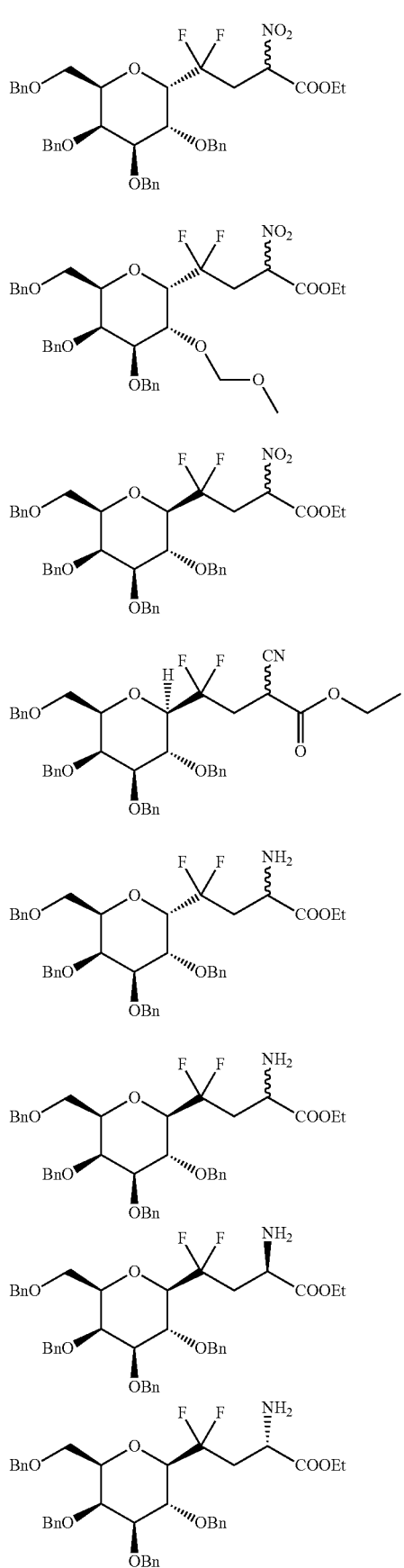
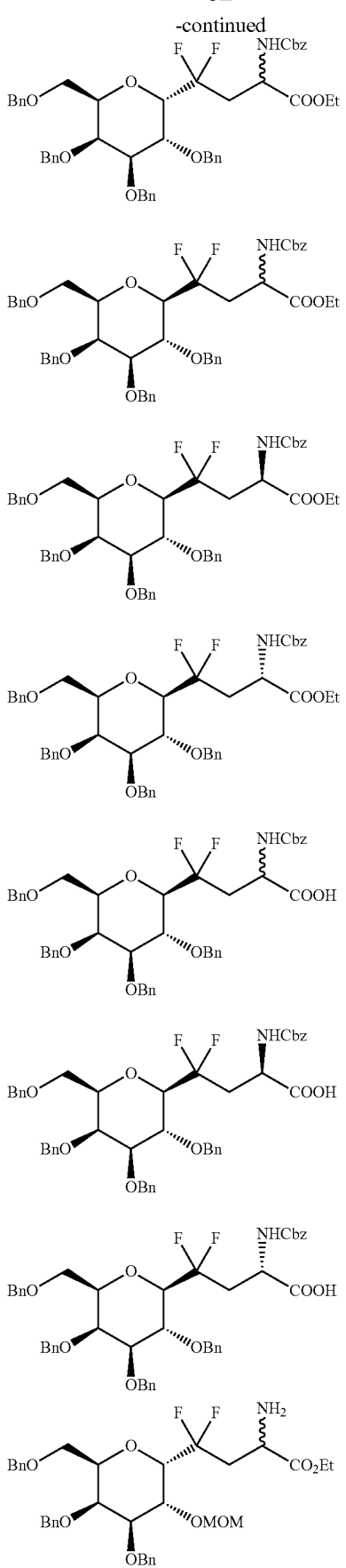

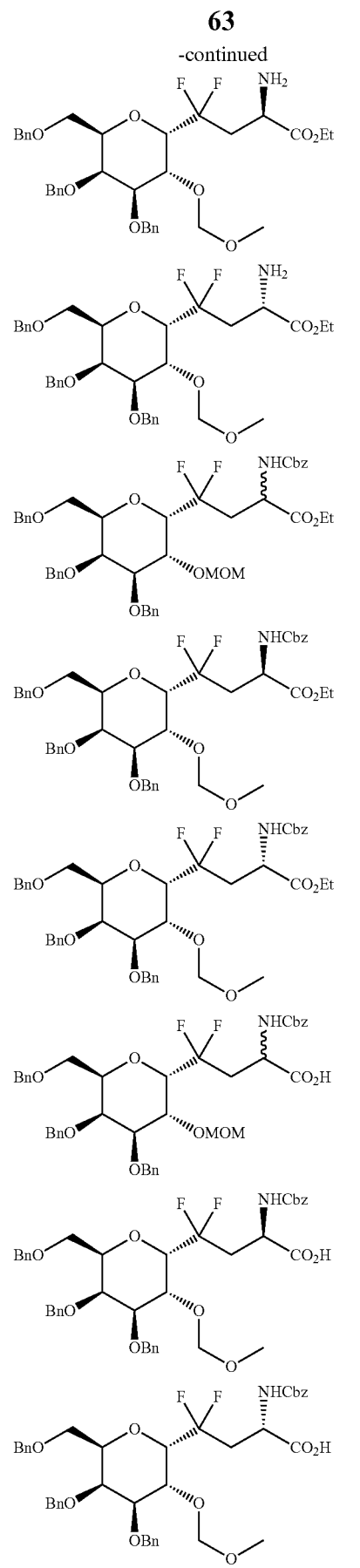

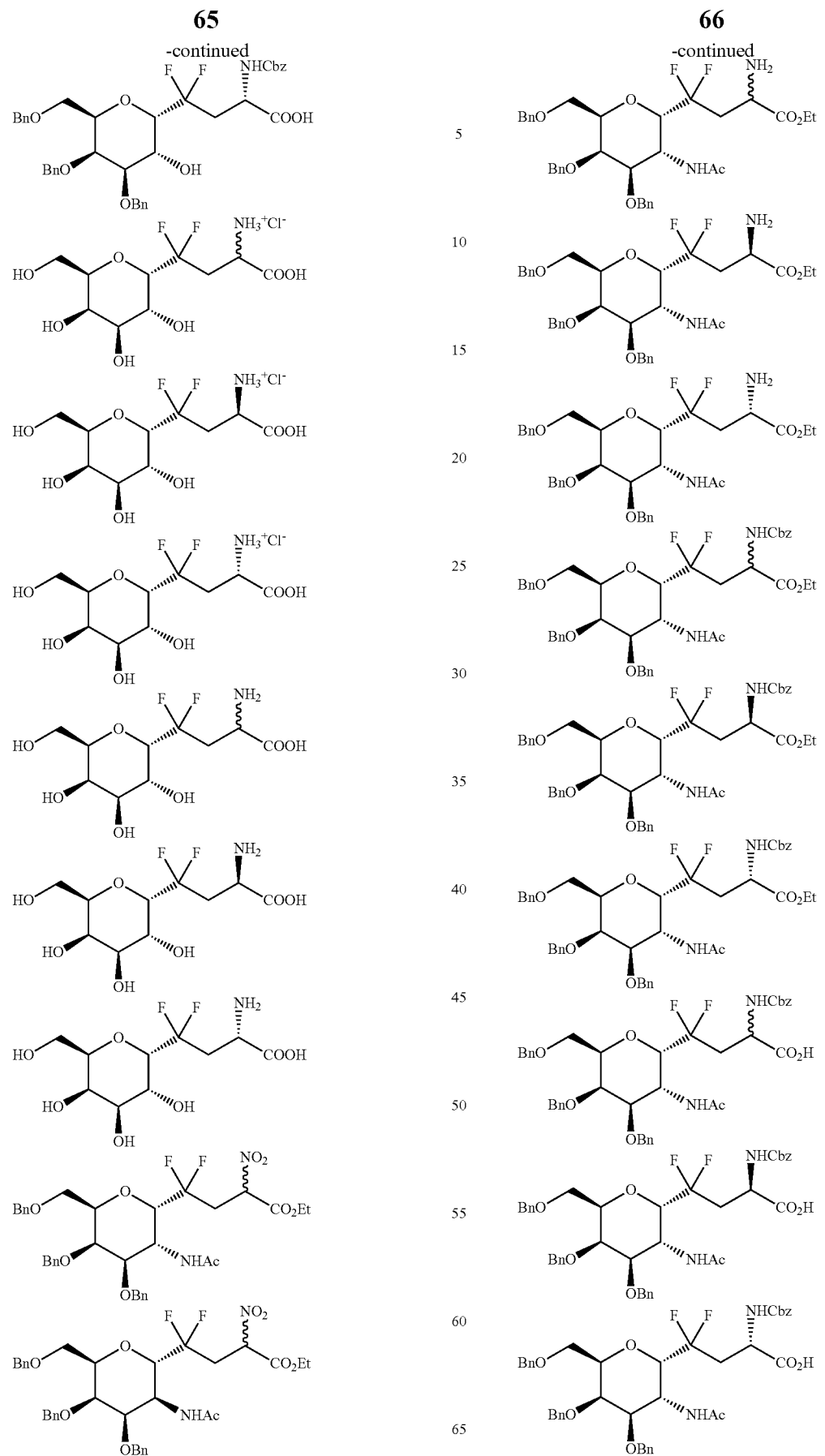

-continued

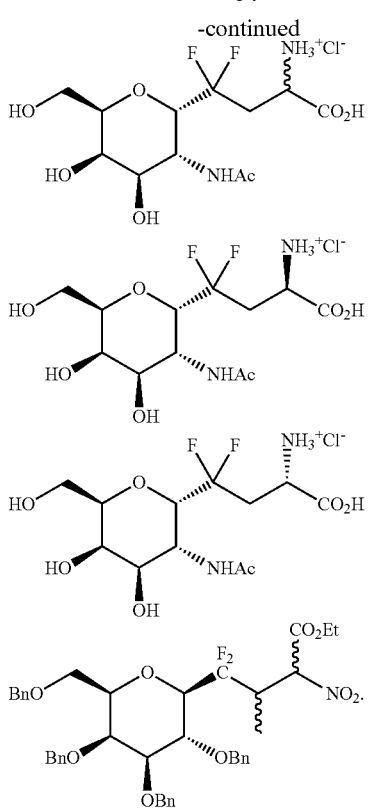

15. A process for preparing a compound of formula (I) according to claim 1 wherein Z=H, comprising the following successive steps:
a) dehydration of a compound of formula (II):

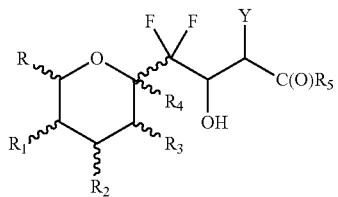

wherein R, R$_1$, R$_2$, R$_3$, R$_4$, R$_5$ and Y are as defined in claim 1,
to give a compound of formula (III):

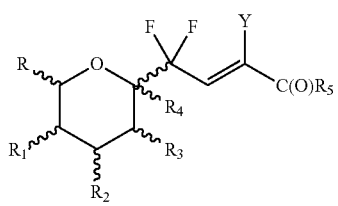

wherein R, R$_1$, R$_2$, R$_3$, R$_4$, R$_5$ and Y are as defined in claim 1, and
b) hydrogenation of the compound of formula (III) obtained in the previous step to give a compound of formula (I) with Z=H.

16. A process for preparing a compound of formula (I) according to claim 1 wherein Z=CH$_3$, comprising the following successive steps:
i) reaction of a compound of formula (VII):

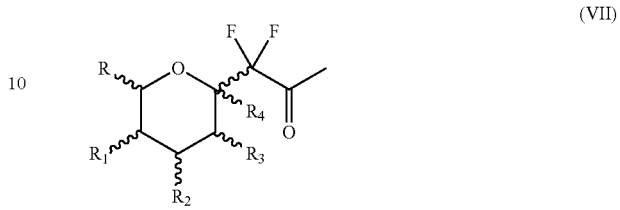

wherein R, R$_1$, R$_2$, R$_3$ and R$_4$ are as defined in claim 1, with a compound of formula (V):

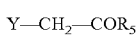

wherein R$_5$ is as defined in claim 1 and Y=NO$_2$ or CN, to give a compound of formula (VIII):

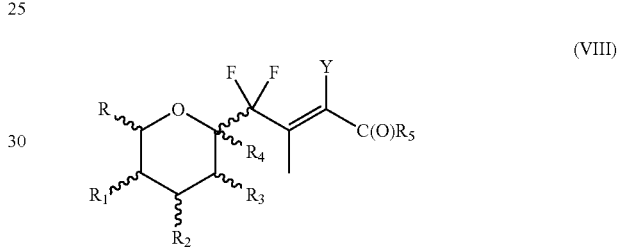

wherein R, R$_1$, R$_2$, R$_3$, R$_4$ and R$_5$ are as defined in claim 1 and Y=NO$_2$ or CN, ii) optionally reduction of the compound of formula (VIII) obtained in the previous step i) to give a compound of formula (I) wherein Z=CH$_3$ and Y=NO$_2$ or CN, iii) optionally reduction of the NO$_2$ or CN function of the compound of formula (I) obtained in the previous step ii) to give a compound of formula (I) wherein Z=CH$_3$ and Y=NH$_2$ or CH$_2$NH$_2$, and iv) optionally substitution of the amino function of the compound of formula (I) obtained in the previous step iii) to give a compound of formula (I) wherein Z=CH$_3$ and Y=NR$_6$R$_7$ or CH$_2$NR$_6$R$_7$, with the proviso that at least R$_6$ or R$_7$ is not a hydrogen atom.

17. A peptide (VI) wherein at least one amino acid has been replaced with a compound of formula (I) according to claim 1 wherein Y=NHR$_7$ or CH$_2$NHR$_7$ and/or R$_5$=OH, the Y and/or R$_5$ group being linked to an amino acid of the peptide by a peptide bond.

18. The peptide according to claim 17 selected from the group consisting of the following compounds:

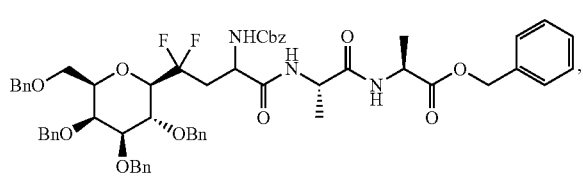

-continued

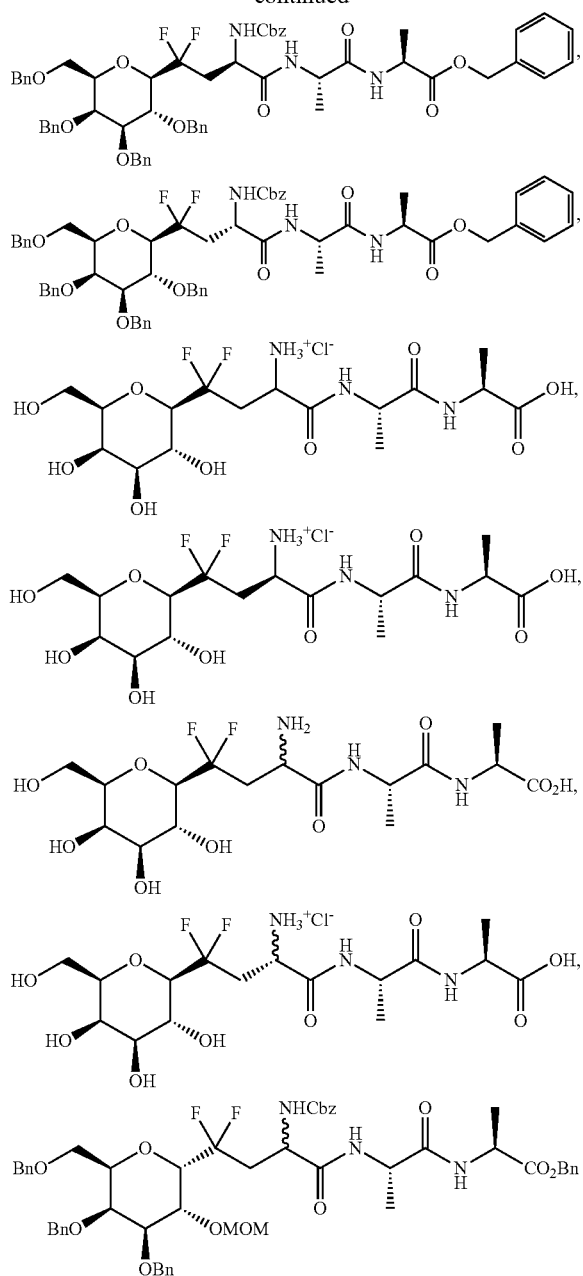

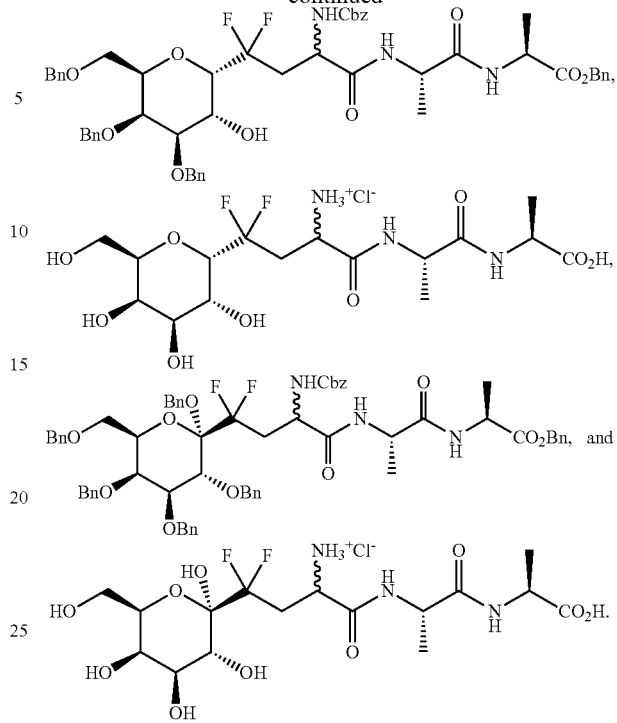

19. A pharmaceutical or cosmetic composition comprising at least one peptide (VI) according to claim 17 and a pharmaceutically acceptable carrier.

20. The peptide according to claim 17, wherein the at least one amino acid is a serine or a threonine.

21. A method of treating a viral, bacterial or inflammatory disease comprising administering to a person in need thereof an effective amount of a peptide according to claim 17.

22. A method comprising preserving a biological material using a peptide (VI) according to claim 17.

23. The method according to claim 22, wherein the biological material is selected from the group consisting of cells, tissues and organs.

24. The method according to claim 22, performed at a temperature below 37° C.

25. The method according to claim 24, performed at temperature below 0° C.

26. A method of treating skin aging comprising administering to a person in need thereof an effective amount of a peptide according to claim 17.

* * * * *